US008815241B2

(12) United States Patent
Yamamoto

(10) Patent No.: US 8,815,241 B2
(45) Date of Patent: Aug. 26, 2014

(54) USE OF COMBINATION OF ANTI-ANGIOGENIC SUBSTANCE AND C-KIT KINASE INHIBITOR

(75) Inventor: Yuji Yamamoto, Ibaraki (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 13/205,328

(22) Filed: Aug. 8, 2011

(65) Prior Publication Data

US 2011/0293615 A1    Dec. 1, 2011

Related U.S. Application Data

(62) Division of application No. 12/092,539, filed as application No. PCT/JP2006/322514 on Nov. 7, 2006, now abandoned.

(30) Foreign Application Priority Data

Nov. 7, 2005  (JP) ................................. 2005-322946

(51) Int. Cl.
| A61K 39/395 | (2006.01) |
| A61K 31/506 | (2006.01) |
| A61K 31/47 | (2006.01) |
| A61P 35/00 | (2006.01) |
| A61K 31/4709 | (2006.01) |
| A61K 31/404 | (2006.01) |
| A61K 31/517 | (2006.01) |
| A61K 45/06 | (2006.01) |
| A61K 31/519 | (2006.01) |
| A61K 31/502 | (2006.01) |
| A61K 31/5377 | (2006.01) |
| A61K 31/4439 | (2006.01) |
| A61K 31/4409 | (2006.01) |
| C07D 215/48 | (2006.01) |

(52) U.S. Cl.
CPC .......... *C07D 215/48* (2013.01); *A61K 31/4709* (2013.01); *A61K 31/404* (2013.01); *A61K 31/517* (2013.01); *A61K 31/47* (2013.01); *A61K 45/06* (2013.01); *A61K 31/519* (2013.01); *A61K 31/502* (2013.01); *A61K 31/5377* (2013.01); *A61K 31/506* (2013.01); *A61K 31/4439* (2013.01); *A61K 31/4409* (2013.01)
USPC ................. 424/138.1; 514/311; 514/252.18

(58) Field of Classification Search
None
See application file for complete search history.

(56) References Cited

U.S. PATENT DOCUMENTS

| 4,526,988 A | 7/1985 | Hertel et al. |
| 4,563,417 A | 1/1986 | Albarella et al. |
| 4,582,789 A | 4/1986 | Sheldon, III et al. |
| 4,742,003 A | 5/1988 | Derynck et al. |
| 4,764,454 A | 8/1988 | Ichijima et al. |
| 5,180,818 A | 1/1993 | Cech et al. |
| 5,445,934 A | 8/1995 | Fodor et al. |
| 5,464,826 A | 11/1995 | Grindey et al. |
| 5,487,889 A | 1/1996 | Eckert et al. |
| 5,624,937 A | 4/1997 | Reel et al. |
| 5,650,376 A | 7/1997 | Badaye et al. |
| 5,656,454 A | 8/1997 | Lee et al. |
| 5,658,374 A | 8/1997 | Glover |
| 5,733,913 A | 3/1998 | Blankley et al. |
| 5,747,651 A | 5/1998 | Lemischka |
| 5,750,376 A | 5/1998 | Weiss et al. |
| 5,770,599 A | 6/1998 | Gibson |
| 5,792,783 A | 8/1998 | Tang et al. |
| 5,891,996 A | 4/1999 | Mateo de Acosta del Rio et al. |
| 5,948,438 A | 9/1999 | Staniforth et al. |
| 6,027,880 A | 2/2000 | Cronin et al. |
| 6,057,100 A | 5/2000 | Heyneker |
| 6,143,764 A | 11/2000 | Kubo et al. |
| 6,156,501 A | 12/2000 | McGall et al. |
| 6,156,522 A | 12/2000 | Keay et al. |
| 6,217,866 B1 | 4/2001 | Schlessinger et al. |
| 6,261,776 B1 | 7/2001 | Pirrung et al. |
| 6,346,398 B1 | 2/2002 | Pavco et al. |
| 6,476,040 B1 | 11/2002 | Norris et al. |
| 6,524,583 B1 | 2/2003 | Thorpe et al. |
| 6,534,535 B1 | 3/2003 | Zhu et al. |
| 6,576,424 B2 | 6/2003 | Fodor et al. |
| 6,676,941 B2 | 1/2004 | Thorpe et al. |
| 6,762,180 B1 | 7/2004 | Roth et al. |
| 6,797,823 B1 | 9/2004 | Kubo et al. |
| 6,811,779 B2 | 11/2004 | Rockwell et al. |

(Continued)

FOREIGN PATENT DOCUMENTS

| CN | 1473041 | 2/2004 |
| CN | 1478078 | 2/2004 |

(Continued)

OTHER PUBLICATIONS

Okura et al., Effects of monoclonal anti-c-kit antibody (ACK2) on melanocytes in newborn mice, 105(3) J. Invest. Dermatol. 322-8 (Sep. 1995).*
EESR directed at application No. 06832529.9 issued on Jul. 29, 2009, 6 pages.
Naruse, et al., "Antitumor Activity of the Selective Epidermal Growth Factor Receptor-Tyrosine Kinase Inhibitor (EGFR-TKI) IRESSA . . . In Vivo", Int. J. Cancer, 98:310-315, (2002).
Office Action directed at application No. 4025700.8 issued on Apr. 10, 2006, 3 pages.

(Continued)

*Primary Examiner* — Janet L Andres
*Assistant Examiner* — Timothy R Rozof
(74) *Attorney, Agent, or Firm* — Fish & Richardson P.C.

(57) ABSTRACT

The object of the present invention is to find a pharmaceutical composition and a method for treating cancer that show an excellent antitumor effect. Combinational use of 4-(3-chloro-4-(cyclopropylaminocarbonyl)aminophenoxy)-7-methoxy-6-quinolinecarboxamide and analogues thereof can result in an excellent antitumor effect when combined with a substance having a c-kit kinase-inhibiting activity.

2 Claims, 2 Drawing Sheets

(56) References Cited

U.S. PATENT DOCUMENTS

| | | |
|---|---|---|
| 6,812,341 B1 | 11/2004 | Conrad |
| 6,821,987 B2 | 11/2004 | Kubo et al. |
| 7,005,430 B2 | 2/2006 | Ueno et al. |
| 7,101,663 B2 | 9/2006 | Godfrey et al. |
| 7,135,466 B2 | 11/2006 | Sakai et al. |
| 7,169,789 B2 | 1/2007 | Kubo et al. |
| 7,253,286 B2 | 8/2007 | Funahashi et al. |
| 7,435,590 B2 | 10/2008 | Komurasaki |
| 7,485,658 B2 | 2/2009 | Bolger et al. |
| 7,495,104 B2 | 2/2009 | Miwa et al. |
| 7,550,483 B2 | 6/2009 | Sakaguchi et al. |
| 7,612,092 B2 | 11/2009 | Funahashi et al. |
| 7,612,208 B2 | 11/2009 | Matsushima et al. |
| 7,855,290 B2 | 12/2010 | Matsushima et al. |
| 7,973,160 B2 | 7/2011 | Funahashi et al. |
| 8,288,538 B2 | 10/2012 | Matsushima et al. |
| 8,372,981 B2 | 2/2013 | Funahashi et al. |
| 8,377,938 B2 | 2/2013 | Matsushima et al. |
| 2002/0010203 A1 | 1/2002 | Lipson et al. |
| 2002/0040127 A1 | 4/2002 | Jiang et al. |
| 2003/0013208 A1 | 1/2003 | Jendoubi |
| 2003/0087907 A1 | 5/2003 | Kubo et al. |
| 2003/0113713 A1 | 6/2003 | Glezer et al. |
| 2003/0215523 A1 | 11/2003 | Ozawa et al. |
| 2004/0009965 A1 | 1/2004 | Collins et al. |
| 2004/0034026 A1 | 2/2004 | Wood et al. |
| 2004/0053908 A1 | 3/2004 | Funahashi et al. |
| 2004/0086915 A1 | 5/2004 | Lin et al. |
| 2004/0132727 A1 | 7/2004 | Sakai et al. |
| 2004/0152759 A1 | 8/2004 | Abrams et al. |
| 2004/0167134 A1 | 8/2004 | Bruns et al. |
| 2004/0171068 A1 | 9/2004 | Wehland et al. |
| 2004/0191254 A1 | 9/2004 | Fagin |
| 2004/0229876 A1 | 11/2004 | Kubo et al. |
| 2004/0242506 A1 | 12/2004 | Barges Causeret et al. |
| 2004/0253205 A1 | 12/2004 | Yamamoto et al. |
| 2004/0259834 A1 | 12/2004 | Kasprzyk et al. |
| 2005/0014727 A1 | 1/2005 | Muller et al. |
| 2005/0049264 A1 | 3/2005 | Miwa et al. |
| 2005/0119303 A1 | 6/2005 | Wakabayashi et al. |
| 2005/0176802 A1 | 8/2005 | Tang et al. |
| 2005/0187236 A1 | 8/2005 | Tsuruoka et al. |
| 2005/0209452 A1* | 9/2005 | Bornsen et al. ............... 544/122 |
| 2005/0272688 A1 | 12/2005 | Higgins et al. |
| 2005/0277652 A1 | 12/2005 | Matsushima et al. |
| 2006/0004017 A1 | 1/2006 | Stokes et al. |
| 2006/0004029 A1 | 1/2006 | Tsuruoka et al. |
| 2006/0057195 A1 | 3/2006 | Nonomura et al. |
| 2006/0079494 A1 | 4/2006 | Santi et al. |
| 2006/0135486 A1 | 6/2006 | Owa et al. |
| 2006/0160832 A1 | 7/2006 | Funahashi et al. |
| 2006/0189629 A1 | 8/2006 | Bolger et al. |
| 2006/0292192 A1 | 12/2006 | Hasenzahl et al. |
| 2007/0004773 A1 | 1/2007 | Sakaguchi et al. |
| 2007/0027318 A1 | 2/2007 | Kubo et al. |
| 2007/0032521 A1 | 2/2007 | Moussy et al. |
| 2007/0037849 A1 | 2/2007 | Naito et al. |
| 2007/0078159 A1 | 4/2007 | Matsushima |
| 2007/0117842 A1 | 5/2007 | Arimoto et al. |
| 2007/0214604 A1 | 9/2007 | Yi |
| 2008/0214604 A1 | 9/2008 | Furitsu et al. |
| 2008/0241835 A1 | 10/2008 | Mehraban et al. |
| 2009/0047278 A1 | 2/2009 | Owa et al. |
| 2009/0047365 A1 | 2/2009 | Owa et al. |
| 2009/0053236 A1 | 2/2009 | Yamamoto et al. |
| 2009/0202541 A1 | 8/2009 | Bruns et al. |
| 2009/0247576 A1 | 10/2009 | Kamata et al. |
| 2009/0264464 A1 | 10/2009 | Yamamoto et al. |
| 2009/0304694 A1 | 12/2009 | Oliner et al. |
| 2010/0048503 A1 | 2/2010 | Yamamoto |
| 2010/0048620 A1 | 2/2010 | Yamamoto |
| 2010/0092490 A1 | 4/2010 | Uenaka et al. |
| 2010/0105031 A1 | 4/2010 | Matsui et al. |
| 2010/0239688 A1 | 9/2010 | Yamamoto |
| 2010/0324087 A1 | 12/2010 | Yamamoto |
| 2011/0118470 A1 | 5/2011 | Funahashi et al. |
| 2011/0158983 A1 | 6/2011 | Bascomb et al. |
| 2011/0293615 A1 | 12/2011 | Yamamoto |
| 2012/0077842 A1 | 3/2012 | Bando |
| 2012/0207753 A1 | 8/2012 | Yu et al. |
| 2012/0219522 A1 | 8/2012 | Xl |
| 2012/0244209 A1 | 9/2012 | Roth et al. |
| 2012/0263677 A1 | 10/2012 | Eagle et al. |
| 2012/0283206 A1 | 11/2012 | Bruns et al. |
| 2013/0296365 A1 | 11/2013 | Bando |

FOREIGN PATENT DOCUMENTS

| | | |
|---|---|---|
| CN | 1890220 | 1/2007 |
| CN | 101001629 | 7/2007 |
| CN | 101029022 | 9/2007 |
| CN | 101198590 | 6/2008 |
| CN | 101316590 | 12/2008 |
| CN | 101454311 | 6/2009 |
| CN | 101616671 | 12/2009 |
| CN | 102470133 | 5/2012 |
| EP | 297580 | 1/1989 |
| EP | 405425 | 1/1991 |
| EP | 602851 | 6/1994 |
| EP | 684820 | 6/1995 |
| EP | 795556 | 9/1997 |
| EP | 837063 | 4/1998 |
| EP | 870842 | 10/1998 |
| EP | 930305 | 7/1999 |
| EP | 930310 | 7/1999 |
| EP | 1029853 | 8/2000 |
| EP | 1044969 | 10/2000 |
| EP | 543942 | 1/2001 |
| EP | 1153920 | 11/2001 |
| EP | 712863 | 2/2002 |
| EP | 1331005 | 7/2003 |
| EP | 1382604 A1 | 1/2004 |
| EP | 1411046 | 4/2004 |
| EP | 1415987 | 5/2004 |
| EP | 1447405 | 1/2005 |
| EP | 1506962 | 2/2005 |
| EP | 1522540 | 4/2005 |
| EP | 1535910 | 6/2005 |
| EP | 1552833 | 7/2005 |
| EP | 1566379 | 8/2005 |
| EP | 1604665 | 12/2005 |
| EP | 1683785 | 7/2006 |
| EP | 1698623 | 9/2006 |
| EP | 1797877 | 6/2007 |
| EP | 1797881 | 6/2007 |
| EP | 1859797 | 11/2007 |
| EP | 1894918 | 3/2008 |
| EP | 1925676 | 5/2008 |
| EP | 1925941 | 5/2008 |
| EP | 1949902 | 7/2008 |
| EP | 1964837 | 9/2008 |
| EP | 2116246 | 11/2009 |
| EP | 2119707 | 11/2009 |
| EP | 2133094 A4 | 12/2009 |
| EP | 2133095 A1 | 12/2009 |
| EP | 2218712 | 8/2010 |
| GB | 2253848 | 9/1992 |
| IN | 236500 | 11/2009 |
| JP | S63-028427 | 2/1988 |
| JP | 01-022874 | 1/1989 |
| JP | 02-291295 | 12/1990 |
| JP | 04-341454 | 11/1992 |
| JP | 06-153952 | 6/1994 |
| JP | 07-176103 | 7/1995 |
| JP | 08-045927 | 2/1996 |
| JP | 08-048078 | 2/1996 |
| JP | 09-023885 | 1/1997 |
| JP | 09-234074 | 9/1997 |
| JP | 11-501343 | 2/1999 |
| JP | 11-143429 | 5/1999 |
| JP | 11-158149 | 6/1999 |
| JP | 11-322596 | 11/1999 |
| JP | 3040486 | 3/2000 |
| JP | 3088018 | 7/2000 |

(56) References Cited

FOREIGN PATENT DOCUMENTS

| | | |
|---|---|---|
| JP | 2000-328080 | 11/2000 |
| JP | 2001-131071 | 5/2001 |
| JP | 2002-003365 | 1/2002 |
| JP | 2002-114710 | 4/2002 |
| JP | 2002-536414 | 10/2002 |
| JP | 2003-012668 | 1/2003 |
| JP | 2003-026576 | 1/2003 |
| JP | 3420549 | 4/2003 |
| JP | 2003-525595 | 9/2003 |
| JP | 2004-513964 | 5/2004 |
| JP | 2004-155773 | 6/2004 |
| JP | 2004-531549 | 10/2004 |
| JP | 2005-501074 | 1/2005 |
| JP | 2005-504111 | 2/2005 |
| JP | 2005-520834 | 7/2005 |
| JP | 3712393 | 8/2005 |
| JP | 2005-272474 | 10/2005 |
| JP | 2006-508981 | 3/2006 |
| JP | 2006-515884 | 6/2006 |
| KR | 10-0589032 | 6/2006 |
| WO | WO 86/03222 | 6/1986 |
| WO | WO 92/20642 | 11/1992 |
| WO | 94/09010 | 4/1994 |
| WO | WO 95/15758 | 6/1995 |
| WO | WO 95/19774 | 7/1995 |
| WO | WO 96/09294 | 3/1996 |
| WO | WO 96/26997 | 9/1996 |
| WO | WO 96/30347 | 10/1996 |
| WO | WO 96/33980 | 10/1996 |
| WO | WO 96/39145 | 12/1996 |
| WO | WO 96/40142 | 12/1996 |
| WO | WO 97/03069 | 1/1997 |
| WO | WO 97/13760 | 4/1997 |
| WO | WO 97/13771 | 4/1997 |
| WO | WO 97/17329 | 5/1997 |
| WO | WO 97/21437 | 6/1997 |
| WO | WO 97/38984 | 10/1997 |
| WO | WO 97/48693 | 12/1997 |
| WO | WO 98/00134 | 1/1998 |
| WO | WO 98/02434 | 1/1998 |
| WO | WO 98/02437 | 1/1998 |
| WO | WO 98/02438 | 1/1998 |
| WO | WO 98/13350 | 4/1998 |
| WO | WO 98/14437 | 4/1998 |
| WO | WO 98/23613 | 6/1998 |
| WO | WO 98/32436 | 7/1998 |
| WO | WO 98/35958 | 8/1998 |
| WO | WO 98/37079 | 8/1998 |
| WO | WO 98/50346 | 11/1998 |
| WO | WO 98/52558 | 11/1998 |
| WO | WO 99/00357 | 1/1999 |
| WO | WO 99/32106 | 7/1999 |
| WO | WO 99/32110 | 7/1999 |
| WO | WO 99/32111 | 7/1999 |
| WO | WO 99/32436 | 7/1999 |
| WO | WO 99/35132 | 7/1999 |
| WO | WO 99/35146 | 7/1999 |
| WO | WO 99/43654 | 9/1999 |
| WO | WO 99/62890 | 12/1999 |
| WO | WO 00/31048 | 6/2000 |
| WO | WO 00/42012 | 7/2000 |
| WO | WO 00/43366 | 7/2000 |
| WO | WO 00/43384 | 7/2000 |
| WO | WO 00/44728 | 8/2000 |
| WO | WO 00/47212 | 8/2000 |
| WO | WO 00/50405 | 8/2000 |
| WO | WO 00/71097 | 11/2000 |
| WO | WO 01/02369 | 1/2001 |
| WO | WO 01/23375 | 4/2001 |
| WO | WO 01/27081 | 4/2001 |
| WO | WO 01/32926 | 5/2001 |
| WO | WO 01/36403 | 5/2001 |
| WO | WO 01/40217 | 6/2001 |
| WO | WO 01/45689 | 6/2001 |
| WO | WO 01/47890 | 7/2001 |
| WO | WO 01/47931 | 7/2001 |
| WO | WO 01/60814 | 8/2001 |
| WO | WO 02/16348 | 2/2002 |
| WO | WO 02/32872 | 4/2002 |
| WO | WO 02/36117 | 5/2002 |
| WO | WO 02/41882 | 5/2002 |
| WO | WO 02/44156 | 6/2002 |
| WO | WO 02/072578 | 9/2002 |
| WO | WO 02/080975 | 10/2002 |
| WO | WO 02/088110 | 11/2002 |
| WO | WO 02/092091 | 11/2002 |
| WO | WO 03/006462 | 1/2003 |
| WO | WO 03/013529 | 2/2003 |
| WO | WO 03/024386 | 3/2003 |
| WO | 03/033472 | 4/2003 |
| WO | WO 03/027102 | 4/2003 |
| WO | WO 03/028711 | 4/2003 |
| WO | WO 03/033472 | 4/2003 |
| WO | WO 03/050090 | 6/2003 |
| WO | WO 03/074045 | 9/2003 |
| WO | WO 03/079020 | 9/2003 |
| WO | WO 2004/006862 | 1/2004 |
| WO | WO 2004/020434 | 3/2004 |
| WO | WO 2004/032872 | 4/2004 |
| WO | WO 2004/032937 | 4/2004 |
| WO | WO 2004/035052 | 4/2004 |
| WO | WO 2004/039782 | 5/2004 |
| WO | WO 2004/041308 | 5/2004 |
| WO | WO 2004/043472 | 5/2004 |
| WO | 2004/045523 | 6/2004 |
| WO | WO 2004/064730 | 8/2004 |
| WO | WO 2004/078144 | 9/2004 |
| WO | WO 2004/080462 | 9/2004 |
| WO | WO 2004/080966 | 9/2004 |
| WO | WO 2004/101526 | 11/2004 |
| WO | WO2005004870 A1 | 1/2005 |
| WO | 2005/021537 | 3/2005 |
| WO | WO 2005/027972 | 3/2005 |
| WO | WO 2005/030140 | 4/2005 |
| WO | WO 2005/044788 | 5/2005 |
| WO | WO 2005/051366 | 6/2005 |
| WO | WO 2005/056764 | 6/2005 |
| WO | WO 2005/063713 | 7/2005 |
| WO | WO 2005/082854 | 9/2005 |
| WO | WO 2005/092896 | 10/2005 |
| WO | WO 2005/117887 | 12/2005 |
| WO | WO 2006/030826 | 3/2006 |
| WO | WO 2006/030941 | 3/2006 |
| WO | WO 2006/030947 | 3/2006 |
| WO | WO 2006/062984 | 6/2006 |
| WO | WO 2006/090930 | 8/2006 |
| WO | WO 2006/090931 | 8/2006 |
| WO | WO 2006/036941 | 12/2006 |
| WO | WO 2006/137474 | 12/2006 |
| WO | 2007/000347 | 1/2007 |
| WO | WO 2007/014335 | 2/2007 |
| WO | WO 2007/015569 | 2/2007 |
| WO | WO 2007/015578 | 2/2007 |
| WO | 2007/023768 | 3/2007 |
| WO | WO 2007/040565 | 4/2007 |
| WO | WO 2007/052849 | 5/2007 |
| WO | WO 2007/052850 | 5/2007 |
| WO | WO 2007/061127 | 5/2007 |
| WO | WO 2007/061130 | 5/2007 |
| WO | WO 2007/136103 | 11/2007 |
| WO | 2008/023698 | 2/2008 |
| WO | 2008/026748 | 3/2008 |
| WO | 2008/088088 | 7/2008 |
| WO | 2008/093855 | 8/2008 |
| WO | 2009/060945 | 5/2009 |
| WO | 2009/077874 | 6/2009 |
| WO | 2009/096377 | 8/2009 |
| WO | 2009/140549 | 11/2009 |

OTHER PUBLICATIONS

Search Report directed at application No. 4719054.1 issued on Apr. 17, 2009, 4 pages.
Search Report directed at application No. 4818213.3 issued on Jul. 30, 2007, 3 pages.

(56) References Cited

OTHER PUBLICATIONS

"NCBI GenBank Accession No. NM_000222", Feb. 11, 2008.
"Proceedings of the American Association for Cancer Research", vol. 45, Mar. 2004, p. 1070-p. 1071.
"Redefining The Frontiers of Science 94th Annual Meeting", American Association for Cancer Research, 2003, vol. 44, Washington D.C., USA, Jul. 11-14, 2003.
"Types of Lung Cancer", Cancer care, Inc., Cancer care, Inc., Aug. 13, 2009.
Abuzar, S. et al., "Synthesis of some new 7-chloro-4-substituted quinolines as potential antiparasitic agents", Eur. J. Med. Chem.,vol. 21,No. 1, 1986, p. 5-p. 8.
Agarwal et al., "Binding of Discoidin Domain Receptor 2 to Collagen I: An Atomic Force Microscopy Investigation", Biochemistry 41:11091-11098 (2002).
Alvares et al., "A Novel Germ-Line Point Mutation in RET Exon 8 (Gly533Cys) in a Large Kindred with Familial Medullary Thyroid Carcinoma" The Journal of Clinical Endocrinology & Metabolism 88(11):5438-5443.
Anonymous, Scientific Discussion, Internet Citation, Jan. 1, 2004, p. 1/61-p. 61/61, XP007918143.
Asuno-Shinyaku, "The New Drugs of Tomorrow", Update Summary Dec. 2006 with English translation (14 pages).
Baker et al., "Blockade of Vascular Endothelial Growth Factor Receptor and Epidermal Growth Factor Receptor Signaling for Therapy of Metastatic Human Pancreatic Cancer", Cancer Research 62: 1996-2003 (2002).
Bastin et al., "Salt Selection and Optmiisation for Pharmaceutical New Chemical Entities," Organic Process Research and Development, Cambridge, GB, vol. 4, No. 5, Jan. 1, 2000, p. 427-p. 435, XP002228592.
Bellone, et al., "Growh Stimulation of Colorectal Carcinoma Cells via the c-kit Rector is Inhibited by TGF-β-1", Journal of Cellular Physiology,172, 1997, p. 1-p. 11.
Benjamin et al., "Selective ablation of immature blood vessels in established human tumors follows vascular endothelial growth factor withdrawal", The J. of Clin. Invest. 103(2):159-165 (1999).
Berdel, et al, "Recombinant Human Stem Cell Factor Stimulates Growth of a Human Glioblastoma Cell Line Expressing c-kit Protooncogene", Cancer Research, 52, 1992, p. 3498-p. 3502.
Berge et al., Journal of Pharmaceutical Sciences, American Pharmaceutical Association, Washington, US, vol. 66, No. 1, Jan. 1, 1977, p. 1-p. 19, XP002550655.
Bergers et al., "Benefits of targeting both pericytes and endothelial cells in the tumor vasculature with kinase inhibitors", The Journal of Clinical Investigation 111(9):1287-1295 (2003).
Blume-Jensen, et al., "Activation of the Human c-kit Product by Ligand-Induced Dimerization Mediates Circular Actin Reorganization and Chemotaxis", The EMBO Journal, 10(13), 1991, p. 4121-p. 4128.
Boissan, et al., "c-Kit and c-kit mutations in mastocytosis and other hematological diseaseas", J. Leukocyte Biol., 67:135-148, (2000).
Bradley Anderson et al., "Preparation of Water-soluble Compounds through Salt Formation", The Practice of Medicinal Chemistry, Technomics, pp. 347-349, 355-356 (1999).
Bruns et al., "Effect of the Vascular Endothelial Growth Factor Receptor-2 Antibody DC101 Plus Gemcitabine on Growth, Metastasis and Angiogenesis of Human Pancreatic Cancer Growing Orthotopically in Nude Mice", Int. J. Cancer 102:101-108 (2002).
Bussolino, et al, "Role of Soluble Mediators in Angiogenesis", Eur. J. Cancer, 32A(14): , 1996, p. 2401-p. 2412.
Cairns et al., "New antiallergic pyrano[3,2g]quinoline-2,8-dicarboxylic acids with potential for the topical treatment of asthma", Cairns et al, Journal of Medicinal Chemistry 8(12), 1985, p. 1832-p. 1842.
Capellen et al., "Frequent activating mutations of FGFR3 in human bladder and cervix carcinomas", Nature Genetics, 23:18-20 (1999).
Carlomagno et al., "Bay 43-9006 Inhibition of Oncogenic RET Mutants", Journal of the National Cancer Institute 98(5):326-334 (2006).
Carlomagno et al., "ZD6474, an Orally Available Inhibitor of KDR Tyrosine Kinase Actvity, Efficiently Blocks Oncogenic RET Kinases", Cancer Research 62:7284-7290 (2002).
Chen et al., "FGFR3 as a therapeutic target of the small molecule inhibitor PKC412 in hematopoietic malignancies", Oncogene 24:8259-8267 (2005).
Chesi et al., "Activated fibroblast growth factor receptor 3 is an oncogene that contributes to tumor progression in multiple myeloma", Blood 97(3):729-736 (2001).
Chesi et al., "Frequent translocation t(4;14)(p16.3;q32.3) in multiple myeloma is associated with increased expression and activating mutations of fibroblast growth factor receptor", Nature Genetics, 3 16:260-264 (1997).
Ciardiello, et al., "ZD1839 (IRESSA), An EGFR-Selective Tyrosine Kinase Inhibitor, Enhances Taxane Activity in BCL-2 Overexpressing, Multidrug Resistant MCF-7 ADR Human Breast Cancer Cells", Int. J. Cancer, 98:463-469, (2002).
Clark et al., "Safety and Pharmacokinetics of the Dual Action Raf Kinase and Vascular Endothelial Growth Factor Rector Inhibitor, BAY43-9006, in Patients with Advanced Refractory Solid Tumors", Clin. Cancer Res. (2005)11:, 2005, p. 5472-p. 5480.
CN Office Action directed at application No. 200580026468.7 issued on Jun. 26, 2009, 6 pages.
CN Office Action directed at application No. 200710007097.9 issued on Mar. 6, 2009, 5 pages.
Cohen, et al., "Expression of Stem Cell Factor and c-kit in Human Neuroblastoma", Blood, 84(10):3465-3472 (1994).
Croom, et al., "Imatinib mesylate in the Treatment of Gastrointestinal Stromal Tumours", Drugs, 63(5), 2003, p. 513-p. 522.
Deplanque, et al., "Anti-Angiogenic Agents: Clinical Trial Design and Therapies in Development", European Journal of Cancer, 36, 2000, p. 1713-p. 1724.
Elisei et al., "Identification of a Novel Point Mutation in the RET Gene (Ala883Thr), Which Is Associated with Medullary Thyroid Carcinoma Phenotype Only in Homozygous Condition", The Journal of Clinical Endocrinology & Metabolism 89(11):5823-5827 (2004).
Erber et al., "Combined inhibition ofVEGF- and PDGF-signaling enforces tumor vessel regression by interfering with pericytemediated endothelial cell survival mechanisms", The FASEB Journal published online Dec. 4, 2003 (25 pages).
European Search Report for Application No. 06768437.3 dated Oct. 11, 2010 (10 pages).
European Search Report for Application No. 06833681.7 dated Nov. 24, 2010, 15 pages.
European Search Report for Appln No. 07806561.2 dated Jan. 19, 2011.
European Search Report for EP Appl. No. 06782407, Jul. 23, 2010.
European Search Report for EP Appl. No. 07743994.1 dated May 12, 2010.
Experimental and Molecular Therapeutices 30, Proceedings of the American Association for Cancer Research, vol. 47 (2006).
Folkman, et al., "Angiogenesis", The Journal of Biological Chemistry, 267(16), 1992, p. 10931-p. 10934.
Folkman, et al., "Clinical Applications of Research on Angiogenesis", The New England Journal of Medicine, 333(26), 1995, p. 1757-p. 1763.
Folkman, J., "New Perspective in Clinical Oncology From Angiogenesis Research", Eur J. Cancer. 32A(14), 1996, p. 2534-p. 2539.
Folkman, J., "What is the Evidence That Tumors are Angiogenesis Dendent?", Journal of the National Cancer Institute, 82(1), 1990, p. 4-p. 6.
Furitsu et al., "Stable medicinal compositions of quinolinecarboxamide derivative", Database Caplus Chemical Abstracts Service, Columbus, Ohio, US, 2006, XP002520305.
Furitsu, et al., "Identification of Mutations in the Coding Sequence of the Proto-Oncogene c-kit in a Human Mast Cell Leukemia Cell Line Causing Ligand-Indendent Activation of c-kit Product", J. Clin. Invest. 92, 1993, p. 1736-p. 1744.
Furuta, et al., "Synthesis and Biological Evaluation of Selective Inhibitors of PDGF Rector Auto Phosphorylation", Pharmaceutical Research Laboratories, Kirin Brewery Co., Ltd. Takasaki, Gunma, Japan.

(56) References Cited

OTHER PUBLICATIONS

Gall-lstok, et al., "Abstract of Acta Chimica Hungarica", Inst. Exp. Med., Hung. Avad. Svi., Budapest, 1983, p. 112(2)-p. 241-7.

Gardner et al., "In Vitro Activity of Sorghum-Selective Fluorophenyl Urea Herbicides", Pesticide Biochemistry and Physiology, 24(3):285-297, (1985).

Gatzemeier et al., "Phase III Comparative Study of High-Dose Cisplatin Versus a Combination of Paclitaxel and Cisplatin in Patients With Advanced Non-Small-Cell Lung Cancer", Journal of Clinical Oncology 18(19):3390-3399 (2000).

Gerald B. Dermer, "Another anniversary for the war on cancer", Bio/Technology, vol. 12, 1994, p. 320.

Giles, F., "The Vascular Endothelial Growth Factor (VEGF) Signaling Pathway: A Therapeutic Target in Patients with Hematologic Malignancies", The Oncologists 6(supp15):32-39 (2001).

Golkar, et al., "Mastocytosis", Lancet, 349, 1997, p. 1379-p. 1385.

Gould et al., International Journal of Pharmaceutics, Elsevier, BV, NL, vol. 33, No. 1-3, Nov. 1, 1986, p. 201-p. 217, XP025813036.

Haller, D., "Chemotherapy for Advanced Pancreatic Cancer", Int. J. Radiation Oncology Biol. Phys., 56(4): Supplement, pp. 16-23 (2003).

Hamel, et al., "The Road Less Travelled: c-kit and Stem Cell Factor", Journal of Neuro-Oncology, 35, 1997, p. 327-p. 333.

Hannequin et al., "Novel 4-Anilinoquinazolines with C-7 Basic Side Chains: Design and Structure Activity Relationship of a Series of Potent, Orally Active, VEGF Receptor Tyrosine Kinase Inhibitors", Journal of Medicine Chemistry 45:1300-1312 (2002).

Hattori et al., "Immunohistochemical Detection of K-sam Protein in Stomach Cancer", Clinical Cancer Research, 2:1373-1381 (1996).

Hayek, et al., "An In Vivo Model for Study of the Angiogenic Effects of Basic Fibroblast Growth Factor", Biochemical and Biophysical Research Communications, 147(2), 1987, p. 876-p. 880.

Haymo et al., "Pericytes in experimental MDA-MB231 tumor angiogenesis", Histochemistry and Cell Biology, 117(6):527-534 (2002).

Heinrich et al., "Inhibition of c-kit receptor tyrosine kinase activity by STI 571, a selective tyrosine kinase inhibitor", Hematopoeisis, Blood 96(3):925-932 (2000).

Heinrich et al., "Inhibition of KIT Tyrosine Kinase Activity: A Novel Molecular Approach to the Treatment of KIT-Positive Malignancies", Journal of Oncology 20(6):1692-1703 (2002).

Hibi, et al., "Coexpression of the Stem Cell Factor and the c-kit Genes in Small-Cell Lung Cancer", Oncogene, 6, 1991, p. 2291-p. 2296.

Hines, et al., "Coexpression of the c-kit and Stem Cell Factor Genes in Breast Carcinomas", Cell Growth & Differentiation, 6, 1995, p. 769-p. 779.

Hogaboam, et al."Novel Role of Transmembrane SCF for Mast Cell Activation and Eotaxin Production in Mast Cell-Fibroblast Interactions", The Journal of Immunology, 160, 1998, p. 6166-p. 6171.

Hurwitz et al., "Bevacizumab plus Irinotecan, Fluorouracil, and Leucovorin for Metastatic Colorectal Cancer", The New England Journal of Medicine, 350(23):2335-2342 (2004).

Ikeda, et al., "Changes in Phenotype and Proliferative Potential of Human Acute Myeloblastic Leukemia Cells in Culture with Stem Cell Factor", Experimental Hematology, 21, 1993, p. 1686-p. 1694.

Ikeda, et al., "Expression and Functional Role of the Proto-Oncogene c-kit in Acute Myeloblastic Leukemia Cells", Blood, 78(11), 1991, p. 2962-p. 2968.

Inai et al., "Inhibition of Vascular Endothelial Growth Factor (VEGF) Signaling in Cancer Causes Loss of Endothelial Fenestrations, Regression of Tumor Vessels, and Appearance of Basement Membrane Ghosts", American J. of Pathol. 165(1): 35-52 (2004).

Inoue et al., "Molecular Target Therapy Targeting Angiogenesis Pathways", The Nishinihon J. Urol., 66:425-432 (2004).

International Search Report issued for related PCT application PCT/JP01/09221, Jan. 15, 2002.

International Search Report issued for related PCT application PCT/JP2004/003087, Jul. 13, 2004.

ISR (PCT/JP2006/315563) dated Sep. 5, 2006.

ISR (PCT/JP2006/315698) dated Oct. 17, 2006.

ISR (PCT/JP2006/322514) dated Jan. 23, 2007.

ISR (PCT/JP2006/323881) dated Jan. 23, 2007.

ISR (PCT/JP2007/060560) dated Sep. 11, 2007.

ISR (PCT/JP2007/063525) dated Sep. 4, 2007.

ISR (PCT/JP2007/067088) dated Nov. 20, 2007.

ISR (PCT/JP2008/051024) dated Apr. 1, 2008.

ISR (PCT/JP2008/051697) dated Mar. 4, 2008.

ISR (PCT/JP2008/070321) dated Jan. 20, 2009.

ISR (PCT/JP2009/051244) dated Mar. 24, 2009.

Itoh et al., "Preferential Alternative Splicing in Cancer Generates a K-sam Messenger RNA with Higher Transforming Activity", Cancer Research 54: 3237-3241(2002).

J. Haleblian, Characterization of Habits and Crystalline Modification of Solids and Their Pharmaceutical Applications, "Journal of Pharmaceutical Sciences", 64(8):1269-1288 (1975).

Jakeman, et al., "Developmental Expression of Binding Sites and Messenger Ribonucleic Acid for Vascular Endothelial Growth Factor Suggests a Role for This Protein in Vasculogenesis and Angiogenesis", Endocrinology, 133(2), 1993, p. 848-p. 859.

Japanese Office Action for Application No. 2005-516605, Jun. 1, 2010 (with partial translation).

Jhiang, S., "The RET proto-oncogene in human cancers", Oncogene 19:5590-5597 (2000).

Jimenez et al., "Pheochromocytoma and Medullary Thyroid Carcinoma:A New Genotype-Phenotype Correlation of the RET Protooncogene 891 Germline Mutation", The Journal of Clinical Endocrinology & Metabolism 89(8):4142-4145 (2004).

Johnson et al., "Paclitaxel Plus Carboplatin in Advanced Non-Small-Cell Lung Cancer: A Phase II Trial", Journal of Clinical Oncology 14(7):2054-2060 (1996).

JP Allowance directed at application No. P2005-515330 issued on Apr. 21, 2009, 2 pages.

Jung et al., "Effects of combination anti-vascular endothelial growth factor receptor and anti-epidermal growth factor receptor therapies on the growth of gastric cancer in a nude mouse model", European Journal of Cancer, 38:1133-1140 (2002).

Juurikivi et al., "Inhibition of c-kit tyrosine kinase by imatinib mesylate induces apoptosis in mast cells in rheumatoid synovia: a potential approach to the treatment of arthritis", Ann. Rheum. Dis., 64:1126-1131 (2005).

Kanakura, et al., "Expression, Function and Activation of the Proto-Oncogene c-kit Product in Human Leukemia Cells", Leukemia and Lymphorma, 10, 1993, p. 35-p. 41.

Karl Nocka, et al., "Expression of c-kit gene products in known cellular targets of W mutations in normal and W mutant mice-evidence for an impaired c-kit kinase mutant mice", Genes & Development, Cold Spring Harbor Laboratory Press, 3:816-826, (1989).

Kashuk et al., "Phenotype-genotype correlation in Hirschsprung disease is illuminated by comparative analysis of the RET protein sequence", PNAS 102(25):8949-8954 (2005).

Kay, et al., "Eosinophils and Eosinophil-Associated Cytokines in Allergic Inflammation", Int. Arch. Allergy Immunol 113, 1997, p. 196-p. 199.

Kelly et al., "Randomized Phase III Trial of Paclitaxel Plus Carboplatin Versus Vinorelbine Plus Cisplatin in the Treatment of Patients With Advanced Non-Small-Cell Lung Cancer: A Southwest Oncology Group Trial", Journal of Clinical Oncology 19(13):3210-3218 (2001).

Kim et al., "A Phase II Study of Irinotecan Plus Cisplatin for Patients With Advanced Stage IIIB or IV NSCLC Previously Treated With Nonplatinum-Based Chemotherapy", American Cancer Socieity, pp. 799-805 (2006).

Kim et al., "An Orally Administered Multitarget Tyrosine Kinase Inhibitor, SU11248, Is a Novel Potent Inhibitor of Thyroid Oncogenic RET/Papillary Thyroid Cancer Kinases", The Journal of Clinical Endocrinology & Metabolism 91(10):4070-4075 (2006).

Kitamura, et al., "Regulation of Development, Survival and Neoplastic Growth of Mast Cells through the c-kit Rector", Int Arch Allergy Immunol., 107, 1995, p. 54-p. 56.

Kolibaba, et al., "Protein Tyrosine Kinases and Cancer", Biochimica et Biophysica Acta, 1333, 1997, p. F217-p. F248.

Kotva, et al., "Substances with Antineoplastic Activity, LIII. N-(δ-(4-Pyrrolo[2,3-d]Pyrimidinylthio)Valeryl]} Amino Acids and Analo-

(56) References Cited

OTHER PUBLICATIONS gous Derivatives of Di-and Triglycine", Collection Czechoslov. Chem. Commun.38, 1973, p. 1438-p. 1444.
KR Office Action directed at application No. 10-2006-7013993 issued on Jul. 31, 2007 (with English translation), 9 pages.
Lasota, et al., "Mutations in Exons 9 and 13 of KIT Gene Are Rare Events in Gastrointestinal Stromal Tumors", American Journal of Pathology, 157(4), 2000, p. 1091-p. 1095.
Lesueur et al., "Polymorphisms in RET and Its Coreceptors and Ligands as Genetic Modifiers of Multiple Endocrine Neoplasia Type 2A", Cancer Research 66(2):1177-1180 (2006).
Lev et al., "A Specific Combination of Substrates is Involved in Signal Transduction by the Kit-Encoded Rector", The EMBO Journal,10(3), 1991, p. 647-p. 654.
Li et al., "Abrogation of c-kit/Steel factor-dendent tumorigenesis by kinase defective mutants of the c-kit rector: c-kit kinase defective mutants as candidate tools for cancer gene therapy, Cancer Research vol. 56", Oct. 1, 1996, p. 4343-p. 4346, XP002522473.
Lin et al., "The Vascular Endothelias Growth Factor Receptor Tyrosine Kinase Inhibitor K787/ZK222584 Inhibits Growth and Migration of Mutiple Myeloma Cells in the Bone Marrow Microenvironment", Cancer Research, 62:5019-5026 (2002).
Logie et al., "Activating mutations of the tyrosine kinase receptor FGFR3 are associated with benign skin tumors in mice and humans", Human Molecular Genetics, 14(9):1153-1160 (2005).
Longley, et al., "Altered Metabolism of Mast-Cell Growth Factor (c-kit Ligand) in Cutaneous Mastocytosis", The New England Journal of Medicine, 328(18), 1993, p. 1302-p. 1307.
Longley, et al., "Classes of c-Kit activating mutations: proposed mechanisms of action and implications for disease classification and therapy", Leukemia Res., 25:571-576, (2001).
Longley, et al., "Somatic c-KIT Activating Mutation in Urticaria Pigmentosa and Aggressive Mastocytosis: Establishment of Clonality in a Human Mast Cell Neoplasm", Nature Genetics, 12, 1996, p. 312-p. 314.
Lukacs, et al., "Stem Cell Factor (c-kit Ligand) Influences Eosinophil Recruitment and Histamine Levels in Allergic Airway Inflammation", The Journal of Immunology, 156, 1996, p. 3945-p. 3951.
Matsui et al., "E7080 (ER-203492-00), a Novel VEGF Rector Tyrosine Kinase Inhibitor-I. Characterization as an Angiogenesis Inhibitor.", Abstract # 51, AACR, Toronto, Canada, Apr. 5-9, 2003.
Matsui et al., "E7080, a novel inhibitor that targets multiple kinases, has potent antitumor activities against stem cell factor producing human small cell lung cancer H146, based on angionenesis inhibition", Int. J. Cancer 122:664-671 (2008).
Matsui et al., "E7080, a novel multi-rector Tyrosine Kinase Inhibitor, inhibited in vitro / in vivo VEGF- and SCF-driven angiogenesis SCLC cell line", Matsui et al., Abstract #146, EORTC-NCI-AACR, Geneva, Switzerland, Sep. 28-Oct. 1, 2004.
Matsui et al., "Quantitative analysis of the profile of tumor vessels may be useful as predictive biomarkers for E7080", Abstract #4631, 98th AACR annual meeting, Los Angeles, CA,, Apr. 14-18, 2007.
Matsui et al., "VEGFRs inhibitor E7080 inhibits lymph node metastasis of human breast carcinoma, by preventing murine lymphatic endothelial cells from lymphangiogenesis.", Abstract # PD12-8, 18th EORTC-NCI-AACR symposium on "Molecular Targets and Cancer Therapeutics", Prague, Czech rublic, Nov. 7-10, 2006.
Matsui et al., "146 E7080, a novel multi-targeted tyrosine kinase inhibitor, exhibits anti-angiogenic activity via inhibition of KIT signaling in a small cell lung cancer xenograft model", European Journal of Cancer, Supplement Pergamon, Oxford, GB XP004639590 abstract.
McCarty et al., "ZD6474, a vascular endothelial growth factor receptor tyrosine kinase inhibitor with additional activity against epidermal growth factor receptor tyrosine kinase, inhibits orthotopic growth and angiogenesis of gastric cancer", Molecular Cancer Therapeutics, 3(9):1041-1048 (2004).

McCulloch et al., "Astragalus-Based Chinese Herbs and Platinum-Based Chemotherapy for Advanced Non-Small-Cell Lung Cancer: Meta-Analysis of Randomized Trials", Journal of Clinical Oncology 24(3):419-430 (2006).
Meltzer, E.O., "The Pharmacological Basis for the Treatment of Perennial Allergic Rhinitis and Non-Allergic Rhinitis with Topical Corticosteroids", Allergy, 52, 1997, p. 33-p. 40.
Mendel et al., "In Vivo Antitumor Activity of SU11248, a Novel Tyrosine Kinase Inhibitor Targeting Vascular Endothelial Growth Factor and Platelet-derived Growth Factor Rectors: Determination of a Pharmacokinetic/Pharmacodynamic Relationship" Clin. Cancer Res., 9: 327-337, (2003).
Metcalf, et al., "Lineage Commitment in the Progeny of Murine Hematopoietic Prrogenitor Cells: Influence of Thrombopoietin and Interleukin 5", Proc. Nat'l Acad. Sci. USA, 95, 1998, p. 6408-p. 6412.
Metcalfe, D., "Classification and Diagnosis of Mastocytosis: Current Status", J. Invest. Dermatol, 96, 1991, p. 2S-p. 4S.
Metcalfe, et al., "Mast Cells", Physiological Reviews, 77(4), 1997, p. 1033-p. 1079.
Micke et al., "Characterization of c-kit expression in small cell lung cancer: prognostic and therapeutic implications", Clinical Cancer Res. 9:188-194(2003).
Miller et al., "Paclitaxel plus Bevacizumab versus Paclitaxel Alone for Metastatic Breast Cancer", The New England Journal of Medicine, 357:2666-76 (2007).
Miyazaki et al., "Synthesis, Structure and Biological Activity Relationship of E7080 and its Derivatives as Novel and Potent Antiangiogenic Protein Tyrosine Kinase Inhibitors Including the VEGF Rectors, FGFR1 Rector and PDGF Rector." Abstract B-15, AIMECS03, Kyoto, Japan, Oct. 14-17, 2003.
Miyazaki et al., Synthesis, Structure and Biological Activity Relationship of . . . PDGF Receptor, AIMECS 03, 5th AFMC International Medicinal Chem. Symposium, Oct. 2003, Kyoto Japan, 1 page.
Mologni et al., "Inhibition of RET tyrosine kinase by SU5416", Journal of Mol. Endo., 37:199-212 (2006).
Morgan et al., "Dynamic Contrast-Enhanced Magnetic Resonance Imaging As a Biomarker for the Pharmacological Response of PTK787/ZK 222584, an Inhibitor of the Vascular Endothelial Growth Factor Receptor Tyrosine Kinases, in Patients With Advanced Colorectal Cancer and Liver Metastases: Results From Two Phase I Studies", Journal of Oncology 21(21):3955-3964 (2003).
Morikawa et al., Angiogenesis and Pericytes, Putative Positive Function of Pericytes in Angiogenesis, Cell, 13 pages, with English translation, (2005).
Morris et al., "An integrated approach to the selection of optimal salt form for a new drug candidate," Internarional Journal of Pharmaceutics, Elsevier, BV, NL, vol. 105, No. 3, May 9, 1994, p. 209-p. 217, XP023724810.
Myers, et al., "The Praration and SAR of 4-(Anilino), 4-(Phenoxy), and 4-(Thiophenoxy)-Quinazolines: Inhibitors of p561ck and EGF-R Tyrosine Kinase Activity", Bioorgan. & Med. Chem. Letters, 7, 1997, p. 417-p. 420.
Naclerio, et al., "Rhinitis and Inhalant Allergens", JAMA, 278(22), 1997, p. 1842-p. 1848.
Nagata, et al., "Elevated Expression of the Proto-Oncogene c-kit in Patients with Mastocytosis", Leukemia, 12, 1998, p. 175-p. 181.
Nakamura et al., "E7080 (ER-203492-00), a Novel VEGF Rector Tyrosine Kinase Inhibitor-II. Effects on Growth of Human Tumor Xenografts and Life Span of Mice in Colon 38 Orthotopic Transplantation Model." Abstract # 52, AACR, Toronto, Canada, Apr. 5-9, 2003.
Naski et al., "Graded activation of fibroblast growth factor receptor 3 by mutations causing achondroplasia and thanatophoric dysplasia", Nature Genetics 13:233-237 (1996).
Natali, et al., "Breast Cancer is Associated with Loss of the c-kit Oncogene Product", Int. J. Cancer, 52, 1992, p. 713-p. 717.
Nugiel et al., "Synthesis and Evaluation of Indenopyrazoles as Cyclin-Dependent Kinase Inhibitors. 2. Probing the Indeno Ring Substituent Pattern", Journal of Medical Chemistry, 45(24):5224-5232, (2002).

(56) References Cited

OTHER PUBLICATIONS

Ocqueteau et al., "Expression of the CD117 Antigen (C-Kit) on Normal and Myelomatous Plasma cells", British Journal of Haematology, 95:489-493 (1996).

Office Action dated Oct. 30, 2009 for EP Appl. No. 04719054.1.

Ohe et al., "Randomized phase III study of cisplatin plus irinotecan versus carboplatin plus paclitaxel, cisplatin plus gemcitabine, and cisplatin plus vinorelbine for advanced non-small-cell lung cancer: Four-Arm Cooperative Study in Japan", Annals of Oncology 18:317-323 (2007).

Okayama, et al., "Activation of Eosinophils with Cytokines Produced by Lung Mast Cells", Int Arch Allergy Immunol.114:(suppl 1), 1997, p. 75-p. 77.

Okayama, et al., "Human Lung Mast Cells are Enriched in the Capacity to Produce Granulocyte-Macrophage Colony-Stimulating Factor in Response to IgE-Dendent Stimulation", Eur. J. Immunol 28, 1998, p. 708-p. 715.

Olaso et al., "DDR2 receptor promotes MMP-2-mediated proliferation and invasion by hepatic stellate cells", The Journal of Clinical Investigation, 108( 9):1369-1378 (2001).

Ozols et al., "Phase III Trial of Carboplatin and Paclitaxel Compared With Cisplatin and Paclitaxel in Patients With Optimally Resected Stage III Ovarian Cancer: A Gynecologic Oncology Group Study", Journal of Oncology 21(17):3194-3200 (2003).

Paterson et al., "Preclinical studies of fibroblast growth factor receptor 3 as a therapeutic target in multiple myeloma", Blackwell Publishing Ltd, British Journal of Haematology, 124: 595-603 (2004).

Paz and Zhu, "Development of Angiogenesis Inhibitors to Vascular Endothelial Growth Factor Receptor 2. Current Status and Future Perspectiv", Frontiers in Bioscience 10:1415-1439 (2005).

Plowright et al., "Ectopic expression of fibroblast growth factor receptor 3 promotes myeloma cell proliferation and prevents apoptosis" Neoplasia, Blood, 95(3): 992-998 (2000).

Pritzker, "Cancer Biomarkers: Easier Said Than Done", Clinical Chemistry 48(8):1147-1150 (2002).

R. Ian Freshney, Alan R. Liss, "Culture of Animal Cells, A Manual of Basic Technique", New York, 1983, p. 4.

Raimondo et al., "Angiogenic factors in multiple myeloma: higher levels in bone marrow than in peripheral blood", Haematologica, 85:800-805 (2000).

Salmon et al., "Anti-Angiogenic Treatment of Gastrointestinal Malignancies", New Drugs, Cancer Investigation 23:712-726 (2005).

Sandler et al., "Phase III Trial of Gemcitabine Plus Cisplatin Versus Cisplatin Alone in Patients With Locally Advanced or Metastatic Non-Small-Cell Lung Cancer", Journal of Clinical Oncology 18(1):122-130 (2000).

Santoro et al., "Drug Insight: small-molecule inhibitors of protein kinases in the treatment of thyroid cancer", Nature Clinical Practice Endocrinology & Metabolism 2(1):42-52 (2006).

Santoro et al., "Minireview: RET: Normal and Abnormal Functions", Endocrinology 145(12):5448-5451 (2004).

Scheijen et al."Tryosine Kinase Oncogenes in Normal Hematopoiesis and Hematological Disease", Oncogene, 21, 2002, p. 3314-p. 3333.

Sekido, et al., "Preferential Expression of c-kit Protooncogene Transcripts in Small Cell Lung Cancer", Cancer Research, 51, 1991, p. 2416-p. 2418.

Shiang et al., "Mutations in the Transmembrane Domain of FGFR3 Cause the Most Common Genetic Form of Dwarfism, Achondroplasia", Cell 78:335-342 (1994).

Shimizu et al., "Orally active anti-proliferation agents: novel diphenylamine derivatives as FGF-R2 autophosphorylation inhibitors", Bioorganic & Medicinal Chem. Letters 14:875-879 (2004).

Spacey, et al., "Indolocarbazoles, Potent and Selective Inhibitors of Platelet-Derived Growth Factor Rector Autophosphorylation", Biochemical Pharmacology, 55:261-271, (1998).

Strohmeyer, et al., "Expression of the hst-1 and c-kit Protoonocogenes in Human Testicular Germ Cell Tumors", Cancer Research, 51, 1991, p. 1811-p. 1816.

Taguchi et al., "A novel orally active inhibitor of VEGF rector tyrosine kinases KRN951: Anti-angiogenic and anti-tumor activity against human solid tumors.", Taguchi E et al., Proceedings of the AACR annual meeting., vol. 45, Mar. 2004, p. 595, XP002536608.

Takahashi et al., "A case of inoperable scirrhous gastric cancer that responded remarkably to a combination of TS-1 +paclitaxel and showed complete loss of ascites", JP Journal of Cancer and Chemotherapy, 31(7):1093-1095 (2004).

Takano et al., "Thermal recording materials with improved background stability", Database CA(Online) Chemical Abstracts Service, Columbus, Ohio, US, Feb. 20, 1996, XP002443195.

Takeda et al., "AZD2171 shows potent anti-tumor activity against gastric cancer expressing variant K-SAM/FGFR2", Proceeding of the American Association for Cancer Research, 47:890 (2006) #3785.

Tan et al., "Randomized study of vinorelbine-gemcitabine versus vinorelbine-carboplatin in patients with advanced non-small cell lung cancer", Lung Cancer, 49:233-240 (2005).

Taniguchi, et al., "Effect of c-kit Mutation on Prognosis of Gastrointestinal Stromal Tumors", Cancer Research, 59, 1999, p. 4297-p. 4300.

Thomas et al., "The Eosinophil and its Role in Asthma", Gen. Pharmac. 27(4), 1996, p. 593-p. 597.

Tian, et al., "Activating c-kit Gene Mutations in Human Germ Cell Tumors", American Journal of Pathology, 154(6), 1999, p. 1643-p. 1647.

Tonary, et al., "Lack of Expression of c-KIT in Ovarian Cancers is Associated with Poor Prognosis", Int. J. Cancer (Pred. Oncol) 89, 2000, p. 242-p. 250.

Tong et al., "Vascular Normalization by Vascular Endothelial Growth Factor Receptor 2 Blockade Induces a Pressure Gradient Across the Vasculature and Improves Drug Penetration in Tumors", Cancer Research 64:3731-3736 (2004).

Traxler et al., "AEE788: A Dual Family Epidermal Growth Factor Receptor/ErbB2 and Vascular Endothelial Growth Factor Receptor Tyrosine Kinase Inhibitor with Antitumor and Anti-angiogenic Activity", Cancer Research 64:4931-4941 (2004).

Trisha Gura, "Cancer Models Systems for Identifying new drugs are often faulty", Science, vol. 278, Nov. 7, 1997, p. 1041-p. 1042.

Trudel et al., "Inhibition of fibroblast growth factor receptor 3 induces differentiation and apoptosis in t(4;14) myeloma", Neoplasia, Blood, 103(9): 3521-3528 (2004).

Trudel et al., "CHIR-258, a novel, multi-targeted tyrosine kinase inhibitor for the potential treatment of t(4;14) multiple myeloma", Neoplasia, Blood 105(7):2941-2948 (2005).

Ueda et al., "Deletion of the Carboxyl-Terminal Exons of K-sam/FGFR2 by Short omologymediated Recombination, Generating Preferential Expression of Specific Messenger RNAs", Cancer Research, 59:6080-6086 (1999).

US Office Action directed at U.S. Appl. No. 10/577,531 issued on Sep. 23, 2008, 17 pages.

US Office Action directed at U.S. Appl. No. 10/797,903 issued on Aug. 20, 2009, 12 pages.

US Office Action directed at U.S. Appl. No. 10/797,903 issued on Dec. 11, 2007.

US Office Action directed at U.S. Appl. No. 11/347,749 issued on Feb. 9, 2009, 6 pages.

US Office Action directed at U.S. Appl. No. 11/997,543 issued May 19, 2011.

US Office Action directed at U.S. Appl. No. 11/997,719 issued on Sep. 3, 2010, 10 pages.

US Office Action directed at U.S. Appl. No. 12/092,539 issued on Jan. 7, 2011.

US Office Action directed at U.S. Appl. No. 12/094,492 issued on Mar. 24, 2011, 16 pages.

US Office Action directed at U.S. Appl. No. 12/301,353 issued on Jan. 24, 2011, 42 pages.

US Office Action directed at U.S. Appl. No. 12/864,817 issued on May 19, 2011.

Van Oers et al., "A Simple and Fast Method for the Simultaneous Detection of Nine Fibroblast Growth Factor Receptor 3Mutations in Bladder Cancer and Voided Urine", Clin Cancer Res 11(21):7743-7748 (2005).

(56) References Cited

OTHER PUBLICATIONS

Vippagunta et al., "Crystalline solids", Advanced Drug Delivery Reviews 48:3-26 (2001).
Vogel et al., "Sensing extracellular matrix: An update on discoidin domain receptor function", Cellular Signalling 18:1108-1116 (2006).
Wakeling, et al., ZD1839 (Iressa): An Orally Active Inhibitor of Epidermal Growth Factor Signalling with Potential for Cancer Therapy, Cancer Res.,62:5749-5754 ( 2002).
Wakui , "Chemotherapy of scirrhous gastric cancer ", JP Journal of Cancer and Chemotherapy, 21(14): 2398-2406 (1994).
Wang and Schwabacher, "A Convenient Set of Bidentate Pyridine Ligands for Combinatorial Synthesis", Tetrahedron Lett.40, 1999, p. 4779-p. 4782.
Wang et al., "Phase II study of gemcitabine and carboplatin in patients with advanced non-small-cell lung cancer", Cancer Chemother Pharmacol, 60:601-607 (2007).
Wang, et al., "The Expression of the Proto-Oncogene C-Kit in the Blast Cells of Acute Myeloblastic Leukemia", Leukemia, 3(10), 1989, p. 699-p. 702.
Wedge et al., "AZD2171: A Highly Potent, Orally Bioavailable, Vascular Endothelial Growth Factor Rector-2 Tyrosine Kinase Inhibitor for the Treatment of Cancer", Cancer Res., vol. 65(10), p. 4389-4400, 2005.
Werner et al., "Gastric adenocarcinoma: pathormorphology and molecular pathology", J. Cancer Res. Clin. Oncol. 127:207-216 (2001).
Willett et al., "Direct evidence that the VEGF-specific antibody bevacizumab has antivascular effects in human rectal cancer", Nature Medicine 10(2):145-147 (2004).
WO IPRP directed at application No. PCT/JP2004/003087 issued on Feb. 23, 2006, 5 pages.
WO IPRP directed at application No. PCT/JP2006/312487 issued on Jan. 10, 2008, 7 pages.
Wozniak et al., "Randomized Trial Comparing Cisplatin With Cisplathn Plus Vinorelbine in the Treatment of Advanced Non-Small•Cell Lung. Cancer: A Southwest Oncology Group Study", Journal of Clinical Oncology 16(7):2459-2465 (1998).
Yamada et al., "New Technique for Staining", Monthly Medical Technology, (13 pages).
Yamamoto et al., "A Novel VEGF Receptor Tyrosine Kinase Inhibitor-III. Significant prolongation of life span in mice transplanted with human ovarian carcinoma based on inhibition of VEGF signaling", Abstract # 50, AACR, Toronto, Canada, Apr. 5-9, 2003.
Yamamoto et al., "E7080 a novel multitargeted tyrosine kinase inhibitor, has direct anti-tumor activity via inhibition of KIT signaling in small cell lung cancer", Yamamoto et al., Abstract #4636, AACR, Orlando, FL, Mar. 27-31, 2004.
Yamamoto et al., "E7080, an oral multi-targeted tyrosine kinase inhibitor, has direct anti-tumor efficacy via inhibition of KIT signaling in gastrointestinal stromal tumor (GIST)" Abstract #40358, 97th annual meeting AACR, Washington, DC., Apr. 1-5, 2006.
Yanagihara et al., "Development and biological analysis of peritoneal metastasis mouse models for human scirrhous stomach cancer", Cancer Sci, 96(6):323-332 (2005).
Zhang et al., "Overexpression of Platelet-Derived Growth Factor Receptor α in Endothelial Cells of Hepatocellular Carcinoma Associated with High Metastatic Potential", Clinical Cancer Research 11:8557-8563 (2005).
Zhu et al., "Fibroblast growth factor receptor 3 inhibition by short hairpin RNAs leads to apoptosis in multiple myeloma", Mol Cancer Ther 4(5):787-798 (2005).
Zhu et al., Molecular Targets for Therapy (MTT), "Inhibition of human leukemia in an animal . . . activity", Leukemia 17:604-611 (2003).
Zieger et al., "Role of Activating Fibroblast Growth Factor Receptor 3 Mutations in the Development of Bladder Tumors", Clin Cancer Res 11(21):7709-7719 (2005).
Search report directed at EP application No. 03791389.4, issued on Jul. 7, 2011, 3 pages.

Chinese Office Action directed at application No. 200880003336.6, issued on May 24, 2011, pages (with English Translation).
European Search Report for Application No. 10015141.4 dated Sep. 9, 2011.
US Office Action directed a U.S. Appl. No. 12/523,495 issued on Sep. 30, 2011.
Zhou et al., "Correlation Research on VEGF Testing in Primary Gastric Cancer and Clinical Pathology Factor", Journal of Practical Oncology, 20(2):103-105 (2006) with English translation.
European Search Report for Application No. 04807580.8 dated Apr. 18, 2011 (9 pages).
European Search Report for Application No. 06767145.3 dated May 23, 2011 (7 pages).
Yu, Lian, "Amorphous pharmaceutical solids: preparation, characterization and stabilization", Adv. Drug Delivery Reviews, Elsevier, Amsterdam, NL, 48(1):27-42 (2001).
Ko et al., "Stomach Cancer", Cancer supportive care.com, published online Feb. 2003, pp. 1-4.
Kleespies et al., Tyrosine kinase inhibitors and gemcitabine: New treatment options in pancreatic cancer?, Drug Resistance Updates 9:1-19 (2006).
US Office Action directed at U.S. Appl. No. 12/439,339 issued Nov. 14, 2011.
US Office Action directed a U.S. Appl. No. 12/523,495 issued on Sep. 27, 2011.
Final Office Action for U.S. Appl. No. 12/523,495 dated Dec. 27, 2011.
Final Office Action for U.S. Appl. No. 11/997,719 issued on Apr. 6, 2011.
Final Office Action for U.S. Appl. No. 11/997,543 dated Nov. 9, 2011.
Office Action for U.S. Appl. No. 12/524,754 dated Dec. 19, 2011.
Zimmermann et al., "Potent and Selective Inhibitors of the ABL-Kinase:Phenylamino-Pyrimidine (PAP) Derivatives", Bioorganic and Medicinal Chemistry Letters., 7(2):187-192, 1997.
Krystal et al., "Indolinone Tyrosine Kinase Inhibitors Block Kit Activation and Growth of Small Cell Lung Cancer Cells", Cancer Research., 61, 3660-3668, 2001.
Sun et al., "Synthesis and Biological Evaluations of 3-Substituted Indolin-2-ones: A Novel Class of Tyrosine Kinase Inhibitors That Exhibit Selectively toward Particular Receptor Tyrosine Kinases", Journal of Medicinal Chemistry, 41: 2588-2603, 1998.
Sun et al., "Design, Synthesis, and Evaluations of Substituted . . . Receptor Tyrosine Kinases", Journal of Medicinal Chemistry., 42: 5120-5130, 1999.
Abrams et al., "SU11248 Inhibits KIT and Platelet-derived Growth Factor Receptor Beta in Preclinical Models of Human Small Cell Lung Cancer", Molecular Cancer Therapeutics., 2: 471-478, 2003.
Sun et al., "Discovery of . . . Receptor Tyrosine Kinase", Journal of Medicinal Chemistry., 46: 1116-9, 2003.
Nakamura et al., "KRN633: A Selective inhibitor of vascular endothelial growth factor receptor-2 tyrosine kinase that suppresses tumor angiogenesis and growth", Molecular Cancer Therapeutics., 3: 1639-49, 2004.
Wood et al., "PTK787/ZK 222584, a Novel and Potent Inhibitor of Vascular Endothelial Growth Factor Receptor Tyrosine Kinases, Impairs Vascular Endothelial Growth Factor-Induced Responses and Tumor Growth after Oral Administration", Cancer Research., 60, 2178-2189, 2000.
Bold et al., "New Anilinophthalazines as a potent and Orally well absorbed Inhibitors of the VEGF Receptor Tyrosine Kinases Useful as Antagonists of Tumor-Driven Angiogenesis", Journal of Medicinal Chemistry., 43: 2310-23, 2000.
Wilhelm et al., "BAY 43-9006 Exhibits Broad Spectrum Oral Antitumor Activity and Targets the RAF/MEK/ERK Pathway and Receptor Tyrosine Kinases Involved in Tumor Progression and Angiogenesis", Cancer Research., 64, 7099-7109, 2004.
Bankston et al., "A Scaleable Synthesis of BAY 43-9006: A Potent Raf Kinase Inhibitor for the Treatment of Cancer", Organic Process Res Dev, 6, 777-81, 2002.
Yigitbasi et al., "Tumor Cell and Endothelial Cell Therapy of Oral Cancer by Dual Tyrosine Kinase Receptor Blockade", Cancer Research, 64, 7977-7984, 2004.

(56) References Cited

OTHER PUBLICATIONS

Wisniewski et al., "Characterization of Potent Inhibitors of the Bcr-Abl and the c-Kit Receptor Tyrosine Kinases", Cancer Research., 62, 4244-4255, 2002.
Hamby et al., "Structure-Activity Relationships for a Novel Series of Pyrido[2,3-d]pyrimidine Tyrosine Kinase Inhibitors", Journal of Medicinal Chemistry., 40, 2296-2303, 1997.
Corbin et al., "Sensitivity of oncogenic KIT mutants to the kinase inhibitors MLN518 and PD180970", Blood., 104, 3754-3757, 2004.
Pandey et al., "Identification of Orally Active, Potent, and Selective 4-Piperazinylquinazolines as Antagonists of the Platelet-Derived Growth Factor Receptor Tyrosine Kinase Family", Journal of Medicinal Chemistry., 45, 3772-3793, 2002.
Carter et al., "Inhibition of drug-resistant mutants of ABL, KIT and EGF receptor kinases", Proceedings of the National Academy of Sciences of the United States of America., 102, 11011-11016, 2005.
Huston et al., "Protein engineering of antibody binding sites: Recovery of specific activity in an anti-digoxin single-chain Fv analogue produced in *Escherichia coli*", Proc. Natl. Acad. Sci. USA 85: 5879-83, 1988.
Van Dijk et al. "Induction of Tumor-Cell Lysis by B-Specific Monoclonal Antibodies Recognizing Renal-Cell Carcinoma and CD3 Antigen", Int. J. Cancer 43: 344-9, 1989.
PCT/JP2006/322514 International Preliminary Report on Patentability issued on May 7, 2008.
PCT/JP2006/322516 International Search Report issued on Jan. 23, 2007.
PCT/JP2006/322516 International Preliminary Report on Patentability issued on May 7, 2008.
Australian Office Action for Application No. U2006309551 issued on Apr. 28, 2011.
Chinese Office Action for Application No. 200680041355.9 issued on Mar. 5, 2010 with English translation.
Chinese Response to Office Action for Application No. 200680041355.9 filed on Jul. 19, 2010 with English translation.
Chinese Office Action for Application No. 200680041355.9 issued on Aug. 24, 2010 with English translation.
Chinese Response to Office Action for Application No. 200680041355.9 filed on Nov. 8, 2010 with English translation.
European Office Action for Application No. 06832529.9 issued on Oct. 15, 2009.
European Response to Office Action for Application No. 06832529.9 filed on Apr. 22, 2010.
European Office Action for Application No. 06832529.9 issued on Sep. 12, 2011.
European Response to Office Action for Application No. 06832529.9 filed on Oct. 4, 2011.
EP Communication under Rule 71(3) EPC for Application No. 06832529.9 issued on Nov. 25, 2011.
Office Action for U.S. Appl. No. 12/092,539 issued on Oct. 29, 2010.
Office Action Response for U.S. Appl. No. 12/092,539 filed on Nov. 22, 2010.
Office Action Response for U.S. Appl. No. 12/092,539 filed on Mar. 11, 2011.
Final Office Action for U.S. Appl. No. 12/092,539 issued on May 9, 2011.
Final Office Action Response for U.S. Appl. No. 12/092,539 filed on Jun. 15, 2011.
Advisory Action for U.S. Appl. No. 12/092,539 issued on Jun. 28, 2011.
Australian Response to Office Action for Application No. 2006309551 filed on Jan. 21, 2012.
Australian Office Action for Application No. 2006309551 issued on Feb. 2, 2012.
Response to Office Action for Australian Application No. 2006309551 dated Mar. 30, 2012.
Office Action for CN 200980103218.7 dated Sep. 29, 2012 with English translation.
Examination Report for NZ Patent Application No. 598291 dated Oct. 15, 2012.
Response to Office Action for CN200880115011.7 dated Nov. 20, 2012 with English translation.
Office Action for U.S. Appl. No. 13/083,338 dated Nov. 23, 2012.
Response to Office Action for JP2011-527665 dated May 10, 2012 with English translation.
Explanation of Circumstances re Accelerated Examination filed for JP2011-527665 dated May 10, 2012 with English translation.
Office Action for IN 1571/CHENP/2007 dated Oct. 30, 2012.
Office Action for AU 2008325608 dated Nov. 24, 2012.
Office Action for EP 07743994.1 dated Oct. 10, 2012.
Response to Office Action for IL 200090 dated Dec. 23, 2012 (with English language translation).
European Search Report for EP 10809938.3 dated Jan. 2, 2013.
Office Action for CN 201080030508.6 dated Nov. 30, 2012 with English translation.
Response to Office Action for EP 08704376.6 dated Jan. 2, 2013.
Response to Office Action for EP 08846814.5 dated Jan. 3, 2013.
Office Action for U.S. Appl. No. 13/083,338 dated Jan. 3, 2013.
Clinical Trial: AMG 706 20040273 Thyroid Cancer Study, Stage 4 Cancer Treatments, Chat w/a Cancer Info Expert About Stage 4 Cancer Treatment Options. Www.CancerCenter.com, Jul. 2005.
Polverino et al., "AMG 706, an Oral, Multikinase Inhibitor that Selectively Targets Vascular Endothelial Growth Factor, Platelet-Derived Growth Factor, and Kit Receptors, Potently Inhibits Angiogenesis and Induces Regression in Tumor Xenografts", Cancer Research, 66(1):8715-8721, Sep. 1, 2006.
Office Action for IL 205512 dated Dec. 20, 2012 with English translation.
Response to Office Action for EP03791389.4 dated Dec. 20, 2012.
Communication from Israel Patent Office for IL 175363 dated Jan. 2, 2013 with English translation.
Notice of Allowance for U.S. Appl. No. 12/524,754 dated Jan. 18, 2013.
Amendment submitted for Korean Application No. 10-2009-7017694 dated Jan. 18, 2013 with English translation.
Response to Office Action for U.S. Appl. No. 13/322,961 dated Jan. 25, 2013.
Decision of Patent Grant for JP2008-516724 dated Jan. 22, 2013 with English translation.
Office Action for JP2008-556208 dated Jan. 22, 2013 with English translation.
International Preliminary Report on Patentability for PCT/JP2011/064430 dated Jan. 24, 2013.
Response to Office Action for Canadian Patent Application No. 2627598 dated Jan. 25, 2013.
Office Action for Australian Patent Application No. 2009210098 dated Jan. 30, 2013.
Response to Office Action for European Application No. 07743994.1 dated Feb. 8, 2013.
Request to amend specification for Australian Patent Application No. 2008325608 dated Feb. 15, 2013.
Response to Office Action for Chinese Patent Application No. 200780017371.9 dated Nov. 30, 2012.
European Search Report for EP 12195436.6 dated Feb. 21, 2013.
English language translation of Office Action dated Jan. 2, 2013 for Israel Patent Application No. 175363.
Amendment for New Zealand Patent Application No. 598291 dated Jan. 30, 2013.
Amendment for Chinese Patent Application No. 201080030508.6 dated Feb. 7, 2013 with English translation.
Response to Office Action for IL Patent Application No. 175363 dated Feb. 27, 2013.
Notice of Allowance for AU Application No. 2008325608 dated Feb. 27, 2013.
Notice of Allowance for U.S. Appl. No. 12/741,682 dated Feb. 19, 2013.
Response to Office Action for IL Application No. 205512 dated Mar. 14, 2013.
Communication (Notification on Defects in application) for IL Application No. 207089 dated Jan. 6, 2013.
Office Action from CN Patent Application No. 200880115011.7 dated Feb. 25, 2013.

(56) References Cited

OTHER PUBLICATIONS

Communication (Notice of Allowance) for CA Patent Application No. 2627598 dated Mar. 8, 2013.
Notice of Acceptance for NZ Application No. 598291 dated Feb. 15, 2013.
Kawano et al., "Presentation Abstract, Abstract No. 1619,—Combination of VEGFR inhibitor lenvatinib (E7080) and Met/EphB4 inhibitor golvatinib (E7050) overcomes VEGFR inhibitor—resistant I tumor vascular", Annual Meeting 2013, Walter E. Washington Convention Center, Washington, DC, Apr. 6-10, 2013.
Response to Office Action for CN Application No. 200980103218.7 dated Feb. 16, 2013.
Office Action for U.S. Appl. No. 13/624,278 dated Mar. 29, 2013.
Preliminary Amendment for U.S. Appl. No. 13/624,278 filed Sep. 21, 2012.
Response to Office Action for U.S. Appl. No. 13/083,338 filed Apr. 2, 2013.
CN200780032071.8 Office Action issued on Oct. 13, 2010 with English translation.
CN200780032071.8 Response to Office Action filed on Feb. 16, 2011 with English translation.
EP07806561.2 Office Actions issued on Jan. 19 and Feb. 7, 2011.
EP07806561.2 Response to Office Action filed on Aug. 9, 2011.
EP07806561.2 Office Action issued on Dec. 9, 2011.
Genitourinary Cancers, Prostate Cancer Genitourinary, http://www.merkmanuals.com/professional/print/sec17/ch241/ch241e.html Mar. 16, 2011.
Guo et al., "Expression of gastric cancer-associated MG7 antigen in gastric cancer, precancerous lesions and *H. pylori*-associated gastric diseases", Word J. Gastroenterol, 8(6):1009-1013 (2002).
IPRP (PCT/JP2007/067088) dated Mar. 3, 2009 with English translation.
Japanese Publication of Patent Application No. H11-322596 with English translation.
Japanese Patent Application No. 2006-230816 (English translation).
Leukemias, Hematology and Oncology, http://www.merkmanuals.com/professional/print/sec11/ch142/ch142a.html Mar. 16, 2011.
Santoro et al., "Molecular Mechanism of RET Activation in Human Cancer", Ann. N.Y. Acad Sci. 963:116-121 (2002).
Shibata et al., "Rapid Communication Association of Epstein-Barr Virus with Undifferentiated Gastric Carcinomas with Intense Lymphoid Infiltration", American Journal of Pahthology 139(3):469-473 (1991).
Thyroid Cancers, Endocrine and Metabolic Disorders, http://www.merkmanuals.com/professional/print/sec12/ch152/ch152j.html Mar. 16, 2011.
Wakui , "Chemotherapy of scirrhous gastric cancer", JP Journal of Cancer and Chemotherapy, 21(14): 2398-2406 (1994) English translation.
Response to the European Search Report for Euroepan Application No. 06782407 filed on Nov. 8, 2010.
Office Action issued for European Search Report for European Application No. 06782407 on Sep. 29, 2011.
Response to the Office Action for European Application No. 06782407 filed on Jan. 23, 2012.
Office Action issued for Japanese Application No. 2007-529565 issued on Dec. 13, 2011 with English translation.
Response to the Office Action issued for Japanese Application No. 2007-529565 filed on Feb. 3, 2012 with English full translation.
Office Action directed at Israel Application No. 207089 issued on Nov. 13, 2011 (with English translation).
Written Opinion of the International Searching Authority directed at PCT/JP2009/051244 issued on Mar. 24, 2009 (with English translation).
International Preliminary Report directed at PCT/JP2009/051244 issued on Aug. 31, 2010 (with English translation).
Israel Office Action directed at Appl. No. 205512 issued on Nov. 13, 2011 with English translation.
PCT/JP2008/070321 Written Opinion of the International Searching Authority issued on Jan. 20, 2009 with English translation.

PCT/JP2008/070321 International Preliminary Report on Patentability issued on May 11, 2010 with English translation.
Sanger et al., "DNA sequencing with chain-terminating inhibitors", Proc. Natl. Acad. Sci. USA 74: 5463 (1977).
Takahashi et al., "A Case of Inoperable Scirrhous Gastric Cancer that Responded Remarkably to a Combination . . . Loss of Ascites", Japanese Journal of Cancer and Chemotherapy, 31(7):1093-1095 (2004) (English translation only).
PCT/JP2008/051697 Written Opinion of the International Searching Authority issued on Mar. 4, 2008.
PCT/JP2008/051697 International Preliminary Report on Patentability issued on Aug. 4, 2009.
CN200880003336.6 Response to Office Action filed on Oct. 8, 2011.
Israel 200090 Office Actions issued on Jun. 22, 2010.
Israel 200090 Response to Office Action filed on Oct. 12, 2010.
Office Action issued for EP application No. 07806561.2 on Dec. 9, 2011.
Office Action issued for U.S. Appl. No. 10/797,903 on Apr. 1, 2010.
Office Action issued for U.S. Appl. No. 10/797,903 on Sep. 1, 2010.
Office Action (Decision to refuse) issued for EP 04807580.8 on Oct. 25, 2011.
Forbes R T et al.,International Journal of Pharmaceutics, Elsevier Science BV, vol. 126, Jun. 1, 1995, p. 199-208.
Ernst Mutschler et al., Arzneimittel-Wirkungen Lehrbuch Der Pharmakologie Und Toxikologie, Wissenschaftliche Verlagsgesellschaft, Stuttgart, Jan. 1, 1999, p. 1-5 with Full English translation.
Rudolf Voigt et al., Pharmazeutische Technologie Fuer Studium Und Beruf,DT. Apotheker-Verl, Stuttgart; DE, Jan. 1, 2000, p. 40-52, XP008143620 with Full English translation.
Lennartsson et al., "The Stem Cell Factor Receptor/c-Kit as a Drug Target in Cancer", Current Cancer Drug Targets, 6:561-571 (2006).
N. Turner and R. Grose, "Fibroblast growth factor signalling: form development to cancer", Nature Reviews, Cancer,10:116-129 (2010).
S. Wells and M. Santoro, "Targeting the RET Pathway in Thyroid Cancer", Clinical Cancer Research, 15:7119-7123 (2009).
Giuseppe Di Lorenzo et al., "Targeted Therapy in the Treatment of Metastatic Renal Cell Cancer", Oncology, 77(Suppl.1):122-131 (2010).
Abby B.-Siegel et al., "Sorafenib: Where Do We Go from Here?" Hepatology, 52:360-369 (2010).
Kanai et al., "Development Status and Future Prospects of Novel Molecular Target Drugs for Hepatocellular Carcinoma", Journal of the Japanese Society of Gastroenterology, 106:1727-1735 (2009).
National Institutes of Health, Food and Drug Administration, National Library of Medicine, http://clinicaltrials.gov/ct2/show/study/NCT01136733, May 26, 2010.
Office Action issued for EP application No. 04818213.3 on Feb. 2, 2012.
Kitteringham et al., "A Simple Method for the Synthesis of Unsymmetrical Ureas", Synthetic Communications, 30(11):1937-1943 (2000).
Notice of Allowance issued for U.S. Appl. No. 12/986,638 on Mar. 22, 2012.
International Preliminary Examination Report and Patentability and Written Opinion for International Application No. PCT/2010/063804 dated Mar. 22, 2012.
Restriction Requirement issued for U.S. Appl. No. 11/997,543 dated Feb. 23, 2011.
Restriction Requirement issued for U.S. Appl. No. 12/092,539 dated Oct. 29, 2010.
Restriction Requirement issued for U.S. Appl. No. 12/301,353 dated Oct. 29, 2010.
Restriction Requirement issued for U.S. Appl. No. 12/439,339 dated Jul. 29, 2011.
Restriction Requirement issued for U.S. Appl. No. 12/524,754 Nov. 3, 2011.
Restriction Requirement issued for U.S. Appl. No. 13/083,338 Apr. 12, 2012.
Nishikawa et al., "Cys611Ser mutation in RET proto-oncogene in a kindred with medullary thryroid carcinoma and Hirschsprung's disease", European Journal of Human Genetics, 11,364-368 (2003).

(56) References Cited

OTHER PUBLICATIONS

Machens et al., "Genotype-Phenotype Correlations in Hereditary Medullary Thyroid Carcinoma: Oncological Features and Biochemical Properties", Journal of Clinical Endocrinology and Metabolism, 86(3):1104-1109 (2001).
Carniti et al., "The RetC62OR Mutation Affects Renal and Enteric Development in a mouse Model of Hirschprung's Disease", American Journal of Pathology, 168, 1262-1275, (2006).
Asai et al., "Mechanism of Ret Activation by a Mutation of Aspartic Acid 631 Identified in Sporadic Pheochromocytoma", Biochemical and Biophysical Research Communications, 255, 587-590 (1999).
Carlomagno et al., "Point Mutation of the RET Proto-Oncogene in the TT Human Medullary Thyroid Carcinoma cell Line", Biochemical and Biophysical Research Communications, 207,1022-1028 (1995).
Berndt et al., "A New Hot Spot for Mutations in the ret Protooncogene Causing Familial Medually Thyroid Carcinoma and Multiple Endocrine Neoplasia Type 2A", Journal of Clinical Endocrinology and Metabolism, 83, 770-774 (1998).
Miyauchi et al., "Two Germline Missense Mutations of Codons 804 and 806 of the RET protooncogene in the Same 15 Allele in a Patient with Multiple Endocrine Neoplasia Type 2B without Codon 915 Mutation", Japanese Journal of D Cancer Research, 90, 1-5, (1999).
Joao et al., "Somatic trinucleotide change encompassing codons 882 and 883 of the RET proto-oncogene in a patient with sporadic medullary thyroid carcinoma", European Journal of Endocrinology, 142, 573-575, (2000).
Kim et al., "RET Oligonucleotide Microarray for the Detection of RET Mutations in Multiple Endocrine Neoplasia Type 2 Syndromes", Clinical Cancer Research, 8,457-463, (2002).
Salvatore et al., "Molecular profile of hyalinizing trabecular tumours of the thyroid: High prevalence of RET/PTC rearrangements and absence of B-raf and N-raspoint mutations", European Journal of Cancer, 41: 816-821 (2005).
Grieco et al., "PTC is a Novel Rearranged Form of the ret Proto-Oncogene and Is Frequentrly Detected in Vivo in Human Thyroid Papillary Carcinomas", Cell, 60: 557-563 (1990).
Lam et al., "High prevalence of RET proto-oncogene activation (RET/PTC) in papillary thyroid carcinomas", Eur J Endocrinology, 147: 741-745 (2002).
Klugbauer et al., "Detection of a Novel Type of RET Rearrangement (PTC5) in Thyroid Carcinomas after Chernobyl and Analysis of the Involved RET-fused Gene RFG5", Cancer Research, 58: 198-203 (1998).
Klugbauer and Rabes, "The transcription coactivator HT1 F1 and a related protein are fused to the RET receptor tyrosine kinase in childhood papillary thyroid carcinomas", Oncogene, 18: 4388-4393 (1999).
Salassidis et al., "Translocation t(1 0; 14) (q 11.2; q22.1) Fusing the Kinectin to the RET Gene Creates a Novel Rearranged Form (PTC8) of the RET Proto-Oncogene in Radiation-induced Childhood Papillary Thyroid Carcinoma", Cancer Research, 60: 2786-2789 (2000).
Klugbauer et al., "A Novel Type of RET Rearrangement (PTC8) in Childhood Papillary Thyroid Carcinomas and Characterization of the Involved Gene (RFG8)", Cancer Research, 60: 7028-7032 (2000).
Nakata et al., "Fusion of a Novel Gene, ELKS, to RET Due to Translocation t(1 0; 12) (q11; p13) in a Papillary Thyroid Carcinoma", Genes Chromosomes Cancer, 25: 97-103 (1999).
Corvi et al., "RET/PCM-1: a novel fusion gene in papillary thyroid carcinoma", Oncogene, 19: 4236-4242 (2000).
Written Opinion of the International Searching Authority for PCT/JP2007/060560 mailed on Sep. 11, 2007 with English translation.
International Preliminary Report of Patentability issued for PCT/JP2007/060560 on Nov. 18, 2008 with English translation.
Australian Office Action directed at Appl. No. 2007252506 issued on Nov. 7, 2011.
Australian Response to Office Action directed at Appl. No. 2007252506 filed on Jan. 4, 2012.
Australian Office Action directed at Appl. No. 2007252506 issued on Jan. 13, 2012.
Chinese Office Action directed at Appl. No. 200780017371 .9 mailed on Oct. 20, 2010 with English translation.
Chinese Response to Office Action directed at Appl. No. 200780017371 .9 filed on Feb. 24, 2011 with English translation.
European Response to EESR directed at Appl. No. 07743994.1-2123 filed on Nov. 23, 2010.
Israel Office Action directed at Appl. No. 195282 issued on Jan. 26, 2010 with English translation.
Israel Response (IDS List) to Office Action directed at Appl. No. 195282 filed on May 3, 2010 with English translation.
Israel Appl. No. 195282 IDS List filed on Jul. 1, 2010.
Russian Office Action directed at Appl. No. 2008149948/15(065561) issued on May 24, 2011 with English translation.
Russian Response to Office Action directed at Appl. No. 2008149948/15(065561) filed on Jul. 27, 2011 with English translation.
Russian Decision of Grant directed at Appl. No. 2008149948/15(065561) with English translation.
US Office Action directed at U.S. Appl. No. 12/301,353 issued on Oct. 29, 2010.
US Response to Office Action directed atU.S. Appl. No. 12/301,353 filed on Nov. 23, 2010.
Australian Response to Office Action directed at Appl. No. 2007252506 filed on Mar. 2, 2012.
Response to Office Action directed at Australain Appl. No. 2006309551 filed on Mar. 30, 2012.
US Office Action directed at U.S. Appl. No. 13/083,338 dated Jun. 8, 2012.
US Final Office Action for U.S. Appl. No. 12/439,339 dated Mar. 30, 2012.
Zimmermann, "Electrical Breakdown, Electropermeabilization and Electrofusion", Rev. Physiol. Biochem. Pharmacol. 105:176-260 (1986).
"Current Protocols in Molecular Biology", John Wiley & Sons Section 11.4-11.13 (1987).
Antibodies: A Laboratory Manual, E. Harlow and D. Lane, ed.. Cold Spring Harbor Laboratory (Cold Spring Harbour, NY, 1988).
First Office Action issued on Mar. 6, 2012 for the corresponding JP application, JP2007-542863, and English translation.
Amendment and Argument filed on Apr. 27, 2012 in response to the JP Office Action for JP2007-542863 and English translation.
Heinrich et al., "Kinase Mutations and Imatinib Response in Patients with Metastatic Gastrointestinal Stromal Tumor", Journal of Clinical Oncology, vol. 21, No. 23:4342-4349 (2003).
Paulus, "Preparation and Biomedical Applications of Bispecific Antibodies", Behring Inst. Mitt. 78: 118-132 (1985).
Waterman, M., "Computer Analysis of Nucleic Acid Sequences", Methods in Enzymology, 164:765-793 (1988).
Wilbur, W.J. and Lipman, D.J., "Rapid similarity searches of nucleic acid and protein data banks", Natl. Acad. Sci, U.S.A. 80:726-730 (1983).
Altschul et al., "Basic Local Alignment Search Tool", J. Mol. BioI. 215:403-410 (1990).
Pearson, "Rapid and Sensitive Sequence Comparison with FASTP and FASTA", Methods in Enzymology 183:63-98 (1990).
Jang et al., "Mutations in Fibroblast Growth Factor Receptor 2 and Fibroblast Growth Factor Receptor 3 Genes Associated with Human Gastric and Colorectal Cancers", Cancer Research, 61:3541-3543 (2001).
Japanese Classification of Gastric Carcinoma "Igan-Toriatsukai Kiyaku" (Jun. 1999, 13th ed.) and an English translation.
Voluntary Amendment filed on Feb. 17, 2012 for TH patent appl. No. 1201000221 with English translation.
Office Action dated Apr. 11, 2012 for RU patent appl. No. 2012103471 with English translation.
Office Action dated Apr. 27, 2012 for KR patent appl. No. 10-2007-7001347 with English translation.
Office Action dated May 3, 2012 for IN patent appl. No. 383/CHENP/2008.
Examination Report dated May 9, 2012 for PK patent appl. No. 94/2011.
Office Action dated Jun. 5, 2012 for JP patent appl. No. 2009-123432 with English translation.

(56) References Cited

OTHER PUBLICATIONS

Response to the OA filed on May 29, 2012 for RU patent appl. No. 2012103471 with English translation.
Examiner's Report dated Sep. 20, 2005 for AU Patent Application No. 2001295986.
Response filed on Apr. 27, 2006 for AU Patent Application No. 2001295986.
Examiner's Report dated May 4, 2006 for AU Patent Application No. 2001295986.
Response filed on Jul. 26, 2006 for AU Patent Application No. 2001295986.
Notice of Acceptance dated Aug. 3, 2006 for AU Patent Application No. 2001295986.
Voluntary Amendment filed on Aug. 30, 2006 for AU Patent Application No. 2006203099.
Examiner's Report dated Feb. 21, 2008 for AU Patent Application No. 2006203099.
Voluntary Amendment filed on Feb. 21, 2007 for AU Patent Application No. 2006203099.
Voluntary Amendment filed on Feb. 27, 2007 for AU Patent Application No. 2006236039.
Examiner's Report dated Mar. 26, 2008 for AU Patent Application No. 2006236039.
Response filed on May 8, 2008 for AU Patent Application No. 2006236039.
Notice of Acceptance dated May 13, 2008 for AU Patent Application No. 2006236039.
Office Action dated Dec. 6, 2007 for CA Patent Application No. 2426461.
Response filed on May 16, 2008 for CA Patent Application No. 2426461.
Office Action dated Nov. 20, 2008 for CA Patent Application No. 2426461.
Response filed on Feb. 23, 2009 for CA Patent Application No. 2426461.
Office Action dated May 8, 2009 for CA Patent Application No. 2426461.
Response filed on Aug. 13, 2009 for CA Patent Application No. 2426461.
Office Action dated Feb. 10, 2010 for CA Patent Application No. 2426461.
Response filed on May 20, 2010 for CA Patent Application No. 2426461.
Voluntary Amendment filed on Aug. 19, 2010 for CA Patent Application No. 2426461.
Notice of Allowance dated Oct. 14, 2010 for CA Patent Application No. 2426461.
Amendment after Allowance filed on Jan. 4, 2011 for CA Patent Application No. 2426461.
Office Letter Confirmation of Amendment After Allowance dated Jan. 11, 2011 for CA Patent Application No. 2426461.
Amendment filed on May 28, 2003 for CN Patent Application No. 01819710.8 with English translation.
Office Action dated May 13, 2005 for CN Patent Application No. 01819710.8 with English translation.
Response filed on Sep. 13, 2005 for CN Patent Application No. 01819710.8 with English translation.
Amendment filed on Sep. 13, 2005 for CN Patent Application No. 01819710.8 with English translation.
Office Action dated Feb. 10, 2006 for CN Patent Application No. 01819710.8 with English translation.
Response filed on Apr. 11, 2006 for CN Patent Application No. 01819710.8 with English translation.
Amendment filed on Apr. 11, 2006 for CN Patent Application No. 01819710.8 with English translation.
Office Action dated Aug. 11, 2006 for CN Patent Application No. 01819710.8 with English translation.
Response filed on Oct. 9, 2006 for CN Patent Application No. 01819710.8.
Amendment filed on Oct. 9, 2006 for CN Patent Application No. 01819710.8.
Notice of Allowance dated Dec. 15, 2006 for CN Patent Application No. 01819710.8 with.
Office Action dated Jul. 24, 2009 for CN Patent Application No. 200710007096.4.
Office Action dated Mar. 6, 2009 for CN Patent Application No. 200710007097.9.
Response filed on Jul. 2, 2009 for CN Patent Application No. 200710007097.9.
Amendment filed on Jul. 2, 2009 for CN Patent Application No. 200710007097.9.
Office Action dated Sep. 11, 2009 for CN Patent Application No. 200710007097.9 with.
Response filed on Nov. 19, 2009 for CN Patent Application No. 200710007097.9 with English translation.
Amendment filed on Nov. 19, 2009 for CN Patent Application No. 200710007097.9 with English translation.
Office Action dated Dec. 25, 2009 for CN Patent Application No. 200710007097.9 with English translation.
Response filed on Jan. 26, 2010 for CN Patent Application No. 200710007097.9 with English translation.
Amendment filed on Jan. 26, 2010 for CN Patent Application No. 200710007097.9 with English translation.
Office Action dated Apr. 27, 2010 for CN Patent Application No. 200710007097.9 with English translation.
Response filed on Jun. 22, 2010 for CN Patent Application No. 200710007097.9 with English translation.
Amendment filed on Jun. 22, 2010 for CN Patent Application No. 200710007097.9 with English translation.
Voluntary Amendment filed on Aug. 11, 2010 for CN Patent Application No. 200710007097.9 with English translation.
Notice of Allowance dated Oct. 9, 2010 for CN Patent Application No. 200710007097.9 with English translation.
Partial European Search Report for EP Patent Application No. 01976786.2; Apr. 6, 2004.
Supplementary European Search Report for EP Patent Application No. 01976786.2; Jul. 6, 2004.
Invitation to declare maintenance of the application for EP Patent Application No. 01976786.2; Jul. 12, 2004.
Maintenance of the application for EP Patent Application No. 01976786.2; Sep. 6, 2004.
Amendments received before examination for EP Patent Application No. 01976786.2; Sep. 10, 2004.
Communication from the Examining Division for EP Patent Application No. 01976786.2; Aug. 17, 2005.
Brief communication to applicant for EP Patent Application No. 01976786.2; Sep. 9, 2005.
Communication from the Examining Division for EP Patent Application No. 01976786.2; Sep. 19, 2005.
Reply to communication from the Examining Division for EP Patent Application No. 01976786.2; Jan. 25, 2006.
Communication from the Examining Division for EP Patent Application No. 01976786.2; Mar. 21, 2006.
Reply to communication from the Examining Division for EP Patent Application No. 01976786.2; Jul. 19, 2006.
Communication about intention to grant a European patent for EP Patent Application No. 01976786.2; Sep. 4, 2006.
Decision to grant a European patent for EP Patent Application No. 01976786.2; Feb. 1, 2007.
Communication regarding the expiry of opposition period for EP Patent Application No. 01976786.2; Jan. 4, 2008.
European search report for EP Patent Application No. 04025700.8; Jan. 13, 2005.
Communication from the Examining Division for EP Patent Application No. 04025700.8; Apr. 10, 2006.
Reply to communication from the Examining Division for EP Patent Application No. 04025700.8; Sep. 12, 2006.
Communication from the Examining Division for EP Patent Application No. 04025700.8; Oct. 23, 2006.
Reply to communication from the Examining Division for EP Patent Application No. 04025700.8; Jan. 26, 2007.

(56) References Cited

OTHER PUBLICATIONS

Reply to communication from the Examining Division for EP Patent Application No. 04025700.8; Feb. 15, 2007.
Communication about intention to grant a European patent for EP Patent Application No. 04025700.8; Oct. 15, 2007.
Request for amendment of the text intended for grant and translation of claims for EP Patent Application No. 04025700.8; Feb. 1, 2008.
Approval of request for amendments for EP Patent Application No. 04025700.8; Mar. 13, 2008.
Decision to grant a European patent for EP Patent Application No. 04025700.8; Jun. 5, 2008.
Communication regarding the expiry of opposition period for EP Patent Application No. 04025700.8; May 7, 2009.
Deficiencies in sequence listing for EP Patent Application No. 06023078.6; Dec. 5, 2006.
Reply to the invitation to remedy deficiencies for EP Patent Application No. 06023078.6; Jan. 11, 2007.
Request for correction of errors in filed documents for EP Patent Application No. 06023078.6; Feb. 13, 2007.
European Search Report for EP Patent Application No. 06023078.6; Mar. 16, 2007.
Information about decision on request for EP Patent Application No. 06023078.6; Mar. 21, 2007.
Invitation to declare maintenance of the application for EP Patent Application No. 06023078.6; May 2, 2007.
Maintenance of the application for EP Patent Application No. 06023078.6; Jun. 19, 2007.
Communication from Examining Division for EP Patent Application No. 06023078.6; Aug. 2, 2007.
Reply to communication from the Examining Division for EP Patent Application No. 06023078.6; Sep. 11, 2007.
Communication from the Examining Division for EP Patent Application No. 06023078.6; Sep. 26, 2007.
Reply to communication from the Examining Division for EP Patent Application No. 06023078.6; Feb. 4, 2008.
Communication about intention to grant a European patent for EP Patent Application No. 06023078.6; Jul. 18, 2008.
Request for amendment of the text intended for grant and translation of claims for EP Patent Application No. 06023078.6; Nov. 5, 2008.
Decision to grant a European patent for EP Patent Application No. 06023078.6; Dec. 4, 2008.
Communication regarding the expiry of opposition period for EP Patent Application No. 06023078.6; Nov. 4, 2009.
"Voluntary Amendment filed on Sep. 10, 2010 for HU Patent Application No. P0302603" with English translation.
"Office Action dated Oct. 16, 2007 for IL Patent Application No. 155447" with English translation.
"Response filed on Dec. 4, 2007 for IL Patent Application No. 155447" with English translation.
"Notice of Allowance dated Dec. 26, 2007 for IL Patent Application No. 155447" with English translation.
"Notice Prior to Examination dated Jun. 29, 2008 for IL Patent Application No. 189677" with English translation.
"Response to Notice Prior to Examination filed on Jan. 11, 2009 for IL Patent Application No. 189677" with English translation.
"Office Action dated Feb. 18, 2009 for IL Patent Application No. 189677" with English translation.
"Response filed on May 13, 2009 for IL Patent Application No. 189677" with English translation.
"Notice of Allowance dated Mar. 14, 2010 for IL Patent Application No. 189677" with English translation.
"Amendment filed on Mar. 7, 2005 for JP Patent Application No. 2002-536056" with English translation.
"Office Action dated Apr. 11, 2005 for JP Patent Application No. 2002-536056" with English translation.
"Argument filed on Apr. 19, 2005 for JP Patent Application No. 2002-536056" with English translation.
"Amendment filed on Apr. 19, 2005 for JP Patent Application No. 2002-536056" with English translation.

"Notice of Allowance dated Aug. 2, 2005 for JP Patent Application No. 2002-536056" with English translation.
"Office Action dated Jan. 27, 2009 for JP Patent Application No. 2005-124034" with English translation.
Japanese Patent Application Laid-Open No. H11-158149 with English translation.
"Argument filed on Mar. 23, 2009 for JP Patent Application No. 2005-124034" with English translation.
"Amendment filed on Mar. 23, 2009 for JP Patent Application No. 2005-124034" with English translation.
"Office Action dated Apr. 28, 2009 for JP Patent Application No. 2005-124034" with English translation.
"Argument filed on May 21, 2009 for JP Patent Application No. 2005-124034" with English translation.
"Amendment filed on May 21, 2009 for JP Patent Application No. 2005-124034" with English translation.
"Notice of Allowance dated Jul. 21, 2009 for JP Patent Application No. 2005-124034" with English translation.
"Written Amendment filed on Jun. 16, 2009 for JP Patent Application No. 2009-123432" with English translation.
"Written Statement filed on Jun. 16, 2009 for JP Patent Application No. 2009-123432" with English translation.
"Preliminary Amendment filed on May 23, 2003 for KR Patent Application No. 10-2003-7005506" with English translation.
"Office Action dated Jul. 27, 2005 for KR Patent Application No. 10-2003-7005506" with English translation.
"Argument Brief filed on Oct. 25, 2005 for KR Patent Application No. 10-2003-7005506" with English translation.
"Amendment filed on Oct. 25, 2005 for KR Patent Application No. 10-2003-7005506" with English translation.
"Office Action dated Jan. 5, 2006 for KR Patent Application No. 10-2003-7005506" with English translation.
"Argument Brief filed on Mar. 6, 2006 for KR Patent Application No. 10-2003-7005506" with English translation.
"Amendment filed on Mar. 6, 2006 for KR Patent Application No. 10-2003-7005506" with English translation.
"Notice of decision for patent dated Jun. 12, 2006 for KR Patent Application No. 10-2003-7005506" with English translation.
"Office Action dated Dec. 8, 2005 for KR Patent Application No. 10-2005-7020292" with English translation.
"Argument Brief filed on Mar. 8, 2006 for KR Patent Application No. 10-2005-7020292" with English translation.
"Amendment filed on Mar. 8, 2006 for KR Patent Application No. 10-2005-7020292" with English translation.
"Notice of decision for patent dated Apr. 17, 2006 for KR Patent Application No. 10-2005-7020292" with English translation.
"Office Action dated Oct. 4, 2005 for MX Patent Application No. PA/a/2003/003362" with English translation.
"Response filed on Dec. 15, 2005 for MX Patent Application No. PA/a/2003/003362" with English translation.
"Office Action dated Jun. 7, 2006 for MX Patent Application No. PA/a/2003/003362" with English translation.
"Response filed on Aug. 21, 2006 for MX Patent Application No. PA/a/2003/003362" with English translation.
"Notice of Allowance dated Oct. 18, 2006 for MX Patent Application No. PA/a/2003/003362" with English translation.
"Office Action dated Nov. 26, 2007 for MX Patent Application No. PA/a/2005/013764" with English translation.
"Office Action dated Mar. 7, 2007 for NO Patent Application No. 20031731" with English translation.
"Response filed on Sep. 10, 2007 for NO Patent Application No. 20031731" with English translation.
"Office Action dated Oct. 4, 2007 for NO Patent Application No. 20031731" with English translation.
"Response filed on May 7, 2008 for NO Patent Application No. 20031731" with English translation.
"Office Action dated May 16, 2008 for NO Patent Application No. 20031731" with English translation.
"Response filed on Aug. 18, 2008 for NO Patent Application No. 20031731" with English translation.
"Office Action dated Sep. 5, 2008 for NO Patent Application No. 20031731" with English translation.

(56) References Cited

OTHER PUBLICATIONS

"Response filed on Oct. 13, 2008 for NO Patent Application No. 20031731" with English translation.
"Notice of Allowance dated Oct. 31, 2008 for NO Patent Application No. 20031731" with English translation.
"Examination Report dated Oct. 13, 2003 for NZ Patent Application No. 525324".
"Response filed on Aug. 26, 2004 for NZ Patent Application No. 525324".
"Examination Report dated Sep. 2, 2004 for NZ Patent Application No. 525324".
"Response filed on Jan. 21, 2005 for NZ Patent Application No. 525324".
"Examination Report dated Feb. 18, 2005 for NZ Patent Application No. 525324".
"Notice of Acceptance of Complete Specification dated Mar. 4, 2005 for NZ Patent Application No. 525324".
"Formality Requirement dated Jun. 18, 2003 for PH Patent Application No. 1-2003-500266".
"Response filed on Aug. 5, 2003 for PH Patent Application No. 1-2003-500266".
"Office Action dated Aug. 8, 2003 for PH Patent Application No. 1-2003-500266".
"Response filed on Sep. 8, 2003 for PH Patent Application No. 1-2003-500266".
"Response filed on Sep. 15, 2003 for PH Patent Application No. 1-2003-500266".
"Office Action dated Jul. 21, 2006 for PH Patent Application No. 1-2003-500266".
"Response filed on Aug. 14, 2006 for PH Patent Application No. 1-2003-500266".
"Office Action dated Mar. 21, 2007 for PH Patent Application No. 1-2003-500266".
"Response filed on Apr. 17, 2007 for PH Patent Application No. 1-2003-500266".
"Office Action dated Jun. 27, 2007 for PH Patent Application No. 1-2003-500266".
"Response filed on Jul. 31, 2007 for PH Patent Application No. 1-2003-500266".
"Office Action dated Sep. 7, 2007 for PH Patent Application No. 1-2003-500266".
"Response filed on Oct. 15, 2007 for PH Patent Application No. 1-2003-500266".
"Notice of Allowability dated Nov. 28, 2007 for PH Patent Application No. 1-2003-500266".
"Response to the Notice of Allowability filed on Dec. 13, 2007 for PH Patent Application No. 1-2003-500266".
"Notification dated Apr. 25, 2008 for PH Patent Application No. 1-2003-500266".
"Response filed on Apr. 30, 2008 for PH Patent Application No. 1-2003-500266".
"Registered dated Feb. 24, 2009 for PH Patent Application No. 1-2003-500266".
"Office Action dated Jun. 29, 2004 for RU Patent Application No. 2003114740" with English translation.
"Response filed on Nov. 30, 2004 for RU Patent Application No. 2003114740" with English translation.
"Office Action dated Jan. 19, 2005 for RU Patent Application No. 2003114740" with English translation.
"Response filed on Mar. 17, 2005 for RU Patent Application No. 2003114740" with English translation.
"Notice of Allowance dated Apr. 19, 2005 for RU Patent Application No. 2003114740" with English translation.
"Amendment filed on Apr. 17, 2002 for TW Patent Application No. 90125928" with English translation.
"Rejection dated Apr. 26, 2004 for TW Patent Application No. 90125928" with English translation.
"Reexamination filed on Nov. 25, 2004 for TW Patent Application No. 90125928" with English translation.
"Office Action dated Oct. 11, 2007 for TW Patent Application No. 90125928" with English translation.
"Response filed on Dec. 11, 2007 for TW Patent Application No. 90125928" with English translation.
"Notice of Allowance dated Oct. 20, 2008 for TW Patent Application No. 90125928" with English translation.
"Notice of Allowance dated Jun. 3, 2008 for U.S. Appl. No. 11/293,785".
"Notice of Allowance dated Nov. 19, 2008 for U.S. Appl. No. 11/293,785".
"Notice of Allowance dated Feb. 27, 2009 for U.S. Appl. No. 11/293,785".
"Notice of Allowance dated May 18, 2009 for U.S. Appl. No. 11/293,785".
"Preliminary Amendment filed on Apr. 18, 2003 for U.S. Appl. No. 10/420,466".
"Office Action dated Apr. 13, 2005 for U.S. Appl. No. 10/420,466".
"Response filed on Jul. 1, 2005 for U.S. Appl. No. 10/420,466".
"Notice of Allowance dated Sep. 12, 2005 for U.S. Appl. No. 10/420,466".
"Notice of Allowance dated Jun. 13, 2006 for U.S. Appl. No. 10/420,466".
"Notice of Allowance dated Mar. 16, 2007 for U.S. Appl. No. 10/420,466".
Preliminary Amendment filed on Dec. 2, 2005 for U.S. Appl. No. 11/293,785.
"Preliminary Amendment filed on Feb. 3, 2006 for U.S. Appl. No. 11/293,785".
"Office Action dated Sep. 4, 2007 for U.S. Appl. No. 11/293,785".
"Response filed on Feb. 26, 2008 for U.S. Appl. No. 11/293,785".
"Notification of Non-Compliant Amendment filed on Jan. 13, 2005 for U.S. Appl. No. 10/420,466".
"Office Communication concerning dated Sep. 13, 2004 for U.S. Appl. No. 10/420,466".
"Response filed on Oct. 8, 2004 for U.S. Appl. No. 10/420,466".
"Preliminary Amendment filed on Oct. 27, 2003 for U.S. Appl. No. 10/420,517".
ISR dated Jan. 15, 2002 for International Patent Application No. PCT/JP01/09221.
IPRP dated Jan. 8, 2003 for International Patent Application No. PCT/JP01/09221.
Amendment filed on Aug. 4, 2004 for ZA Patent Application No. 2003/3567.
Notice of Acceptance dated Aug. 10, 2004 for ZA Patent Application No. 2003/3567.
Amendment filed on Aug. 17, 2004 for ZA Patent Application No. 2003/3567.
Amended description filed after receipt of search report for EP Patent Application No. 10809938.3; Dec. 8, 2011.
"Amendment filed on Dec. 12, 2011 for JO Patent Application No. 55/2011" with English translation.
"Written Amendment filed on Sep. 21, 2011 for JP Patent Application No. 2011-527665" with English translation.
"Written Statement filed on Sep. 21, 2011 for JP Patent Application No. 2011-527665" with English translation.
Amendment filed on Oct. 28, 2011 for LB Patent Application No. 9292.
Amendment filed on Feb. 9, 2011 for TW Patent Application No. 100104281.
"Amendment filed on Dec. 15, 2011 for VN Patent Application No. 1-2011-03484" with English translation.
"ISR dated Sep. 14, 2010 for International Patent Application No. PCT/JP2010/063804".
"IPRP dated Mar. 13, 2012 for International Patent Application No. PCT/JP2010/063804".
Amendment filed on Dec. 22, 2011 for ZA Patent Application No. 2011/08697.
"Voluntary Amendment filed on Feb. 9, 2010 for AU Patent Application No. 2005283422".
"Notice of Allowance dated Apr. 29, 2010 for AU Patent Application No. 2005283422".
"Voluntary Amendment filed on Jul. 6, 2010 for AU Patent Application No. 2005283422".

(56) References Cited

OTHER PUBLICATIONS

"Office Action dated Jul. 15, 2011 for CA Patent Application No. 2579810".
"Response filed on Sep. 21, 2011 for CA Patent Application No. 2579810".
"Notice of Allowance dated Oct. 17, 2011 for CA Patent Application No. 2579810".
"Office Action dated Jun. 26, 2009 for CN Patent Application No. 200580026468.7" with English translation.
"Response filed on Sep. 23, 2009 for CN Patent Application No. 200580026468.7" with English translation.
"Amendment filed on Sep. 23, 2009 for CN Patent Application No. 200580026468.7" with English translation.
"Office Action dated Nov. 20, 2009 for CN Patent Application No. 200580026468.7" with English translation.
"Response filed on Jan. 11, 2010 for CN Patent Application No. 200580026468.7" with English translation.
"Amendment filed on Jan. 11, 2010 for CN Patent Application No. 200580026468.7" with English translation.
"Notice of Allowance dated Feb. 5, 2010 for CN Patent Application No. 200580026468.7" with English translation.
Communication regarding the expiry of opposition period for EP Patent Application No. 05783232.1; Feb. 19, 2010.
"Decision to grant a European patent for EP Patent Application No. 05783232.1; Mar. 19, 2009".
"Communication about intention to grant a European patent for EP Patent Application No. 05783232.1; Nov. 20, 2008".
"Reply to official communication for EP Patent Application No. 05783232.1; Apr. 30, 2008".
"Communication from the Examining Division for EP Patent Application No. 05783232.1; Feb. 7, 2008".
"Maintainance of the application for EP Patent Application No. 05783232.1; Nov. 9, 2007".
Invitation to declare maintenance of the application for EP Patent Application No. 05783232.1; Sep. 25, 2007.
"European Search Report for EP Patent Application No. 05783232.1; Sep. 7, 2007".
"Notice Prior to Examination dated Mar. 9, 2009 for IL Patent Application No. 181697" with English translation.
"Response to Notice Prior to Examination filed on Apr. 22, 2009 for IL Patent Application No. 181697" with English translation.
"Office Action dated Dec. 20, 2010 for IL Patent Application No. 181697" with English translation.
"Response filed on Jan. 26, 2011 for IL Patent Application No. 181697" with English translation.
"Notice of Allowance dated Nov. 14, 2011 for IL Patent Application No. 181697" with English translation.
"Notice of Allowance dated Sep. 20, 2011 for JP Patent Application No. 2006-535174" with English translation.
Japanese Patent Application Laid-Open No. S63-028427 with English translation.
Japanese Patent Application Laid-Open No. 2003-026576 with English translation.
WO00/071097 with English translation.
"Office Action dated Sep. 28, 2011 for KR Patent Application No. 10-2007-7001347" with English translation.
"Amendment filed on Nov. 24, 2011 for KR Patent Application No. 10-2007-7001347" with English translation.
"Argument Brief filed on Nov. 24, 2011 for KR Patent Application No. 10-2007-7001347" with English translation.
"ISR dated Nov. 15, 2005 for International Patent Application No. PCT/JP2005/016941".
"IPRP dated Mar. 20, 2007 for International Patent Application No. PCT/JP2005/016941".
Office Action for JP2007-542863 dated May 29, 2012 with English translation.
AU2006309551 Response to Office Action filed on Mar. 28, 2012.
CN Office Action issued for CN 200880002425.9 on Mar. 7, 2012 with English translation.
AU Office Action issued for AU 2008211952 on Apr. 3, 2012.
CN Office Action directed at Appl. No. 200780017371.9 mailed on Mar. 7, 2012 with English translation.
IL Office Action issued for IL 195282 on Feb. 5, 2012 with English translation.
CN Office Action issued for CN 200880115011.7 on Feb. 20, 2012 with English translation.
Response to IL OA directed at Appl. No. 205512 filed on Mar. 11, 2012 with English translation.
Response to IL OA directed at Appl. No. 207089 filed on Mar. 11, 2012 with English translation.
AU Office Action issued for AU 2008205847 on Apr. 11, 2012.
Response to the OA issued for U.S. Appl. No. 11/997,543 filed on Mar. 22, 2011.
Response to the OA issued for U.S. Appl. No. 11/997,543 filed on Aug. 19, 2011.
Response to the OA issued for U.S. Appl. No. 11/997,543 filed on Jan. 9, 2012.
Response to the OA issued for U.S. Appl. No. 11/997,719 filed on Dec. 23, 2010.
Response to the Final OA issued for U.S. Appl. No. 11/997,719 filed on Jul. 6, 2011.
Response to Office Action directed at U.S. Appl. No. 12/301,353 filed on Nov. 23, 2010.
Response to the OA for U.S. Appl. No. 12/439,339 filed on Aug. 10, 2011.
Response to the OA for U.S. Appl. No. 12/439,339 filed on Feb. 7, 2012.
Response to the OA for U.S. Appl. No. 12/523,495 filed on Dec. 7, 2011.
Response to the OA for U.S. Appl. No. 12/524,754 filed on Dec. 1, 2011.
Response to the OA for U.S. Appl. No. 12/524,754 filed on Feb. 17, 2012.
Response to the OA for U.S. Appl. No. 12/864,817 filed on Aug. 9, 2011.
Response to the OA of U.S. Appl. No. 12/864,817 filed on Dec. 5, 2011.
Response to the OA for U.S. Appl. No. 12/864,817 filed on Dec. 22, 2011.
Asano et al., "Inhibition of Tumor Growth and Metastasis by an Immunoneutralizing Monoclonal Antibody to Human Vascular Endothelial Growth Factor/Vascular Permeability Factor121", Cancer Research., 55, 5296-5301, 1995.
Hori et al., "Suppression of Solid Tumor Growth by Immunoneutralizing Monoclonal Antibody against Human Basic Fibroblast Growth Factor", Cancer Research., 51, 6180-4, 1991.
Gutheil et al., Targeted Antiangiogenic Therapy for Cancer Using Vitaxin: A Humanized Monoclonal Antibody to the Integrin alphavbeta3 1 Clinical Cancer Research., 6, 3056-61, 2000.
Dias et al., "IL-12 Regulates VEGF and MMPs in a Murine Breast Cancer Model", International J. Cancer., 78, 361-5, 1998.
Liu et al., "Structure of Human Methionine Aminopeptidase-2 Complexed with Fumagillin", Science., 282, 1324-1327, 1998.
Wedge et al., "ZD4190: An Orally Active Inhibitor of Vascular Endothelial Growth Factor Signaling with Broad-Spectrum Antitumor Efficacy", Cancer Research., 60, 970-975, 2000.
Hannequin et al., "Design and Structure-Activity Relationship of a New Class of Potent VEGF Receptor Tyrosine Kinase Inhibitors", Journal of Medicinal Chemistry., 42: 5369-5389, 1999.
Fong et al., "SU5416 Is a Potent and Selective Inhibitor of the Vascular Endothelial Growth Factor Receptor (Flk-1/KDR) That Inhibits Tyrosine Kinase Catalysis, Tumor Vascularization, and Growth of Multiple Tumor Types", Cancer Research., 59, 99-106, 1999.
Laird et al., "SU6668 Is a Potent Antiangiogenic and Antitumor Agent That Induces Regression of Established Tumors1", Cancer Research., 60, 4152-4160, 2000.
Gingrich et al., "A New Class of Potent Vascular Endothelial Growth Factor Receptor Tyrosine . . . Clinical Candidate CEP-7055", Journal of Medicinal Chemistry., 46: 5375-88, 2003.

(56) References Cited

OTHER PUBLICATIONS

Beebe et al., "Pharmacological Characterization of CP-547,632, a Novel Vascular Endothelial Growth Factor Receptor-2 Tyrosine Kinase Inhibitor for Cancer Therapy1", Cancer Research. 63:7301-9, 2003.
Petti et al., "Temporal quantitation of mutant Kit tyrosine kinase signaling attenuated by a novel thiophene kinase inhibitor OSI-930", Molecular Cancer Therapeutics., 4:1186-1197, 2005.
Guo et al., "In Vitro Pharmacological Characterization of TKI-28, a Broad-Spectrum Tyrosine Kinase Inhibitor with Anti-Tumor and Anti-Angiogenic Effects", Cancer Biol Ther., 4, p. 1125-1132, 2005.
Lee et al., "In vivoTargetModulation and Biological Activity of CHIR-258, aMultitargeted Growth Factor Receptor Kinase Inhibitor, in Colon CancerModels", Clinical Cancer Research., 11, 3633-3641, 2005.
Emanuel et al., "A Vascular Endothelial Growth Factor Receptor-2 Kinase Inhibitor Potentiates the Activity of the Conventional Chemotherapeutic Agents Paclitaxel and Doxorubicin in Tumor Xenograft Models", Molecular Pharmacology., 66, 635-647, 2004.
Ruggeri et al., "CEP-7055: A Novel, Orally Active Pan Inhibitor of Vascular Endothelial Growth Factor Receptor Tyrosine Kinases with Potent Antiangiogenic Activity and Antitumor Efficacy in Preclinical Models1", Cancer Research., 63, 5978-5991, 2003.
Kubo et al., "Novel Potent Orally Active Selective VEGFR-2 Tyrosine Kinase Inhibitors: . . . ureas", Journal of Medicinal Chemistry., 48, 1359-1366, 2005.
Amino et al., "YM-231146, a Novel Orally Sioavailable Inhibitor of Vascular Endothelial Growth Factor Receptor-2, Is Effective against Paclitaxel Resistant Tumors", Biological and Pharmaceutical Bulletin. 28:2096-2101, 2005.
Podar et al., "GW654652, the pan-inhibitor of VEGF receptors, blocks the growth and migration of multiple myeloma cells in the bone marrow microenvironment", Blood.,103, 3474-3479, 2004.
Bainbridge et al., "A peptide encoded by exon 6 of VEGF (EG3306) inhibits VEGF-induced angiogenesis in vitro and ischaemic retinal neovascularisation in vivo", Biochem Biophys Res Commun., 302, 793-799, 2003.
Ueda et al., "VGA1155, a Novel Binding Antagonist of VEGF, Inhibits Angiogenesis In Vitro and In Vivo", Anticancer Research., 24, 3009-3017, 2004.
Wulff et al., "Luteal Angiogenesis: Prevention and Intervention by Treatment with Vascular Endothelial Growth Factor TrapA40", The Journal of Clinical Endocrinology & Metabolism. 86(7), 3377-3386, 2001.
Mohammadi et al., "Crystal structure of an angiogenesis inhibitor bound to the FGF receptor tyrosine kinase domain", EMBO J., 17, 5896-5904, 1998.
Roberts et al., "Antiangiogenic and Antitumor Activity of a Selective PDGFR Tyrosine Kinase Inhibitor, CP-673,451", Cancer Research., 65, 957-966, 2005.
Kubo et al., "A Novel Series of 4-Phenoxyquinolines: Potent and Highly Selective Inhibitors of PDGF Receptor Autophosphorylation", Bioorganic and Medicinal Chemistry Letters., 7, 2935-2940, 1997.
Wood et al., "A Unique Structure for Epidermal Growth Factor Receptor Bound to GW572016 (Lapatinib): Relationships among Protein Conformation, Inhibitor Off-Rate, and Receptor Activity in Tumor Cells", Cancer Research., 64, 6652-6659. 2004.
Nyati et al., "Radiosensitization by Pan ErbB Inhibitor CI-1033 in Vitro and in Vivo", Clinical Cancer Research., 10:691-700, 2004.
El-Abseri et al., "Chemoprevention of UV Light-Induced Skin Tumorigenesis by Inhibition of the Epidermal Growth Factor Receptor", Cancer Research., 64, 3958-3965, 2004.
Tsou et al., "Optimization of 6,7-Disubstituted-4-(arylamino)quinoline-3-carbonitriles as Orally Active, Irreversible Inhibitors of Human Epidermal Growth Factor Receptor-2 Kinase Activity", Journal of Medicinal Chemistry., 48, 1107-1131, 2005.
Experimental Medicine, Supplementary Volume, "A New Handbook of Genetic Engineering", Section 4, YODOSHA, 2003(Japanese).

Cell Technology, Supplementary Volume, "Bio-Experiment Illustrated vol. 5, No Fear of Proteins", Visual Laboratory Notebook Series, Section 6, Immunostaining, pp. 127-163, Shujunsha, Co., Ltd., 1997 (Japanese).
Masferrer et al., "COX-2 Inhibitors A New Class of Antiangiogenic Agents", Annals of N.Y. Acad. Science., 889:84-6, 1999.
Bramhall, S., "The Matrix Metalloproteinases and Their Inhibitors in Pancreatic Cancer", International J. Pancreatol., 21, 1-12, 1997.
AACR American Association Cancer Research, 92nd Annual Meeting, 42:583, Mar. 24-28, 2001, New Orleans, LA, USA, 3126.
AACR American Association Cancer Research., 93nd Annual Meeting, 43:1080, Apr. 6-10, 2002, San Francisco, CA, USA, 5347.
AACR American Association Cancer Research., 96th Annual Meeting, 46, (Abstract 2031), Anaheim, Orange County, CA, USA Apr. 2005.
EORTC-NCI-AACR Symp Mol Targets Cancer Ther., 2, (Abstract 172), 2004.
AACR American Association Cancer Research, 96th Annual Meeting, 46:1407, (Abstract 5981), Anaheim, Orange County CA USA Apr. 16-20, 2005.
AACR American Association Cancer Research, 96th Annual Meeting, 46 (Abstract 3033), Anaheim, Orange County CA USA Apr. 16-20, 2005.
"Pharmacokinetics (PK) and tolerability of GW786034, a VEGFR tyrosine kinase inhibitor, after daily oral administration to patients with solid tumors.", Proc. Am. Soc. Clin. Oncology, (Abstract 3054), 2004.
ZK304709 (Proceedings of the American Association for Cancer Research, 46, (Abstract 5842), 2005.
EORTC-NCI-AACR Symp Mol Targets Cancer Ther., (Abstract 134), 2004.
EORTC-NCI-AACR Symp Mol Targets Cancer Ther., 2, (Abstract 151), 2004.
Proceedings of the American Association for Cancer Research, 44, 9, (Abstract 39), 2003.
Proceedings of the American Association for Cancer Research, 44, 9, (Abstract 40), 2003.
Proceedings of the American Association for Cancer Research, 45, 694, (Abstract 3005), 2004.
Proceedings of the American Association for Cancer Research, 44, 1479, (Abstract 6454), 2003.
Proc. Am. Soc. Clin. Oncology, (Abstract 776), 2003.
Am. Assoc. Cancer Research, A3394, 2005.
Am. Assoc. Cancer Research, A3405, 2005.
"Recent Results and Ongoing Trials with Panitumumab (ABX-EGF), a Fully Human Anti-Epidermal Growth Factor Receptor Antibody, in Metastatic Colorectal Cancer", Clinical Colorectal Cancer. 2005; 5(1):21-3.
Kim, T , "Technology evaluation: Matuzumab, Merck KGaA", Curr Opin Mol Ther. 2004; 6(1):96-103.
Am. Assoc. Cancer Research, Abstract 5353, 2005.
David et al., "A Phase I Trial of the Epidermal Growth Factor Receptor (EGFR)-Directed Bispecific Antibody (BsAB) MDX-447 in Patients with Solid Tumors. (Meeting abstract).", ASCO 18: 433, Abstract 1999.
The Pharmacology of Monoclonal Antibody, vol. 113, Chapter 11, Rosenburg and Moore ed., Springer Verlag (1994) pp. 269-315.
LeDoussal et al. "Bispecific-Antibody-Mediated Targeting of Radiolabeled Bivalent Haptens: Theoretical, Experimental and Clinical Results", Int. J. Cancer Suppl. 7: 58-62, 1992.
Millstein and Cuello, "Hybrid hybridomas and their use in immunohistochemistry", Nature 305: 537-9, 1983.
Am. Assoc. Cancer Res. Abstract 3399, 2005.
Proceedings of the American Association for Cancer Research, 45, 594, (Abstract 2571), 2004.
Proceedings of the American Association for Cancer Research, 44, 865, (Abstract 3780), 2003.
Decision of Rejection issued on May 29, 2012 for JP No. 2007-542863 with English translation.
Dvorakova et al., "Exon 5 of the RET proto-oncogene: A newly detected risk exon for familial medullary thyroid carcinoma, a novel germ-line mutation Gly321Arg", Journal of Endocrinological Investigation, 28, 905-909, 2005.

(56) References Cited

OTHER PUBLICATIONS

Kinlaw et al., "Multiple endocrine neoplasia 2A due to a unique C6095 RET mutation presents with pheochromocytoma and reduced penetrance of medullary thyroid carcinoma", Clin Endocrinol, 69, 676-682, 2005.
Dourisboure et al, "Penetrance and Clinical Manifestations of Non-Hotspot Germ line RET Mutation, C630R, in a Family with Medullary Thyroid Carcinoma", Thyroid, 15, 668-671, 2005.
Kruckeberg et al., "Pyrosequencing Technology as a Method for the Diagnosis of Multiple Endocrine Neoplasia Type 2", Clinical Chemistry, 50, 522-529, 2004.
Bartsch et al., "A RET double mutation in the germline of a kindred with FMTC", Exp. Clin Endocrinol Diabetes, 108, 128-132, 2000.
Fugazzola et al., "Molecular and biochemical analysis of RET/PTC4, a novel oncogenic rearrangement between RET and ELE1 genes, in a post-Chernobyl papillary thyroid cancer", Oncogene, 13, 1093-1097, 1996.
Hara et al., "Amplification of c-myc, K-sam, and c-met in Gastric Cancers: Detection by Fluorescence In Situ Hybridization", Laboratory Investigation, 78, 1143-1153, 1998.
Office Action issued for JP Appl. No. 2007-529565 issued on May 8, 2012 with English translation.
Response to EP OA for EP 07806561.2 filed on Apr. 18, 2012.
Response to CN OA for CN200880003336.6 filed on May 3, 2012.
Response to IL OA for IL 195282 filed on May 28, 2012.
Response to AU OA for AU 2008211952 filed on Jun. 28, 2012.
Heinemann, V., et al., "Comparison of the Cellular Pharmacokinetics and Toxicity of . . . 1-beta-d-Arabinofuranosylcytosine", Cancer Research, 48, 4024-4031, 1988.
Hertel LW., et al., "Evaluation of the Antitumor Activity of Gemcitabine (2',2'-Difluoro-2'-deoxycytidine)", Cancer Research, 50, 4417-4422, 1990.
IPRP (PCT/JP2008/051024)dated Jul. 21, 2009, with English translation.
Office Action issued for CN 200880002425.9 on Mar. 2, 2011 with English translation.
Argument and Amendment for CN 200880002425.9 filed on Jul. 18, 2011 with English translation.
Office Action for CN 200880002425.9 issued on Mar. 7, 2012 with English translation.
Office Action for IL 199907 issued on Jun. 17, 2010 with English translation.
Response to Office Action for IL 199907 filed on Oct. 11, 2010 with English translation.
Office Action issued for EP06768437.3 (EPO Form1224) issued on Oct. 28, 2010.
Response to OA for EP10015141 filed on Mar. 5, 2012.
PCT/JP2006/0315563 Written Opinion of the International Searching Authority dated Feb. 5, 2008, with English translation.
PCT/JP2006/315563 International Preliminary Report on Patentability dated Feb. 5, 2008, with English translation.
PCT/JP2006/0315698 Written Opinion of the International Searching Authority, dated Feb. 5, 2008, with English translation.
PCT/JP2006/315698 International Preliminary Report on Patentability with dated Feb. 5, 2008, English translation.
Submission of Documents re Claim 3 and Figure 3 for KR App. Ser. No. 10-2009-7005657, filed on Jul. 13, 2012.
Official Letter for AU2008211952 dated Jul. 10, 2012.
Response to Office Action for U.S. Appl. No. 12/741,682 filed Jul. 30, 2012.
Communication (Notice of Allowance) for JP2011-527665 dated Jul. 17, 2012 (with English translation).
Communication (Notice of Allowance) for EP07806561.2 dated Jun. 25, 2012.
Communication (Notice of Allowance) for EP06782407.8 dated Jun. 20, 2012.
Submission of Documents re UAa201203132, dated May 22, 2012 with English translation.
Office Letter for ZA 2011/08697, dated May 25, 2012.
Response to OA for U.S. Appl. No. 12/439,339 filed Jul. 30, 2012.
Submission of Documents for CO 12-022608 dated Jun. 12, 2012.
Chinese Office Action for CN 200680020317.5 dated Aug. 3, 2012 with English translation.
Official Letter for SG 201108602-2 dated Aug. 8, 2012.
Office Action for U.S. Appl. No. 13/083,338 dated Jun. 8, 2012.
European Search Report for EP 08846814.5 dated Jun. 18, 2012.
Office Action for JP2007-529565 dated Aug. 7, 2012 with English translation.
Noriyuki et al., "Anti-tumor effect of E7080, a novel angiogenesis inhibitor", Database Biosis (online) Biosciences Information Service, Philadelphia, PA, US., Database Accession No. PREV200800475929 (abstract), Aug. 2008, XP002677323.
European Search Report for EP 08704376.6 dated Jun. 14, 2012.
Response to Office Action for U.S. Appl. No. 13/083,338 filed Sep. 6, 2012.
De Lange et al., "Phase II trial of cisplatin and gemcitabine in patients with advanced gastric cancer", Annals of Oncology, Kluwer, Dordrecht, NL, 15(3): 484-488, Mar. 1, 2004, XP002511249.
Sihto, H., "KIT and Platelet-Derived Growth Factor Receptor Alpha Tyrosine Kinase Gene Mutations and KIT Amplifications in Human Solid Tumors", 23 J. Clin. Oncol. 49-57 (Jan. 1, 2005).
Office Action for IL 199907 issued on Apr. 22, 2012 with English translation.
Response to Chinese Office Action filed for CN 200880115011.7 dated Jul. 5, 2012, with English translation.
Japanese Office Action for JP2009-123432 dated Sep. 4, 2012, with English translation.
Response to Chinese Office Action for CN 200680020317.5 dated Sep. 11, 2012, with English translation.
Official Letter for CA Patent Application No. 2627598 dated Sep. 19, 2012.
Schlumberger et al., "A Phase 2 Trial of the Multi-Targeted Kinase Inhibitor Lenvatinib(E7080) in Advanced Medullary Thyroid Cancer (MTC)", 2012 ASCO Annual Meeting, Poster Presentation, Jun. 1-5, 2012.
Funahashi et al., "P-2123, Lenvatinib treatment of differentiated thyroid cancer (DTC): Analysis to identify biomarkers associated with response", The 71$^{st}$ Annual Meeting of the Japanese Cancer Association, p. 339, Sep. 19-21, 2012.
Tohyama et al., "P-3111, Preclinical effect of lenvatinib on human thyroid cancer targeting angiogenesis and receptor tyrosine kinase signaling", The 71$^{st}$ Annual Meeting of the Japanese Cancer Association, p. 502, Sep. 19-21, 2012.
Chinese Office Action for CN 200880003336.6 dated Sep. 5, 2012, with English translation.
Chinese Office Action for CN 200880115011.7 dated Sep. 5, 2012, with English translation.
Notice of Allowance for U.S. Appl. No. 12/98,6638, Sep. 25, 2012.
Response to Chinese Office Action filed for CN 200880003336.6 dated Jul. 11, 2012, with English translation.
Office Action for U.S. Appl. No. 13/322,961 dated Sep. 25, 2012.
Notice of Allowance for U.S. Appl. No. 12/524,754 dated Oct. 9, 2012.
Office Action for CN 200780017371.9 dated Sep. 28, 2012 with English translation.
Office Action for JP 2008-516724 dated Oct. 9, 2012 with English translation.
Bernex et al., "Spatial and temporal patterns of c-kit-expressing cells in WlacZ/+ and WlacZ/WlacZ mouse embryos", Development 122:3023-3033 (1996).
Office Action for IL 200090 dated Oct. 15, 2012 with English translation.
Office Action (Notice of Allowance) for EP 06782407.8 dated Nov. 2, 2012.
Office Action (Notice of Allowance) for EP 07806561.2 dated Nov. 2, 2012.
Office Action for JP 2008-532141 dated Nov. 13, 2012 with English translation.
Office Action from CN Patent Application No. 200780017371.9 dated Mar. 14, 2013 (with English translation).
Response to Office Action for IN Patent Application No. 1571/CHENP/2007 dated Apr. 10, 2013.
Office Action for U.S. Appl. No. 11/997,719 dated Apr. 8, 2013.

(56) References Cited

OTHER PUBLICATIONS

Office Action for CN Patent Application No. 201080030508.6 dated Apr. 9, 2013 (with English translation).
Office Action for CA Application No. 2652442 dated Apr. 16, 2013.
Office Action for IL Patent Application No. 217197 dated Apr. 11, 2013 (with English translation).
Response to Office Action for IL Application No. 207089 dated Apr. 22, 2013 (with English translation).
Preliminary Amendment for U.S. Appl. No. 13/870,507, filed Apr. 26, 2013.
Communication (Notice of Allowance) for EP Application No. 04818213.3 dated May 6, 2013.
Request to amend specification for Australian Patent Application No. 2009210098 dated May 9, 2013.
Amendment and RCE for U.S. Appl. No. 12/741,682 dated May 17, 2013.
Supplementary Observation for CN Application No. 200980103218.7 dated March 13, 201 (with English translation).
Response to Office Action for CN Application No. 200880115011.7 dated April 11, 201 (with English translation).
Office Action for EP08846814.5 dated Apr. 16, 2013.
Request for Continued Examination and Information Disclosure Statement for U.S. Appl. No. 12/524,754, filed Apr. 15, 2013.
Office Action for KR 10-2008-7013685 dated May 20, 2013 (with English translation).
Office Action for JP2008-532141 dated May 21, 2013 (with English translation).
Office Action for U.S. Appl. No. 12/439,339 dated May 23, 2013.
Applicant Interview Summary for U.S. Appl. No. 12/439,339 dated May 23, 2013.
Response to Office Action for CN201080030508.6 dated May 27, 2013 (with English translation).
Request for Substantive Examination for UA a201203132 dated Apr. 15, 2013 (with English translation).
Request for Substantive Examination for ID W-00201201031 dated Jun. 3, 2013 (with English translation).
Notice of Acceptance (Notice of Allowance) for AU2009210098 dated Jun. 4, 2013.
Notice of Allowance for U.S. Appl. No. 13/083,338 dated Jun. 4, 2013.
"Amendment and Response to Office Action Under 37 C.F.R. § 1.111" submitted for U.S. Appl. No. 13/624,278, dated Jun. 28, 2013.
Notice of Allowance for CN Patent Application No. 200980103218.7 dated May 27, 2013 (with English translation).
Office Action for IL Application No. 195282 dated Apr. 10, 2013 (with English translation).
U.S. Appl. No. 13/923,858, filed Jun. 21, 2013.
Koyama et al., "Anti-tumor effect of E7080, a novel angiogenesis inhibitor", Folia Pharmacol. Jpn. 132, Therapeutic Agents Series (28), Molecular Target Drugs-1-1, pp. 100-104, Apr. 18, 2008.
Haiyi Jiang, "ZD6474: an Agent That Selectively Targets Both VEGFR Tyrosine Kinase and EGFR Tyrosine Kinase", Japanese Journal of Lung Cancer, Vol.46, No. 3, Jun. 20, 2006, pp. 283-288.
Stefan Frings, "New Molecular Targeted Therapeutic Drugs Clinical Results of Bevacizumab in Non-Small Cell Lung Cancer (NSCLC)", Japanese Journal of Lung Cancer, Vol.46, No. 3, Jun. 20, 2006, pp. 277-281.
Lumi Chikahisa et al., "TSU-68 JDR/flk-inhibitor, can modulate the anti-tumor activity of paclitaxel by the induction of endothelial cell and tumor cell apoptosis", 61st Annual Meeting of Japanese Cancer Association, 2002, vol. 61, No. 1374, 2002, p. 443.
Office Action for JP2009-551518 dated Jun. 18, 2013 (with English translation).
The Argument and the Amendment for JP Patent Application No. 2008-532141 filed on Nov. 29, 2012, (with English translation).
The Argument and the Amendment for JP Patent Application No. 2008-556208 filed on Mar. 21, 2013, (with English translation).
The Argument and the Amendment for JP Patent Application No. 2008-516724 filed on Nov. 28, 2012, (with English translation).
The Explanation of Circumstances Concerning Accelerated Examination and the Amendment filed on May 10, 2012 for JP Patent Application No. 2011-527665 (with English translation).
The Argument and the Amendment for JP Patent Application No. 2009-123432 filed on Jun. 12, 2012, (with English translation).
The Argument and the Amendment for JP Patent Application No. 2009-529019 filed on Jul. 3, 2012, (with English translation).
Response to Office Action for CN Application No. 200780017371.9 dated May 29, 2013 (with English translation).
Response to Office Action for U.S. Appl. No. 11/997,719, filed Jul. 3, 2013.
Office Action for JP Application No. 2009-540099 dated Jul. 2, 2013 (with English translation).
Notice of Allowance for CN Patent Application No. 201080030508.6 dated Jul. 4, 2013 (with English translation).
Notice of Allowance for JP Patent Application No. P2008-0556208 dated Jul. 9, 2013 (with English translation).
Matsui et al., "Extracellular matrix of linitis plastica as possible new therapeutic target", Surgical treatment 89(3):301-306 (Sep. 1, 20113) (with English translation).
Amendment for Application No. IL Patent Application No. 195282 dated Jul. 11, 2013 (with English translation).
Amended Claims for KR Patent Application 10-2010-7011023 dated Jul. 17, 2013 (with English translation).
Communication for EP Patent Application No. 10809938.3 dated Jul. 19, 2013.
Notice of Allowance for U.S. Appl. No. 12/524,754 dated Jul. 19, 2013.
Notice of Allowance for EP Patent Application No. 10015141.4 dated Jul. 1, 2013.
Response to Office Action for IL Patent Application No. 217197 dated Jul. 31, 2013 (with English translation).
Response to Communication for EP Patent Application No. 08846814.5 dated Aug. 1, 2013.
Office Action for CN Patent Application No. 200780017371.9 dated Jul. 3, 2013 (with English translation).
Office Action for MX Patent Application No. MX/a/2012/002011 dated Jul. 17, 2013 (with English translation).
Amendment (amending specification) for AU Patent Application No. 2012246490 dated Aug. 2, 2013.
Response to Office Action for EP Application No. 11798224.9 dated Aug. 2, 2013.
Nishio et al., "Phase 1 study of lenvatinib combined with carboplatin and paclitaxel in patients with non-small-cell lung cancer", British Journal of Cancer (2013), 109:538-544.
Amendment submitted for Korean Application No. 10-2008-7013685 dated Jul. 5, 2013 (with English translation).
Voluntary amendment for CA Patent Application No. 2704000 dated Aug. 6, 2013.
Amendment filed for JP Patent Application 2008-532141 dated Jul. 5, 2013 (with English translation).
Demand for Appeal Trial for JP Patent Application 2008-532141 dated Jul. 5, 2013 (with English translation).
Notice of Allowance for IL Patent Application No. 175363 dated Aug. 13, 2013 (with English translation).
Amendment filed for EP Application No. 12774278.1 dated Aug. 13, 2013.
Office Action for IL Patent Application No. 200090 dated Jul. 24, 2013 with English translation.
Response to Office Action for U.S. Appl. No. 12/439,339 dated Aug. 22, 2013.
Communication to the Patent Office for CL Application No. 2012-00412 dated Aug. 31, 2012 (with English translation).
Communication to the Patent Office for AR Application No. P110100513 dated Aug. 27, 2013 (with English translation).
Notice of Allowance for U.S. Appl. No. 12/741,682 dated Jun. 19, 2013.
RCE and IDS filed for U.S. Appl. No. 13/083,338, filed Aug. 28, 2013.
Office Action for U.S. Appl. No. 13/238,085 dated Sep. 6, 2013.
Corrected English Translation for Office Action for JP Patent Application No. 2007-529565 dated Aug. 7, 2012.

(56) References Cited

OTHER PUBLICATIONS

Response to Office Action for MX Patent Application No. MX/a/2012/002011 dated Aug. 29, 2013 (with English Translation).
Final Office Action for U.S. Appl. No. 12/039,381 dated Sep. 12, 2013.
Preliminary Amendment for U.S. Appl. No. 14/002,018, filed Aug. 28, 2013.
Amended Claims for RU Patent Application No. 2013140169 dated Aug. 29, 2013 (with English translation).
Notice of Allowance for CN Application No. 200880115011.7 dated Aug. 5, 2013 (with English translation).
Amendment filed for JP Patent Application No. 2009-551518 dated Aug. 6, 2013 (with English translation).
Argument filed for JP Patent Application No. 2009-551518 dated Aug. 6, 2013 (partial English translation).
Response to Office Action for CA Patent Application No. 2652442 dated Sep. 5, 2013.
Amendment to claims for IN Patent Application No. 7026/CHENP/2013 dated Sep. 5, 2013.
Amendment filed for JP Patent Application No. 2009-540099 dated Aug. 13, 2013 (with English translation).
Argument filed for JP Patent Application No. 2009-540099 dated Aug. 13, 2013 (with partial English translation).
Preliminary Amendment filed for U.S. Appl. No. 13/805,826 dated Sep. 9, 2013.
Request for Continued Examination and Information Disclosure Statement for U.S. Appl. No. 13/205,328 dated Sep. 10, 2013.
Notice of Allowance for JP Patent Application No. P2008-532141 dated Sep. 10, 2013 (with English translation).
Amendments for CN Patent Application No. 201280010898.X dated Aug. 29, 2013 (with English translation).
Notice of Allowance for U.S. Appl. No. 13/624,278 dated Sep. 16, 2013.
Notice of Allowance for EP Patent Application No. 04818213.3 dated Sep. 19, 2013.
Request for Continued Examination and Information Disclosure Statement for U.S. Appl. No. 12/741,682, filed Sep. 19, 2013.
Amendment of Specification for AU Patent Application No. 2011270165 dated Sep. 23, 2013.
Office Action for PH Application No. 1-2011-502441 dated Oct. 1, 2013.
Amendment for IN Patent Application No. 10502/CHENP/2012 dated Oct. 1, 2013.
Response to Opposition for CL Patent Application No. 2012-00412 dated Oct. 2, 2013 (with English translation).
Office Action for KR 10-2008-7029472 dated Sep. 30, 2013 (in Korean).
Office Action for Kr 10-2008-7029472 dated Sep. 30, 2013 (in English).
Ezzat et al., "Dual Inhibition of RET and FGFR4 Restraints Medullary Thyroid Cancer Cell Growth", Clinical Cancer Research, 11:1336-1341 (2005).
Sattler et al., "Targeting c-Kit mutations: basic science to novel therapies", Leukemia Research, 28S1:S11-S20 (2004).
Office Action for KR 10-2009-7005657 dated Sep. 30, 2013 (in English).
Office Action for KR10-2009-70056572 dated Sep. 30, 2013 (in Korean).
Response to Restriction Requirement for U.S. Appl. No. 13/238,085, filed Oct. 4, 2013.
Amendment for KR Patent Application No. 10-2012-7033886 dated Sep. 27, 2013 (with English translation).
Office Action for U.S. Appl. No. 11/997,543 dated Sep. 30, 2013.
Office Action for CO Patent Application No. 12/022,608 dated Oct. 7, 2013 (with English translation).
Notice of Allowance for U.S. Appl. No. 13/083,338 dated Sep. 26, 2013.
Amendment for IL Patent Application No. 200090 dated Oct. 2, 2013 (in English).
St. Bernard et al., "Fibroblast Growth Factor Receptors as Molecular Targets in Thyroid Carcinoma", Endocrinology, 146(3):1145-1153 (2005).
Amendment filed for CA Patent Application No. 2828946 dated Aug. 30, 2013.
Notice of Allowance for U.S. Appl. No. 11/997,719 dated Sep. 13, 2013.
Amendment filed for RU Patent Application No. 2012158142 dated Oct. 17, 2013 (with English translation).
Amendment filed for MX Patent Application No. MX/a/2012/014776 dated Oct. 21, 2013 (with English translation).
Office Action for IN Application No. 6415/CHENP/2008 dated Oct. 3, 2013.
Request for Re-examination for CN Patent Application No. 200780017371.9 dated Oct. 11, 2013 (with English translation).
Office Action for MX Patent Application No. MX/a/2010/008187 dated Aug. 21, 2013 (with English translation).
RCE filed for U.S. Appl. No. 12/524,754, filed Oct. 18, 2013.
Request for Examination and Voluntary Amendment for CA Patent Application No. 2713930 dated Oct. 21, 2013.
Notice of Allowance for U.S. Appl. No. 12/741,682 dated Oct. 21, 2013.
Response to Office Action for IN Application No. 1571/CHENP/2007 dated Oct. 30, 2013.
RCE and Response to Final Office Action for U.S. Appl. No. 12/039,381 dated Oct. 23, 2013.
Response to Office Action for MX Patent Application No. MX/a/2010/008187 dated Nov. 4, 2013 (with English Translation).
Response to Office Action for PH Application No. 1-2011-502441 dated Nov. 4, 2013.
IPRP for PCT/JP2012/060279 dated Oct. 31, 2013.
Notice of Allowance for U.S. Appl. No. 12/439,339 dated Nov. 7, 2013.
Notice of Allowance for JP Patent Application No. P2009-551518 dated Oct. 22, 2013 (with English translation).
Office Action for U.S. Appl. No. 13/238,085 dated Nov. 12, 2013.
Office Action for CA Patent Application No. 2652442 dated Oct. 4, 2013.
Response to Office Action for CO Patent Application No. 12-022608 dated Nov. 13, 2013 (with English translation).
Amendment for BR Patent Application No. 112012032462-4 dated Nov. 4, 2013 (with English translation).
Wang, Y., "Drugs of Today, Everolimus in renal cell carcinoma", Journals of the Web, 46(8):Abstract, Aug. 2010.
Office Action for CN Patent Application No. 201180030568.2 dated Oct. 12, 2013 (with English translation).
Office Action for IN Patent Application No. 1571/CHENP/2007 dated Oct. 23, 2013.
Office Action for IL Patent Application No. 205512 dated Oct. 28, 2013 (with English translation).
Notice of Allowance for U.S. Appl. No. 12/524,754 dated Nov. 22, 2013.
Preliminary Amendment filed for U.S. Appl. No. 14/117, 276, filed Nov. 12, 2013.
Preliminary Amendment filed for EP Patent Application No. 12786619.2 dated Nov. 13, 2013.
Voluntary amendment filed for CA Patent Application No. 2802644 dated Nov. 22, 2013.
Amendment filed for KR Patent Application No. 10-2008-7029472 dated Nov. 20, 2013 (with English translation).
Amendment filed for EP Application No. 12793322.4 dated Nov. 28, 2013.
Request for Continued Examination and Information Disclosure Statement filed for U.S. Appl. No. 13/083,338 dated Dec. 2, 2013.
Amendment for KR Patent Application No. 10-2013-7020616 dated Nov. 22, 2013 (with English translation).
IPRP of International Patent Application No. PCT-JP2012-062509 dated Nov. 28, 2013.
Decision of Patent Grant for KR Patent Application No. 10-2008-7013685 dated Nov. 29, 2013 (with English translation).
Office Action for IN Patent Application No. 1571/CHENP/2007 dated Dec. 9, 2013.

(56) References Cited

OTHER PUBLICATIONS

Preliminary Amendment filed for U.S. Appl. No. 14/122,339 dated Nov. 26, 2013.
Response filed for KR Application No. 10-2009-7005657 dated Nov. 21, 2013 (with English translation).
Notice of Allowance for IL Patent Application No. 200090 dated Nov. 18, 2013 (with English translation).
Office Action for MX Patent Application No. MX/a/2012/002011 dated Nov. 21, 2013 (with English translation).
Office Action for CN Patent Application No. 200680020317.5 dated Nov. 28, 2013 (with English translation).
Request for Continued Examination filed for U.S. Appl. No. 11/997,719 dated Dec. 11, 2013.
Request for Continued Examination filed for U.S. Appl. No. 13/624,278 dated Dec. 13, 2013.
Almarsson et al., "High-Throughput Surveys of Cyrstal Form Diversity of Highly Polymorphic Pharmaceutical Compounds", Crystal Growth & Design, pp. 927-933 (2003).
Amendment for CO Application No. 12-022608 dated Jan. 28, 2014 (with English translation).
Amendment for IN Patent Application No. 1571/CHENP/2007 dated Jan. 23, 2014.
Amendment to Specification for KR Patent Application No. 10-2009-7017694 dated Feb. 28, 2014 (with English translation).
Argument for KR Patent Application No. 10-2009-7017694 dated Feb. 28, 2014 (with English translation).
European Search Report for EP 11798224.9 dated Mar. 4, 2014.
International Preliminary Report (IPRP) for PCT/US2012/040183 dated Apr. 3, 2014.
Notice of Allowance for U.S. Appl. No. 12/439,339 dated Apr. 1, 2014.
Notice of Allowance for U.S. Appl. No. 12/741,682 dated Feb. 7, 2014.
Notice of Allowance for U.S. Appl. No. 13/083,338 dated Feb. 6, 2014.
Notice of Allowance for U.S. Appl. No. 12/524,754 dated Feb. 13, 2014.
Office Action for CA Application No. 2676796 dated Dec. 30, 2013.
Office Action for CN Application No. 200680020317.5 dated Mar. 4, 2014 (with English translation).
Office Action for CN Application No. 201180030568.2 dated Mar. 24, 2014 (with English translation).
Office Action for EP Application No. 04807580.8 dated Mar. 18, 2014.
Office Action for European Patent Application No. 08704376.6 dated Feb. 24, 2014.
Office Action for JP Application No. P2009-540099 dated Mar. 25, 2014 (with English translation).
Office Action for KR Application No. 10-2008-7029472 dated Mar. 28, 2014 (with English translation).
Office Action for KR Application No. 10-2009-7005657 dated Mar. 28, 2014 (with English translation).
Office Action for KR Application No. 10-2009-7017694 dated Jan. 29, 2014 (with English translation).
Office Action for PH Application No. 1-2011-502441 dated Feb. 19, 2014.
Office Action for U.S. Appl. No. 12/039,381 dated Jan. 9, 2014.
Office Action for U.S. Appl. No. 13/805,826 dated Apr. 2, 2014.
Office Action for U.S. Appl. No. 13/923,858 dated Apr. 18, 2014.
Office Action for U.S. Appl. No. 14/002,018 dated Apr. 14, 2014.
Office Action for U.S. Appl. No. 11/997,543 dated Mar. 11, 2014.
Office Action for U.S. Appl. No. 11/662,425 dated Feb. 27, 2014.
Office Action for VN Application No. 1-2011-03484 dated Dec. 31, 2013 (with English translation).
Office Action of CO Patent Application No. 12-022608 Dec. 17, 2013 (with English translation).
Office Action of IL Patent Application No. 207089 dated Nov. 25, 2013 (with English translation).
Office Action of MX Patent Application No. MX-a-2010-008187 dated Dec. 5, 2013 (with English translation).
O'Reilly et al., "Hydrolysis of tert-Butyl Methyl Ether(MTBE) in Dilute Aqueous Acid", Environ.Sci.Technol; 35, 2001, pp. 3954-3961.
Patel et al., "The effect of excipients on the stability of levothyroxine sodium pentahydrate tables", International Journal of Pharmaceutics; 264, pp. 35-43 (2003).
Request for Continued Examination for U.S. Appl. No. 12/439,339 dated Jan. 27, 2014.
Request for Continued Examination for U.S. Appl. No. 12/741,682 dated Jan. 17, 2014.
Request for Continued Examination for U.S. Appl. No. 12/524,754 dated Feb. 3, 2013.
Response filed for IN Patent Application No. 6415/CHENP/2008 dated Jan. 17, 2014.
Reponse to Office Action and Information Disclosure Statement filed for U.S. Appl. No. 11/997,543 date Dec. 19, 2013.
Response to Office Action for CA Patent Application No. 2652442 dated Jan. 8, 2014.
Response to Office Action for CN 2006800203175 filed on Jan. 9, 2014 (with English translation).
Response to Office Action for MX Patent Application No. MX/a/2010008187 dated Feb. 17, 2014 (with English translation).
Response to Office Action for MX-a-2012-002011 dated Jan. 16, 2014 (with English translation).
Response to Office Action for Philippines Patent Application No. 10-2011-502441 dated Feb. 28, 2014.
Response to Office Action for U.S. Appl. No. 12/039,381 dated Apr. 3, 2014.
Response to CN Application No. 201180030568.2 dated Jan. 13, 2014 (with English translation).
Search Report for EP Patent Application No. 11798224.9 dated Mar. 21, 2014.
Stahl and Wermuth, Handbook of Pharmaceutical Salts: Properties, Selection and Use, pp. 117-122 (2002).
Submission for VN Application No. 1-2011-03484 dated Feb. 28, 2014 (with English translation).
Winkler et al., "Kinetics of vascular normalization by VEGFR2 blockade governs brain tumor response to radiation: Role of oxygenation, angiopoietin-1, and matrix metalloproteinases", Cancer Cell vol. 6:553-563 (2004).
Xiaotian Zhang et al. "Synergic antiproliferative effect of DNA methyltransferase inhibitor in combination with anticancer drugs in gastric carcinoma", Cancer Science, vol. 97, No. 9, Sep. 2006, pp. 938-944.

\* cited by examiner

USE OF COMBINATION OF ANTI-ANGIOGENIC SUBSTANCE AND C-KIT KINASE INHIBITOR

CROSS-REFERENCE TO RELATED APPLICATIONS

This is a divisional of application Ser. No. 12/092,539 filed in the United States Patent and Trademark Office on May 2, 2008 now abandoned as the 371 National Phase of International patent application No. PCT/JP2006/322514 filed on Nov. 7, 2006, which claims priority to application no. JP 2005-322946 filed in Japan on Nov. 7, 2005. Each of these prior applications is hereby incorporated by reference and in its entirety.

FIELD OF THE INVENTION

The present invention relates to a pharmaceutical composition and a kit comprising a combination of a compound represented by Formula (I), a pharmacologically acceptable salt thereof or a solvate thereof (hereinafter, also referred to as a "compound of the invention") and a substance having a c-kit kinase-inhibiting activity (hereinafter, also referred to as a "c-kit inhibitor"), to a method for treating cancer comprising administering an effective amount of the pharmaceutical composition to a patient, to use of the compound of the invention for producing the pharmaceutical composition, and to the compound of the invention used for the pharmaceutical composition.

BACKGROUND OF THE INVENTION

Examples of conventionally used chemotherapeutic agents for cancer include alkylating agents such as cyclophosphamide, antimetabolites such as methotrexate and fluorouracil, antibiotics such as adriamycin, mitomycin and bleomycin, plant-derived taxol, vincristine and etoposide and metal complexes such as cisplatin. None of them, however, provides sufficient antitumor effect, and thus development of a novel antitumor drug has been strongly desired.

Recently, 4-(4-methylpiperazine-1-ylmethyl)-N-[4-methyl-3-[4-(3-pyridyl)pyrimidine-2-ylamino]phenyl]benzenamide (hereinafter, also referred to as "imatinib" or "STI571") is known as a c-kit inhibitor (Documents 1 and 2).

In addition, 4-(3-chloro-4-(cyclopropylaminocarbonyl)aminophenoxy)-7-methoxy-6-quinolinecarboxamide is known as a VEGF receptor kinase inhibitor (Document 3-4).

However, it has not been elucidated yet what kind of antitumor effect can or cannot be obtained with a pharmaceutical composition containing a combination of these substances.

DOCUMENTS

1. Blood, 96, 925-932, 2000.
2. J Clin Oncol., 20, 1692-1703, 2002.
3. International publication No. 02/32872 (pamphlet)
4. International publication No. 2005/063713 (pamphlet)

DISCLOSURE OF THE INVENTION

The present invention was achieved regarding the circumstances described above. The problem to be solved by the invention is to find a pharmaceutical composition having an excellent antitumor effect and a method for treating cancer.

In order to solve the above problem, the present inventors have gone through keen examination, as a result of which combined use of 4-(3-chloro-4-(cyclopropylaminocarbonyl)aminophenoxy)-7-methoxy-6-quinolinecarboxamide and c-kit inhibitor imatinib was found to show an excellent antitumor effect.

Thus, the present invention relates to:

(1) a pharmaceutical composition comprising a combination of a compound represented by Formula (I), a pharmacologically acceptable salt thereof or a solvate thereof and a substance having a c-kit kinase-inhibiting activity.

(2) A kit comprising: (a) at least one selected from the group consisting of a package, an instruction and an attached document describing combined use of a compound represented by Formula (I), a pharmacologically acceptable salt thereof or a solvate thereof and a substance having a c-kit kinase-inhibiting activity; and (b) a pharmaceutical composition comprising a compound represented by Formula (I), a pharmacologically acceptable salt thereof or a solvate thereof.

(3) A kit comprising a set of a formulation containing a compound represented by Formula (I), a pharmacologically acceptable salt thereof or a solvate thereof, and a formulation containing a substance having a c-kit kinase-inhibiting activity.

(4) A pharmaceutical composition comprising a compound represented by Formula (I), a pharmacologically acceptable salt thereof or a solvate thereof, which is administered to a patient with a substance having a c-kit kinase-inhibiting activity.

(5) A method for treating cancer comprising administering an effective amount of a compound represented by Formula (I), a pharmacologically acceptable salt thereof or a solvate thereof and an effective amount of a substance having a c-kit kinase-inhibiting activity to a patient.

(6) Use of a compound represented by Formula (I), a pharmacologically acceptable salt thereof or a solvate thereof for producing a pharmaceutical composition in combination with a substance having a c-kit kinase-inhibiting activity.

(7) A compound represented by Formula (I), a pharmacologically acceptable salt thereof or a solvate thereof used for a pharmaceutical composition in combination with a substance having a c-kit kinase-inhibiting activity.

The compound represented by Formula (I), a pharmacologically acceptable salt thereof or a solvate thereof is as follows:

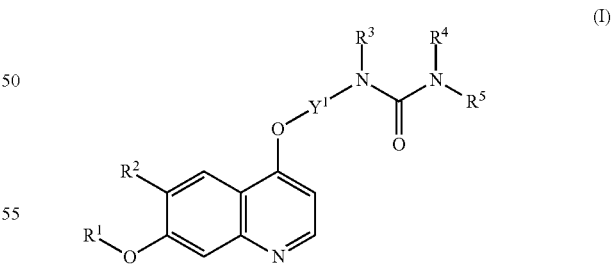

[wherein, $R^1$ represents group represented by Formula -$V^1$-$V^2$-$V^3$ (wherein, $V^1$ represents $C_{1-6}$ alkylene group that may have a substituent; $V^2$ represents a single bond, an oxygen atom, a sulfur atom, carbonyl group, sulfinyl group, sulfonyl group, group represented by Formula —$CONR^6$—, group represented by Formula —$SO_2NR^6$—, group represented by Formula —$NR^6SO_2$—, group represented by Formula —$NR^6CO$— or group represented by Formula —$NR^6$— (wherein, $R^6$ represents a hydrogen atom, $C_{1-6}$ alkyl group that may have a substituent or $C_{3-8}$ cycloalkyl group that may have a substituent); $V^3$ represents a hydrogen atom, $C_{1-6}$ alkyl group that may have a substituent, $C_{2-6}$ alkenyl group that may have a substituent, $C_{2-6}$ alkynyl group that may have a substituent, $C_{3-8}$ cycloalkyl group that may have a substituent, $C_{6-10}$ aryl group that may have a substituent, 5-10-membered heteroaryl group that may have a substituent or 3-10-membered nonaromatic heterocyclic group that may have a substituent);

$R^2$ represents cyano group, $C_{1-6}$ alkoxy group that may have a substituent, carboxyl group, $C_{2-7}$ alkoxycarbonyl group that may have a substituent or group represented by Formula —$CONV^{a11}V^{a12}$ (wherein, $V^{a11}$ represents a hydrogen atom, $C_{1-6}$ alkyl group that may have a substituent, $C_{2-6}$ alkenyl group that may have a substituent, $C_{2-6}$ alkynyl group that may have a substituent, $C_{3-8}$ cycloalkyl group that may have a substituent, $C_{6-10}$ aryl group that may have a substituent, 5-10-membered heteroaryl group that may have a substituent or 3-10-membered nonaromatic heterocyclic group that may have a substituent; $V^{a12}$ represents a hydrogen atom, $C_{1-6}$ alkyl group that may have a substituent, $C_{2-6}$ alkenyl group that may have a substituent, $C_{2-6}$ alkynyl group that may have a substituent, $C_{3-8}$ cycloalkyl group that may have a substituent, $C_{6-10}$ aryl group that may have a substituent, 5-10-membered heteroaryl group that may have a substituent, 3-10-membered nonaromatic heterocyclic group that may have a substituent, hydroxyl group, $C_{1-6}$ alkoxy group that may have a substituent or $C_{3-8}$ cycloalkoxy group that may have a substituent);

$Y^1$ represents group represented by Formula

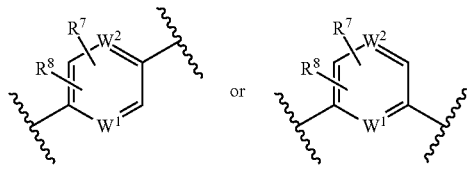

(wherein, $R^7$ and $R^8$ each independently represent a hydrogen atom, a halogen atom, cyano group, nitro group, amino group, $C_{1-6}$ alkyl group that may have a substituent, $C_{3-8}$ cycloalkyl group that may have a substituent, $C_{1-6}$ alkoxy group that may have a substituent, $C_{1-6}$ alkylthio group that may have a substituent, formyl group, $C_{2-7}$ acyl group that may have a substituent, $C_{2-7}$ alkoxycarbonyl group that may have a substituent or group represented by Formula —$CONV^{d1}V^{d2}$ (wherein, $V^{d1}$ and $V^{d2}$ each independently represent a hydrogen atom or $C_{1-6}$ alkyl group that may have a substituent);

$W^1$ and $W^2$ each independently represent a carbon atom or a nitrogen atom that may have a substituent);

$R^3$ and $R^4$ each independently represent a hydrogen atom, $C_{1-6}$ alkyl group that may have a substituent, $C_{2-6}$ alkenyl group that may have a substituent, $C_{2-6}$ alkynyl group that may have a substituent, $C_{3-8}$ cycloalkyl group that may have a substituent, $C_{2-7}$ acyl group that may have a substituent or $C_{2-7}$ alkoxycarbonyl group that may have a substituent;

$R^5$ represents a hydrogen atom, $C_{1-6}$ alkyl group that may have a substituent, $C_{2-6}$ alkenyl group that may have a substituent, $C_{2-6}$ alkynyl group that may have a substituent, $C_{3-8}$ cycloalkyl group that may have a substituent, $C_{6-10}$ aryl group that may have a substituent, 5-10-membered heteroaryl group that may have a substituent, 3-10-membered nonaromatic heterocyclic group that may have a substituent].

Furthermore, the present invention preferably relates to the followings.

(1) A pharmaceutical composition comprising a combination of 4-(3-chloro-4-(cyclopropylaminocarbonyl)aminophenoxy)-7-methoxy-6-quinolinecarboxamide, a pharmacologically acceptable salt thereof or a solvate thereof and imatinib.

(2) A kit comprising: (a) at least one selected from the group consisting of a package, an instruction and an attached document describing combined use of 4-(3-chloro-4-(cyclopropylaminocarbonyl)aminophenoxy)-7-methoxy-6-quinolinecarboxamide, a pharmacologically acceptable salt thereof or a solvate thereof and imatinib; and (b) a pharmaceutical composition comprising 4-(3-chloro-4-(cyclopropylaminocarbonyl)aminophenoxy)-7-methoxy-6-quinolinecarboxamide, a pharmacologically acceptable salt thereof or a solvate thereof.

(3) A kit comprising a set of a formulation containing 4-(3-chloro-4-(cyclopropylaminocarbonyl)aminophenoxy)-7-methoxy-6-quinolinecarboxamide, a pharmacologically acceptable salt thereof or a solvate thereof and a formulation containing imatinib.

(4) A pharmaceutical composition comprising 4-(3-chloro-4-(cyclopropylaminocarbonyl)aminophenoxy)-7-methoxy-6-quinolinecarboxamide, a pharmacologically acceptable salt thereof or a solvate thereof which is administered to a patient together with imatinib.

(5) A method for treating cancer comprising administering an effective amount of 4-(3-chloro-4-(cyclopropylaminocarbonyl)aminophenoxy)-7-methoxy-6-quinolinecarboxamide, a pharmacologically acceptable salt thereof or a solvate thereof and an effective amount of imatinib to a patient.

(6) Use of 4-(3-chloro-4-(cyclopropylaminocarbonyl)aminophenoxy)-7-methoxy-6-quinolinecarboxamide, a pharmacologically acceptable salt thereof or a solvate thereof for producing a pharmaceutical composition in combination with imatinib.

(7) 4-(3-chloro-4-(cyclopropylaminocarbonyl)aminophenoxy)-7-methoxy-6-quinolinecarboxamide, a pharmacologically acceptable salt thereof or a solvate thereof for producing a pharmaceutical composition in combination with imatinib.

According to the present invention, a pharmaceutical composition comprising a combination of a compound represented by Formula (I), a pharmacologically acceptable salt thereof or a solvate thereof and a c-kit inhibitor is provided, which can be used for treating cancer.

BRIEF DESCRIPTION OF DRAWINGS

In FIG. 1, Compound A refers to 4-(3-chloro-4-(cyclopropylaminocarbonyl)aminophenoxy)-7-methoxy-6-quinolinecarboxamide and Compound B refers to imatinib.

In FIG. 2, Compound A refers to 4-(3-chloro-4-(cyclopropylaminocarbonyl)aminophenoxy)-7-methoxy-6-quinolinecarboxamide and Compound B refers to imatinib.

BEST MODES FOR CARRYING OUT THE INVENTION

Figure 1:
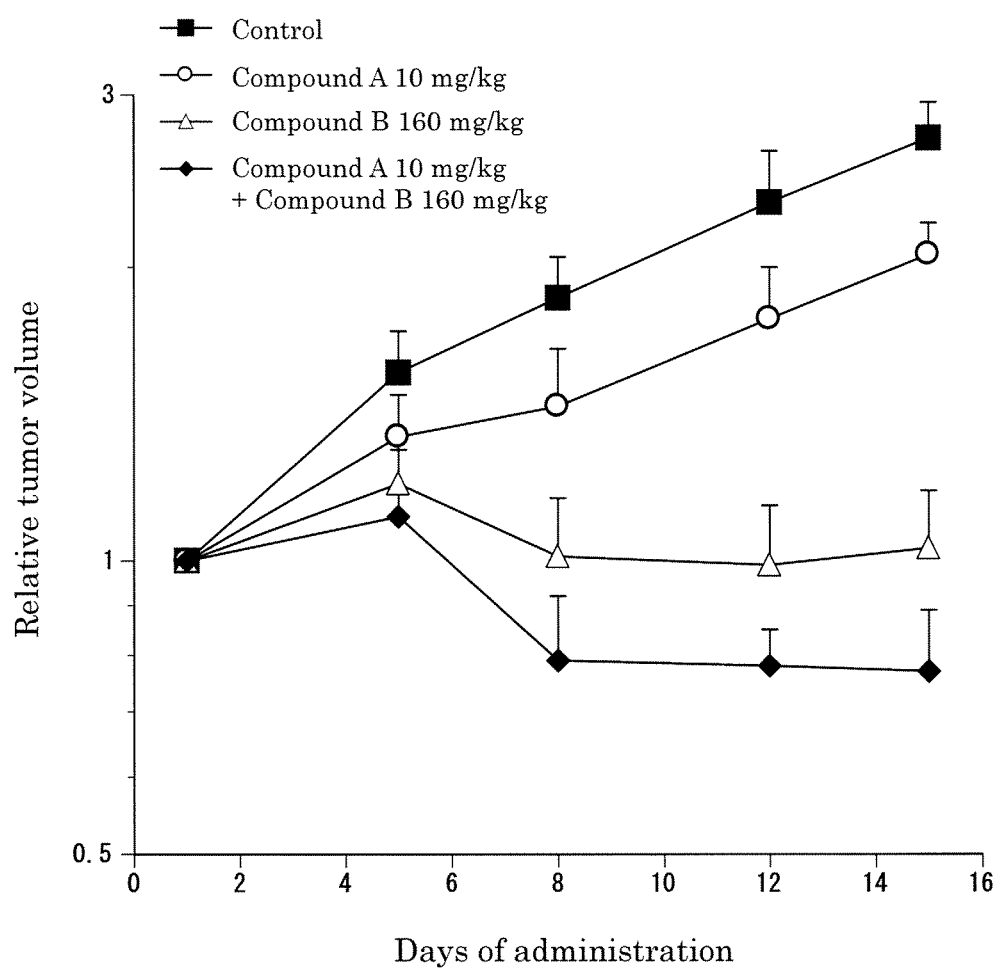
FIG. 1 shows the combined effect of a VEGF receptor kinase inhibitor and a c-kit inhibitor in a human cancer cell line subcutaneous xenograft model.

Hereinafter, embodiments of the present invention will be described. The following embodiments illustrate the present invention, which are not intended to limit the present invention. The present invention may be carried out in various embodiments without departing from the scope of the invention.

The documents, laid-open patent applications, patent publications and other patent documents cited herein are incorporated herein by reference. The present specification incorporates the content of specification of Japanese Patent Application No. 2005-322946 based on which the present application claims priority.

1. Compound

Herein, "a halogen atom" refers to a fluorine atom, a chlorine atom, a bromine atom or an iodine atom.

Preferable examples of "a halogen atom" include a fluorine atom and a chlorine atom.

Herein, "$C_{1-6}$ alkyl group" refers to linear or branched alkyl group with a carbon number of 1-6, and specific examples include methyl group, ethyl group, 1-propyl group (n-propyl group), 2-propyl group (i-propyl group), 2-methyl-1-propyl group (i-butyl group), 2-methyl-2-propyl group (t-butyl group), 1-butyl group (n-butyl group), 2-butyl group (s-butyl group), 1-pentyl group, 2-pentyl group, 3-pentyl group, 2-methyl-1-butyl group, 3-methyl-1-butyl group, 2-methyl-2-butyl group, 3-methyl-2-butyl group, 2,2-dimethyl-1-propyl group, 1-hexyl group, 2-hexyl group, 3-hexyl group, 2-methyl-1-pentyl group, 3-methyl-1-pentyl group, 4-methyl-1-pentyl group, 2-methyl-2-pentyl group, 3-methyl-2-pentyl group, 4-methyl-2-pentyl group, 2-methyl-3-pentyl group, 3-methyl-3-pentyl group, 2,3-dimethyl-1-butyl group, 3,3-dimethyl-1-butyl group, 2,2-dimethyl-1-butyl group, 2-ethyl-1-butyl group, 3,3-dimethyl-2-butyl group and 2,3-dimethyl-2-butyl group.

Preferable examples of "$C_{1-6}$ alkyl group" include methyl group, ethyl group, 1-propyl group, 2-propyl group, 2-methyl-1-propyl group, 2-methyl-2-propyl group 1-butyl group and 2-butyl group.

Herein, "$C_{1-6}$ alkylene group" refers to divalent group derived from the "$C_{1-6}$ alkyl group" defined above by removing any one hydrogen atom therefrom, and specific examples include methylene group, 1,2-ethylene group, 1,1-ethylene group, 1,3-propylene group, tetramethylene group, pentamethylene group and hexamethylene group.

Herein, "$C_{2-6}$ alkenyl group" refers to linear or branched alkenyl group having one double bond and a carbon number of 2-6, and specific examples include ethenyl group (vinyl group), 1-propenyl group, 2-propenyl group (allyl group), 1-butenyl group, 2-butenyl group, 3-butenyl group, pentenyl group and hexenyl group.

Herein, "$C_{2-6}$ alkynyl group" refers to linear or branched alkynyl group having one triple bond and a carbon number of 2-6, and specific examples include ethynyl group, 1-propynyl group, 2-propynyl group, 1-butynyl group, 2-butynyl group, 3-butynyl group, pentynyl group and hexynyl group.

Herein, "$C_{3-8}$ cycloalkyl group" refers to monocyclic or bicyclic saturated aliphatic hydrocarbon group with a carbon number of 3-8, and specific examples include cyclopropyl group, cyclobutyl group, cyclopentyl group, cyclohexyl group, cycloheptyl group, cyclooctyl group, bicyclo[2.1.0]pentyl group, bicyclo[3.1.0]hexyl group, bicyclo[2.1.1]hexyl group, bicyclo[4.1.0]heptyl group, bicyclo[2.2.1]heptyl group (norbornyl group), bicyclo[3.3.0]octyl group, bicyclo[3.2.1]octyl group and bicyclo[2.2.2]octyl group.

Preferable examples of "$C_{3-8}$ cycloalkyl group" include cyclopropyl group, cyclobutyl group and cyclopentyl group.

Herein, "$C_{6-10}$ aryl group" refers to aromatic hydrocarbon cyclic group with a carbon number of 6-10, and specific examples include phenyl group, 1-naphthyl group, 2-naphthyl group, indenyl group and azulenyl group.

A preferable example of "$C_{6-10}$ aryl group" includes phenyl group.

Herein, "a heteroatom" refers to a nitrogen atom, an oxygen atom or a sulfur atom.

Herein, "5-10-membered heteroaryl group" refers to aromatic cyclic group having 5-10 atoms forming the ring and 1-5 heteroatoms included in the atom forming the ring, and specific examples include furyl group, thienyl group, pyrrolyl group, imidazolyl group, triazolyl group, tetrazolyl group, thiazolyl group, pyrazolyl group, oxazolyl group, isoxazolyl group, isothiazolyl group, furazanyl group, thiadiazolyl group, oxadiazolyl group, pyridyl group, pyrazinyl group, pyridazinyl group, pyrimidinyl group, triazinyl group, purinyl group, pteridinyl group, quinolyl group, isoquinolyl group, naphthiridinyl group, quinoxalinyl group, cinnolinyl group, quinazolinyl group, phthalazinyl group, imidazopyridyl group, imidazothiazolyl group, imidazoxazolyl group, benzothiazolyl group, benzoxazolyl group, benzimidazolyl group, indolyl group, isoindolyl group, indazolyl group, pyrrolopyridyl group, thienopyridyl group, furopyridyl group, benzothiadiazolyl group, benzoxadiazolyl group, pyridopyrimidinyl group, benzofuryl group, benzothienyl group and thienofuryl group.

Preferable examples of "5-10-membered heteroaryl group" include furyl group, thienyl group, pyrrolyl group, imidazolyl group, thiazolyl group, pyrazolyl group, oxazolyl group, isoxazolyl group, isothiazolyl group, pyridyl group and pyrimidinyl group.

Herein, "3-10-membered nonaromatic heterocyclic group":

(1) has 3-10 atoms forming the ring;

(2) has 1-2 heteroatoms included in the atoms forming the ring;

(3) may include 1-2 double bonds in the ring;

(4) may have 1-3 carbonyl group, sulfinyl group or sulfonyl group in the ring; and (5) is nonaromatic monocyclic or bicyclic group. When a nitrogen atom is included in the atoms forming the ring, the nitrogen atom may have a binding hand. Specific examples include aziridinyl group, azetidinyl group, pyrrolidinyl group, piperidinyl group, azepanyl group, azocanyl group, piperazinyl group, diazepanyl group, diazocanyl group, diazabicyclo[2.2.1]heptyl group, morpholinyl group, thiomorpholinyl group, 1,1-dioxothiomorpholinyl group, oxiranyl group, oxetanyl group, tetrahydrofuryl group, dioxoranyl group, tetrahydropyranyl group, dioxanyl group, tetrahydrothienyl group, tetrahydrothiopyranyl group, oxazolidinyl group and thiazolidinyl group.

Preferable examples of "3-10-membered nonaromatic heterocyclic group" include aziridinyl group, azetidinyl group, pyrrolidinyl group, piperidinyl group, azepanyl group, piperazinyl group, diazepanyl group, morpholinyl group, thiomorpholinyl group, 1,1-dioxothiomorpholinyl group, tetrahydrofuryl group and tetrahydropyranyl group.

Herein, "$C_{1-6}$ alkoxy group" refers to group in which an oxygen atom is bound to the terminal of "$C_{1-6}$ alkyl group" defined above, and specific examples include methoxy group, ethoxy group, 1-propoxy group (n-propoxy group), 2-propoxy group (i-propoxy group), 2-methyl-1-propoxy group (i-butoxy group), 2-methyl-2-propoxy group (t-butoxy group), 1-butoxy group (n-butoxy group), 2-butoxy group (s-butoxy group), 1-pentyloxy group, 2-pentyloxy group, 3-pentyloxy group, 2-methyl-1-butoxy group, 3-methyl-1-butoxy group, 2-methyl-2-butoxy group, 3-methyl-2-butoxy group, 2,2-dimethyl-1-propoxy group, 1-hexyloxy group, 2-hexyloxy group, 3-hexyloxy group, 2-methyl-1-pentyloxy group, 3-methyl-1-pentyloxy group, 4-methyl-1-pentyloxy group, 2-methyl-2-pentyloxy group, 3-methyl-2-pentyloxy group, 4-methyl-2-pentyloxy group, 2-methyl-3-pentyloxy group, 3-methyl-3-pentyloxy group, 2,3-dimethyl-1-butoxy group, 3,3-dimethyl-1-butoxy group, 2,2-dimethyl-1-butoxy group, 2-ethyl-1-butoxy group, 3,3-dimethyl-2-butoxy group and 2,3-dimethyl-2-butoxy group.

Preferable examples of "$C_{1-6}$ alkoxy group" include methoxy group, ethoxy group, 1-propoxy group, 2-propoxy group, 2-methyl-1-propoxy group, 2-methyl-2-propoxy group, 1-butoxy group and 2-butoxy group.

Herein, "$C_{1-6}$ alkylthio group" refers to group in which a sulfur atom is bound to the terminal of "$C_{1-6}$ alkyl group" defined above, and specific examples include methylthio group, ethylthio group, 1-propylthio group (n-propylthio group), 2-propylthio group (i-propylthio group), 2-methyl-1-propylthio group (i-butylthio group), 2-methyl-2-propylthio group (t-butylthio group), 1-butylthio group (n-butylthio group), 2-butylthio group (s-butylthio group), 1-pentylthio group, 2-pentylthio group, 3-pentylthio group, 2-methyl-1-butylthio group, 3-methyl-1-butylthio group, 2-methyl-2-butylthio group, 3-methyl-2-butylthio group, 2,2-dimethyl-1-propylthio group, 1-hexylthio group, 2-hexylthio group, 3-hexylthio group, 2-methyl-1-pentylthio group, 3-methyl-1-pentylthio group, 4-methyl-1-pentylthio group, 2-methyl-2-pentylthio group, 3-methyl-2-pentylthio group, 4-methyl-2-pentylthio group, 2-methyl-3-pentylthio group, 3-methyl-3-pentylthio group, 2,3-dimethyl-1-butylthio group, 3,3-dimethyl-1-butylthio group, 2,2-dimethyl-1-butylthio group, 2-ethyl-1-butylthio group, 3,3-dimethyl-2-butylthio group and 2,3-dimethyl-2-butylthio group.

Preferable examples of "$C_{1-6}$ alkylthio group" include methylthio group, ethylthio group, 1-propylthio group (n-propylthio group), 2-propylthio group (i-propylthio group), 2-methyl-1-propylthio group (i-butylthio group), 2-methyl-2-propylthio group (t-butylthio group), 1-butylthio group (n-butylthio group) and 2-butylthio group (s-butylthio group).

Herein, "$C_{3-8}$ cycloalkoxy group" refers to group in which an oxygen atom is bound to the terminal of "$C_{3-8}$ cycloalkyl group" defined above, and specific examples include cyclopropoxy group, cyclobutoxy group, cyclopentyloxy group, cyclohexyloxy group, cycloheptyloxy group, cyclooctyloxy group, bicyclo[2.1.0]pentyloxy group, bicyclo[3.1.0]hexyloxy group, bicyclo[2.1.1]hexyloxy group, bicyclo[4.1.0]heptyloxy group, bicyclo[2.2.1]heptyloxy group (norbornyloxy group), bicyclo[3.3.0]octyloxy group, bicyclo[3.2.1]octyloxy group and bicyclo[2.2.2]octyloxy group.

Preferable examples of "$C_{3-8}$ cycloalkoxy group" include cyclopropoxy group, cyclobutoxy group and cyclopentyloxy group.

Herein, "mono-$C_{1-6}$ alkylamino group" refers to group in which a hydrogen atom in amino group is substituted with "$C_{1-6}$ alkyl group" defined above, and specific examples include methylamino group, ethylamino group, 1-propylamino group (n-propylamino group), 2-propylamino group (i-propylamino group), 2-methyl-1-propylamino group (i-butylamino group), 2-methyl-2-propylamino group (t-butylamino group), 1-butylamino group (n-butylamino group), 2-butylamino group (s-butylamino group), 1-pentylamino group, 2-pentylamino group, 3-pentylamino group, 2-methyl-1-butylamino group, 3-methyl-1-butylamino group, 2-methyl-2-butylamino group, 3-methyl-2-butylamino group, 2,2-dimethyl-1-propylamino group, 1-hexylamino group, 2-hexylamino group, 3-hexylamino group, 2-methyl-1-pentylamino group, 3-methyl-1-pentylamino group, 4-methyl-1-pentylamino group, 2-methyl-2-pentylamino group, 3-methyl-2-pentylamino group, 4-methyl-2-pentylamino group, 2-methyl-3-pentylamino group, 3-methyl-3-pentylamino group, 2,3-dimethyl-1-butylamino group, 3,3-dimethyl-1-butylamino group, 2,2-dimethyl-1-butylamino group, 2-ethyl-1-butylamino group, 3,3-dimethyl-2-butylamino group and 2,3-dimethyl-2-butylamino group.

Herein, "di-$C_{1-6}$ alkylamino group" refers to group in which two hydrogen atoms in amino group are substituted with identical or different "$C_{1-6}$ alkyl group" defined above, and specific examples include N,N-dimethylamino group, N,N-diethylamino group, N,N-di-n-propylamino group, N,N-di-i-propylamino group, N,N-di-n-butylamino group, N,N-di-i-butylamino group, N,N-di-s-butylamino group, N,N-di-t-butylamino group, N-ethyl-N-methylamino group, N-n-propyl-N-methylamino group, N-i-propyl-N-methylamino group, N-n-butyl-N-methylamino group, N-i-butyl-N-methylamino group, N-s-butyl-N-methylamino group and N-t-butyl-N-methylamino group.

Herein, "$C_{2-7}$ acyl group" refers to carbonyl group bound with "$C_{1-6}$ alkyl group" defined above, and specific examples include acetyl group, propionyl group, isopropionyl group, butyryl group, isobutyryl group, valeryl group, isovaleryl group and pivaloyl group.

Herein, "$C_{2-7}$ alkoxycarbonyl group" refers to carbonyl group bound with "$C_{1-6}$ alkoxy group" defined above, and specific examples include methoxycarbonyl group, ethoxycarbonyl group, 1-propyloxycarbonyl group, 2-propyloxycarbonyl group and 2-methyl-2-propoxy group.

Herein, "that may have a substituent" means "that may have one or more substituents in any combination at substitutable positions", and specific examples include a halogen atom, hydroxyl group, thiol group, nitro group, cyano group, formyl group, carboxyl group, amino group, silyl group, methanesulfonyl group, $C_{1-6}$ alkyl group, $C_{2-6}$ alkenyl group, $C_{2-6}$ alkynyl group, $C_{3-8}$ cycloalkyl group, $C_{6-10}$ aryl group, 5-10-membered heteroaryl group, 3-10-membered nonaromatic heterocyclic group, $C_{1-6}$ alkoxy group, $C_{1-6}$ alkylthio group, $C_{3-8}$ cycloalkoxy group, mono-$C_{1-6}$ alkylamino group, di-$C_{1-6}$ alkylamino group, $C_{2-7}$ acyl group and $C_{2-7}$ alkoxycarbonyl group. In this case, $C_{1-6}$ alkyl group, $C_{2-6}$ alkenyl group, $C_{2-6}$ alkynyl group, $C_{3-8}$ cycloalkyl group, $C_{6-10}$ aryl group, 5-10-membered heteroaryl group, 3-10-membered nonaromatic heterocyclic group, $C_{1-6}$ alkoxy group, $C_{1-6}$ alkylthio group, $C_{3-8}$ cycloalkoxy group, mono-$C_{1-6}$ alkylamino group, di-$C_{1-6}$ alkylamino group, $C_{2-7}$ acyl group and $C_{2-7}$ alkoxycarbonyl group may each independently have 1-3 groups selected from the group consisting from the following substituent groups.

<Substituent Groups>

A halogen atom, hydroxyl group, thiol group, nitro group, cyano group, $C_{1-6}$ alkyl group, $C_{3-8}$ cycloalkyl group, $C_{2-6}$ alkenyl group, $C_{2-6}$ alkynyl group, $C_{6-10}$ aryl group, 5-10- membered heteroaryl group, 3-10-membered nonaromatic heterocyclic group, $C_{1-6}$ alkoxy group and $C_{1-6}$ alkylthio group.

(A) Compound of the Invention

According to the present invention, compound represented by Formula (I) is as follows.

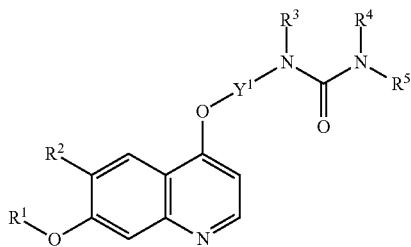

(i) $R^1$ $R^1$ represents group represented by Formula $-V^1-V^2-V^3$ (wherein, $V^1$ represents $C_{1-6}$ alkylene group that may have a substituent; $V^2$ represents a single bond, an oxygen atom, a sulfur atom, carbonyl group, sulfonyl group, sulfonyl group, group represented by Formula $-CONR^6-$, group represented by Formula $-SO_2NR^6-$, group represented by Formula $-NR^6SO_2-$, group represented by Formula $-NR^6CO-$ or group represented by Formula $-NR^6-$ (wherein, $R^6$ represents a hydrogen atom, $C_{1-6}$ alkyl group that may have a substituent or $C_{3-8}$ cycloalkyl group that may have a substituent); $V^3$ represents a hydrogen atom, $C_{1-6}$ alkyl group that may have a substituent, $C_{2-6}$ alkenyl group that may have a substituent, $C_{2-6}$ alkynyl group that may have a substituent, $C_{3-8}$ cycloalkyl group that may have a substituent, $C_{6-10}$ aryl group that may have a substituent, 5-10-membered heteroaryl group that may have a substituent or 3-10-membered nonaromatic heterocyclic group that may have a substituent).

A preferable example of $R^1$ includes $C_{1-6}$ alkyl group. In this case. $R^1$ may have a substituent selected from 3-10-membered nonaromatic heterocyclic group which may have $C_{1-6}$ alkyl group, hydroxyl group, $C_{1-6}$ alkoxy group, amino group, mono-$C_{1-6}$ alkylamino group and di-$C_{1-6}$ alkylamino group.

More preferable examples of $R^1$ include methyl group and group represented by any one of Formulae

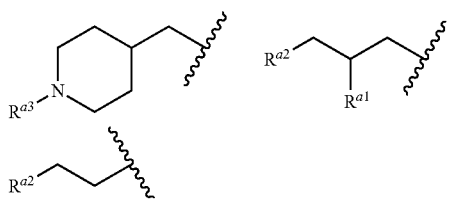

(wherein, $R^{a3}$ represents methyl group; $R^{a1}$ represents a hydrogen atom or hydroxyl group; $R^{a2}$ represents methoxy group, ethoxy group, 1-pyrrolidinyl group, 1-piperidinyl group, 4-morpholinyl group, dimethylamino group or diethylamino group).

Still more preferable examples of $R^1$ include methyl group and 2-methoxyethyl group.

(ii) $R^2$ $R^2$ represents cyano group, $C_{1-6}$ alkoxy group that may have a substituent, carboxyl group, $C_{2-7}$ alkoxycarbonyl group that may have a substituent or group represented by Formula $-CONV^{a11}V^{a12}$ (wherein, $V^{a11}$ represents a hydrogen atom, $C_{1-6}$ alkyl group that may have a substituent, $C_{2-6}$ alkenyl group that may have a substituent, $C_{2-6}$ alkynyl group that may have a substituent, $C_{3-8}$ cycloalkyl group that may have a substituent, $C_{6-10}$ aryl group that may have a substituent, 5-10-membered heteroaryl group that may have a substituent or 3-10-membered nonaromatic heterocyclic group that may have a substituent; $V^{a12}$ represents a hydrogen atom, $C_{1-6}$ alkyl group that may have a substituent, $C_{2-6}$ alkenyl group that may have a substituent, $C_{2-6}$ alkynyl group that may have a substituent, $C_{3-8}$ cycloalkyl group that may have a substituent, $C_{6-10}$ aryl group that may have a substituent, 5-10-membered heteroaryl group that may have a substituent, 3-10-membered nonaromatic heterocyclic group that may have a substituent, hydroxyl group, $C_{1-6}$ alkoxy group that may have a substituent or $C_{3-8}$ cycloalkoxy group that may have a substituent).

Preferable examples of $R^2$ include cyano group or group represented by Formula $-CONV^{a11}V^{a12}$ (wherein, $V^{a11}$ and $V^{a12}$ have the same meaning as defined above).

More preferable examples of $R^2$ include cyano group or group represented by Formula $-CONHV^{a16}$ (wherein, $V^{a16}$ represents a hydrogen atom, $C_{1-6}$ alkyl group, $C_{3-8}$ cycloalkyl group, $C_{1-6}$ alkoxy group or $C_{3-8}$ cycloalkoxy group, where $V^{a16}$ may have a substituent selected from a halogen atom, cyano group, hydroxyl group and $C_{1-6}$ alkoxy group).

Still more preferable example of $R^2$ includes group represented by Formula $-CONHV^{a17}$ (wherein, $V^{a17}$ represents a hydrogen atom, $C_{1-6}$ alkyl group or $C_{1-6}$ alkoxy group).

The most preferable example of $R^2$ include group represented by Formula $-CONHV^{a18}$ (wherein, $V^{a18}$ represents a hydrogen atom, methyl group or methoxy group).

(iii) $Y^1$ $Y^1$ represents group represented by Formula

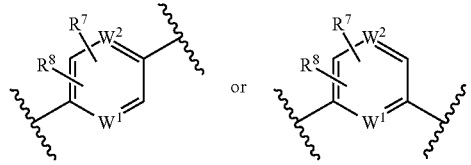

(wherein, $R^7$ and $R^8$ each independently represent a hydrogen atom, a halogen atom, cyano group, nitro group, amino group, $C_{1-6}$ alkyl group that may have a substituent, $C_{3-8}$ cycloalkyl group that may have a substituent, $C_{1-6}$ alkoxy group that may have a substituent, $C_{1-6}$ alkylthio group that may have a substituent, formyl group, $C_{2-7}$ acyl group that may have a substituent, $C_{2-7}$ alkoxycarbonyl group that may have a substituent or group represented by Formula $-CONV^{d1}V^{d2}$ (wherein, $V^{d1}$ and $V^{d2}$ each independently represent a hydrogen atom or $C_{1-6}$ alkyl group that may have a substituent); and $W^1$ and $W^2$ each independently represent a carbon atom or a nitrogen atom that may have a substituent).

A preferable example of $Y^1$ includes group represented by Formula

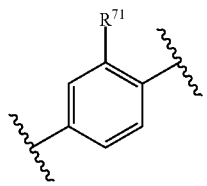

(wherein, $R^{71}$ represents a hydrogen atom or a halogen atom).

(iv) $R^3$ and $R^4$ $R^3$ and $R^4$ each independently represent a hydrogen atom, $C_{1-6}$ alkyl group that may have a substituent, $C_{2-6}$ alkenyl group that may have a substituent, $C_{2-6}$ alkynyl group that may have a substituent, $C_{3-8}$ cycloalkyl group that may have a substituent, $C_{2-7}$ acyl group that may have a substituent or $C_{2-7}$ alkoxycarbonyl group that may have a substituent.

A preferable example of $R^3$ and $R^4$ includes a hydrogen atom.

(v) $R^5$ $R^5$ represents a hydrogen atom, $C_{1-6}$ alkyl group that may have a substituent, $C_{2-6}$ alkenyl group that may have a substituent, $C_{2-6}$ alkynyl group that may have a substituent, $C_{3-8}$ cycloalkyl group that may have a substituent, $C_{6-10}$ aryl group that may have a substituent, 5-10-membered heteroaryl group that may have a substituent or 3-10-membered nonaromatic heterocyclic group that may have a substituent.

Preferable examples of $R^5$ include a hydrogen atom. $C_{1-6}$ alkyl group, $C_{3-8}$ cycloalkyl group and $C_{6-10}$ aryl group (where $R^5$ may have a substituent selected from a halogen atom and methanesulfonyl group).

More preferable examples of $R^5$ include methyl group, ethyl group or cyclopropyl group.

Moreover, preferable examples of the compound represented by Formula (I) include:
N-(4-(6-cyano-7-(2-methoxyethoxy)-4-quinolyl)oxy-2-fluorophenyl)-N'-(4-fluorophenyl)urea;
N-(2-chloro-4-((6-cyano-7-((1-methyl-4-piperidyl)methoxy)-4-quinolyl)oxy)phenyl)-N'-cyclopropylurea;
N-(4-((6-cyano-7-(((2R)-3-(diethylamino)-2-hydroxypropyl)oxy)-4-quinolyl)oxy)phenyl)-N'-(4-fluorophenyl)urea;
N-(4-((6-cyano-7-(((2R)-2-hydroxy-3-(1-pyrrolidino)propyl)oxy)-4-quinolyl)oxy)phenyl)-N'-(4-fluorophenyl)urea;
4-(3-chloro-4-(cyclopropylaminocarbonyl)aminophenoxy)-7-methoxy-6-quinolinecarboxamide;
4-(3-chloro-4-(cyclopropylaminocarbonyl)aminophenoxy)-7-(2-methoxyethoxy)-6-quinolinecarboxamide;
N6-cyclopropyl-4-(3-chloro-4-(((cyclopropylamino)carbonyl)amino)phenoxy)-7-methoxy-6-quinolinecarboxamide;
N6-(2-methoxyethyl)-4-(3-chloro-4-(((cyclopropylamino)carbonyl)amino)phenoxy)-7-methoxy-6-quinolinecarboxamide;
N6-(2-fluoroethyl)-4-(3-chloro-4-(((cyclopropylamino)carbonyl)amino)phenoxy)-7-methoxy-6-quinolinecarboxamide;
N6-methoxy-4-(3-chloro-4-(((cyclopropylamino)carbonyl)amino)phenoxy)-7-methoxy-6-quinolinecarboxamide;
N6-methyl-4-(3-chloro-4-(((cyclopropylamino)carbonyl)amino)phenoxy)-7-methoxy-6-quinolinecarboxamide;
N6-ethyl-4-(3-chloro-4-(((cyclopropylamino)carbonyl)amino)phenoxy)-7-methoxy-6-quinolinecarboxamide;
4-(3-fluoro-4-(cyclopropylaminocarbonyl)aminophenoxy)-7-(2-methoxyethoxy)-6-quinolinecarboxamide;
4-(3-chloro-4-(cyclopropylaminocarbonyl)aminophenoxy)-7-(2-hydroxyethoxy)-6-quinolinecarboxamide;
4-(3-chloro-4-(cyclopropylaminocarbonyl)aminophenoxy)-7-(2S)-2,3-dihydroxypropyl)oxy-6-quinolinecarboxamide;
4-(3-chloro-4-(methylaminocarbonyl)aminophenoxy)-7-methoxy-6-quinolinecarboxamide;
4-(3-chloro-4-(ethylaminocarbonyl)aminophenoxy)-7-methoxy-6-quinolinecarboxamide;
N6-methoxy-4-(3-chloro-4-(((ethylamino)carbonyl)amino)phenoxy)-7-methoxy-6-quinolinecarboxamide;
4-(3-chloro-4-(cyclopropylaminocarbonyl)aminophenoxy)-7-(2-ethoxyethoxy)-6-quinolinecarboxamide;
4-(4-((cyclopropylamino)carbonyl)aminophenoxy)-7-(2-methoxyethoxy)-6-quinolinecarboxamide;
N-(2-fluoro-4-((6-carbamoyl-7-methoxy-4-quinolyl)oxy)phenyl)-N'-cyclopropylurea;
N6-(2-hydroxyethyl)-4-(3-chloro-4-(((cyclopropylamino)carbonyl)amino)phenoxy)-7-methoxy-6-quinolinecarboxamide;
4-(3-chloro-4-(1-propylaminocarbonyl)aminophenoxy)-7-methoxy-6-quinolinecarboxamide;
4-(3-chloro-4-(cis-2-fluoro-cyclopropylaminocarbonyl)aminophenoxy)-7-methoxy-6-quinolinecarboxamide;
N6-methyl-4-(3-chloro-4-(((cyclopropylamino)carbonyl)amino)phenoxy)-7-(2-methoxyethoxy)-6-quinolinecarboxamide;
N6-methyl-4-(3-chloro-4-(((ethylamino)carbonyl)amino)phenoxy)-7-methoxy-6-quinolinecarboxamide;
4-(3-chloro-4-(cyclopropylaminocarbonyl)aminophenoxy)-7-(2-(4-morpholino)ethoxy)-6-quinolinecarboxamide;
4-(3-chloro-4-(2-fluoroethylaminocarbonyl)aminophenoxy)-7-methoxy-6-quinolinecarboxamide;
N6-((2R)tetrahydro-2-furanylmethyl)-4-(3-chloro-4-(((methylamino)carbonyl)amino)phenoxy)-7-methoxy-6-quinolinecarboxamide;
4-(3-fluoro-4-(ethylaminocarbonyl)aminophenoxy)-7-methoxy-6-quinolinecarboxamide;
4-(3-chloro-4-(((cyclopropylamino)carbonyl)amino)phenoxy)-7-((2R)-2-hydroxy-3-(1-pyrrolidino)propoxy)-6-quinolinecarboxamide;
N6-methyl-4-(3-chloro-4-(((methylamino)carbonyl)amino)phenoxy)-7-((2R)-3-diethylamino-2-hydroxypropoxy)-6-quinolinecarboxamide;
N6-methyl-4-(3-chloro-4-(((ethylamino)carbonyl)amino)phenoxy)-7-((2R)-3-diethylamino-2-hydroxypropoxy)-6-quinolinecarboxamide;
N6-methyl-4-(3-chloro-4-(((methylamino)carbonyl)amino)phenoxy)-7-((2R)-2-hydroxy-3-(1-pyrrolidino)propoxy)-6-quinolinecarboxamide;
N6-methyl-4-(3-chloro-4-(((ethylamino)carbonyl)amino)phenoxy)-7-((2R)-2-hydroxy-3-(1-pyrrolidino)propoxy)-6-quinolinecarboxamide;
N6-methyl-4-(3-chloro-4-(((methylamino)carbonyl)amino)phenoxy)-7-((1-methyl-4-piperidyl)methoxy)-6-quinolinecarboxamide;
N6-methyl-4-(3-chloro-4-(((ethylamino)carbonyl)amino)phenoxy)-7-((1-methyl-4-piperidyl)methoxy)-6-quinolinecarboxamide;
N-(4-(6-cyano-7-(2-methoxyethoxy)-4-quinolyl)oxy-2-fluorophenyl)-N'-cyclopropylurea
N-(4-(6-cyano-7-(3-(4-morpholino)propoxy)-4-quinolyl)oxyphenyl)-N'-(3-(methylsulfonyl)phenyl)urea;

4-(4-((cyclopropylamino)carbonyl)aminophenoxy)-7-methoxy-6-quinolinecarboxamide;

4-(3-fluoro-4-((2-fluoroethylamino)carbonyl)aminophenoxy)-7-methoxy-6-quinolinecarboxamide;

N6-(2-ethoxyethyl)-4-(3-chloro-4-(((methylamino)carbonyl)amino)phenoxy)-7-methoxy-6-quinolinecarboxamide;

4-(4-(3-ethylureido)-3-fluoro-phenoxy)-7-methoxyquinoline-6-carboxylic acid(2-cyanoethyl)amide; and N-(4-(6-(2-cyanoethyl)carbamoyl-7-methoxy-4-quinolyl)oxy-2-fluorophenyl)-N'-cyclopropylurea.

More preferable examples of the compound represented by Formula (I) further include:

4-(3-chloro-4-(cyclopropylaminocarbonyl)aminophenoxy)-7-methoxy-6-quinolinecarboxamide;

4-(3-chloro-4-(ethylaminocarbonyl)aminophenoxy)-7-methoxy-6-quinolinecarboxamide;

N6-methoxy-4-(3-chloro-4-(((cyclopropylamino)carbonyl)amino)phenoxy)-7-methoxy-6-quinolinecarboxamide;

4-(3-chloro-4-(methylaminocarbonyl)aminophenoxy)-7-methoxy-6-quinolinecarboxamide; and N6-methoxy-4-(3-chloro-4-(((ethylamino)carbonyl)amino)phenoxy)-7-methoxy-6-quinolinecarboxamide.

A still more preferable example of the compound represented by Formula (I) further includes 4-(3-chloro-4-(cyclopropylaminocarbonyl)aminophenoxy)-7-methoxy-6-quinolinecarboxamide (see Formula (II)).

The most preferable example of the compound represented by Formula (I), a pharmacologically acceptable salt thereof or a solvate thereof includes methanesulfonate of 4-(3-chloro-4-(cyclopropylaminocarbonyl)aminophenoxy)-7-methoxy-6-quinolinecarboxamide.

(II)

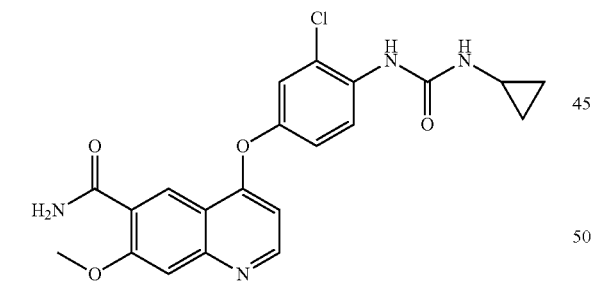

The compound represented by Formula (I) can be produced by a known method, for example, by methods described in International publication No. 02/32872 pamphlet (WO02/32872) and International publication No. 2005/063713 pamphlet (WO2005/063713).

(B) C-Kit Inhibitor

According to the present invention, examples of the c-kit inhibitor include:

(1) 4-(4-methylpiperazine-1-ylmethyl)-N-[4-methyl-3-[4-(3-pyridyl)pyrimidine-2-ylamino]phenyl]benzenamide (hereinafter, also referred to as "imatinib" or "ST1571". Blood, 96, 925-932, 2000, Bioorganic and Medicinal Chemistry Letters, 7: 187-192, 1997) (see Formula (III))

(III)

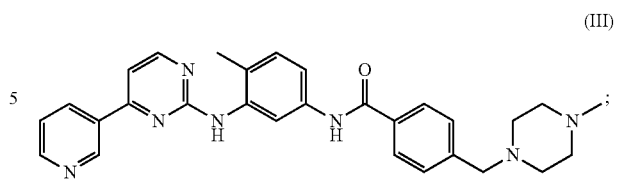

(2) 3-[(2,4-dimethylpyrrole-5-yl)methylene]-2-indolinone (hereinafter, also referred to as "SU5416" or "semaxanib". Cancer Research., 61, 3660-3668, 2001, Journal of Medicinal Chemistry., 41:2588-2603, 1998., U.S. Pat. No. 5,792,783) (see Formula (IV)).

(IV)

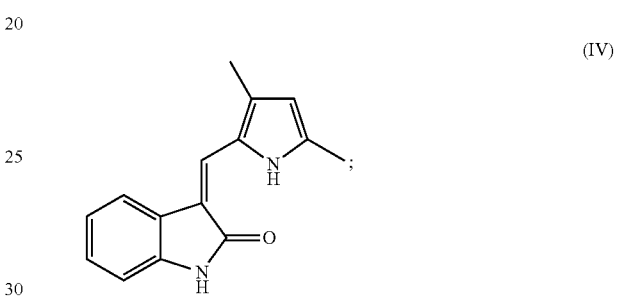

(Z)-3-[(2,4-dimethyl-5-(2-oxo-1,2-dihydroindole-3-ylidenemethyl)-1H-pyrrole-3-yl)-propionic acid (hereinafter, also referred to as "SU6668". Cancer Research., 61, 3660-3668, 2001, Journal of Medicinal Chemistry., 42:5120-5130, 1999.) (see Formula (V))

(V)

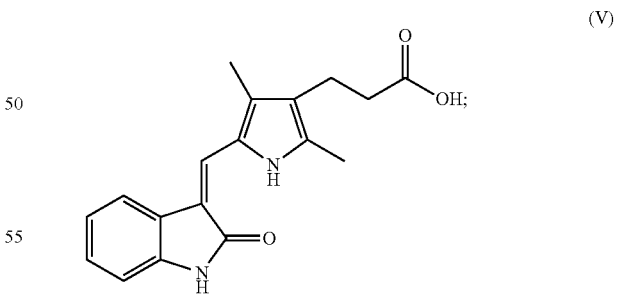

(4) 5-(5-fluoro-2-oxo-1,2-dihydroindole-3-ylidenemethyl)-2,4-dimethyl-1H-pyrrole-3-carboxylic acid (2-diethylaminoethyl)amide (hereinafter, also referred to as "SU11248". Molecular Cancer Therapeutics, 2:471-478, 2003, Journal of Medicinal Chemistry, 46: 1116-9, 2003.) (see Formula (VI))

(VI)

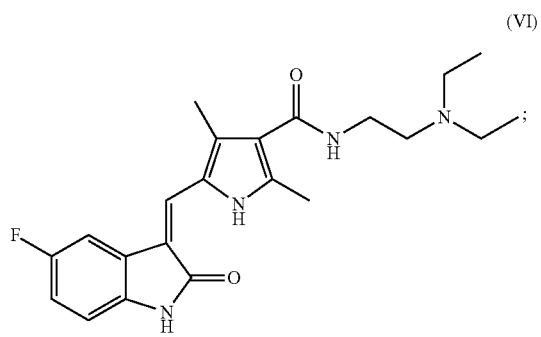 [SMILES: CCN(CC)CCNC(=O)c1c(C)[nH]c(/C=C2\C(=O)Nc3ccc(F)cc32)c1C]

(5) N-{2-chloro-4-[(6,7-dimethoxy-4-quinazolinyl)oxy]phenyl}-N'-propylurea (hereinafter, also referred to as "KRN633". Molecular Cancer Therapeutics, 3:1639-49, 2004) (see Formula (VII))

(VII)

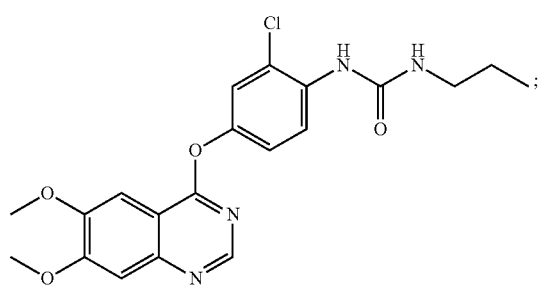

(6) 1-(4-chloroanilino)-4-(4-pyridylmethyl)phthalazine (hereinafter, also referred to as "PTK787/ZK222584" or "vatalanib". Cancer Research, 60, 2178-2189, 2000, Journal of Medicinal Chemistry, 43:2310-23, 2000, WO98/35958) (see Formula (VIII))

(VIII)

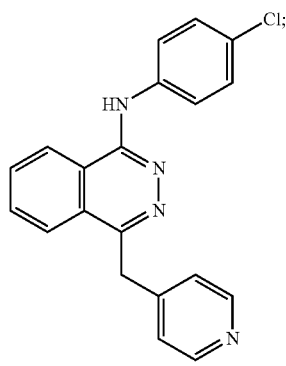

(7) N-{2-chloro-4-[(6,7-dimethoxy-4-quinolyl)oxy]phenyl}-N'-(5-methyl-3-isoxazolyl)urea (hereinafter, also referred to as "KRN951". Proceedings of the American Association for Cancer Research, 45, 594, (Abstract 2571), 2004, Proceedings of the American Association for Cancer Research, 45, 595, (Abstract 2575), 2004, WO2002/088110) (see Formula (IX))

(IX)

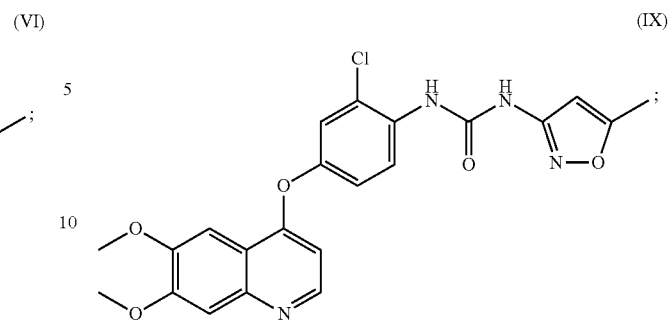

(8) 4-[(4-fluoro-2-methylindole-5-yl)oxy]-6-methoxy-7-[3-(pyrrolidine-1-yl)propoxy]quinazoline (hereinafter, also referred to as "AZD2171". Cancer Research. 65:4389-400, 2005, WO00/47212) (see Formula (X))

(X)

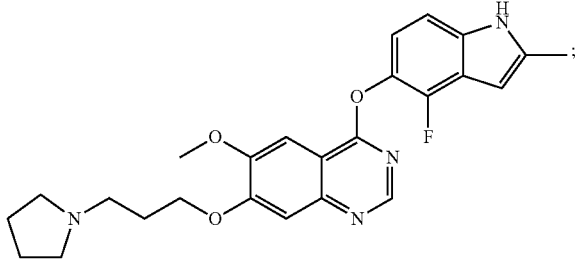

(9) 6-[2-(methylcarbamoyl)phenylsulfanil]-3-E-[2-(pyridine-2-yl)ethenyl]indazole (hereinafter, also referred to as "AG013736". Proceedings of the American Association for Cancer Research, 44, 865, (Abstract 3780), 2003, American Journal of Pathology. 165:35-52, 2004. WO01/002369) (see Formula (XI))

(XI)

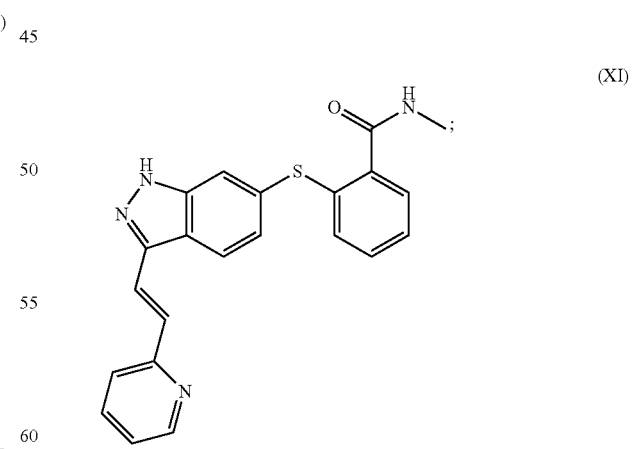

(10) N-(3-trifluoromethyl-4-chlorophenyl)-N'-(4-(2-methylcarbamoylpyridine-4-yl)oxyphenyl)urea (hereinafter, also referred to as "BAY 43-9006" or "sorafenib". Cancer Research, 64, 7099-7109, 2004, Organic Process Res Dev., 6, 777-81, 2002, WO00/42012) (see Formula (XII))

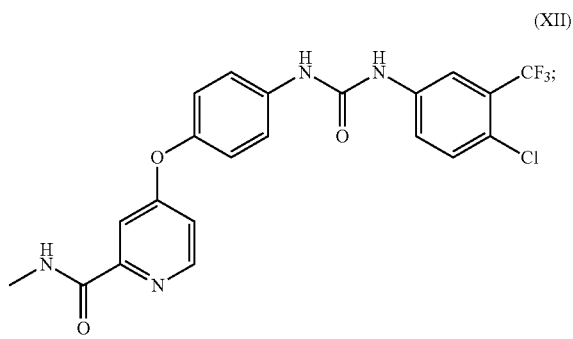
(XII)

(11) [6-[4-[(4-ethylpiperazine-1-yl)methyl]phenyl]-7H-pyrrolo[2,3-d]pyrimidine-4-yl]-((R)-1-phenylethyl)amine (hereinafter, also referred to as "AEE-788". Cancer Research, 64, 4931-4941, 2004, Cancer Research, 64, 7977-7984, 2004.) (see Formula (XIII))

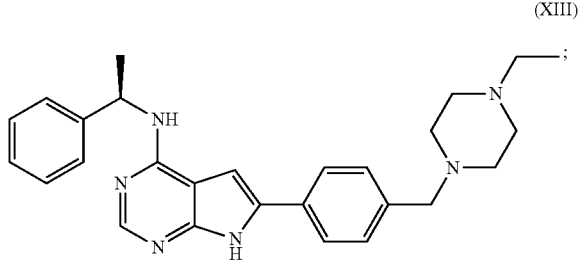 [SMILES: CCN1CCN(Cc2ccc(-c3cc4c(N[C@H](C)c5ccccc5)ncnc4[nH]3)cc2)CC1]
(XIII)

(12) 6-(2,6-dichloro-phenyl)-2-(4-fluoro-3-methyl-phenylamino)-8-methyl8H-pyrido[2,3-d]pyrimidine-7-one (hereinafter, also referred to as "PD180970". Cancer Research, 62, 4244-4255, 2002, Journal of Medicinal Chemistry, 40, 2296-2303, 1997.) (see Formula (XIV))

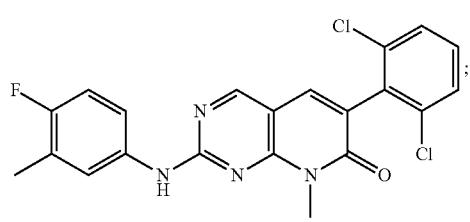
(XIV)

(13) 6-(2,6-dichlorophenyl)-8-methyl-2-(3-methylsulfanilphenylamino)-8H-pyrido[2,3-/d/]pyrimidine-7-one (hereinafter, also referred to as "PD173955". Cancer Research, 62, 4244-4255, 2002, Journal of Medicinal Chemistry, 40, 2296-2303, 1997.) (see Formula (XV))

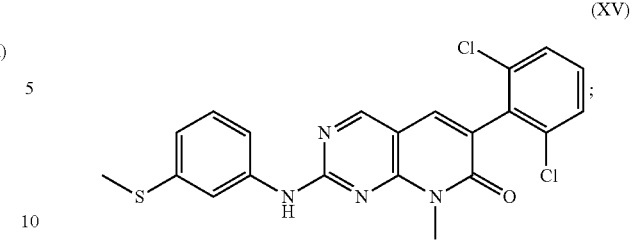
(XV)

(14) 4-[6-methoxy-7-(3-piperidine-1-yl-propoxy)quinazoline-4-yl]piperazine-1-carboxylic acid(4-isopropoxyphenyl)amide (hereinafter, also referred to as "MLN518" or "tandutinib". Blood, 104, 3754-3757, 2004, Journal of Medicinal Chemistry, 45, 3772-3793, 2002.) (see Formula (XVI))

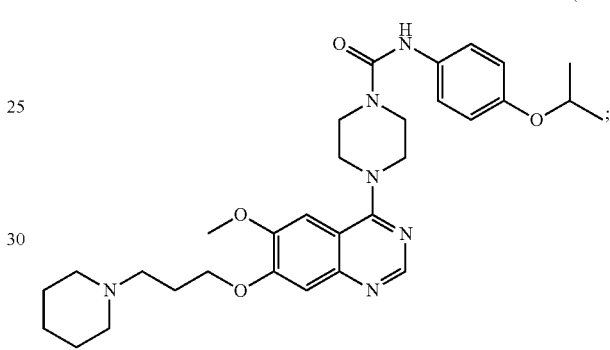
(XVI)

and

(15) N-(2-chloro-6-methylphenyl)-2-[[6-[4-(2-hydroxyethyl)piperazine-1-yl]-2-methylpyrimidine-4-yl]amino]thiazole-5-carboxamide (hereinafter, also referred to as "BMS-354825" or "dasatinib". Proceedings of the National Academy of Sciences of the United States of America, 102, 11011-11016, 2005.) (see Formula (XVII))

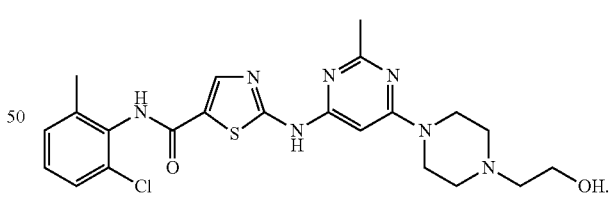
(XVII)

Imatinib, SU5416, SU6668, SU11248, KRN633, PTK787/ZK222584, KRN951, AZD2171, AG013736, BAY 43-9006, AEE-788, PD180970, PD173955, MLN518 and BMS-354825 can be produced by a known method, for example, by methods described in the respective documents.

In addition, imatinib is available by purchasing Glivec™ from Novartis Pharma K.K.

According to the present invention, the compound represented by Formula (I) and/or the c-kit inhibitor may form a pharmacologically acceptable salt with acid or base. The compound represented by Formula (I) and/or the c-kit inhibitor of the invention also comprises such pharmacologically acceptable salts. Examples of salts formed with acid include inorganic acid salts such as hydrochloride, hydrobromate, sulfate and phosphate, and organic acid salts such as formic acid, acetic acid, lactic acid, succinic acid, fumaric acid, maleic acid, citric acid, tartaric acid, stearic acid, benzoic acid, methanesulfonic acid, benzenesulfonic acid, p-toluene-sulfonic acid and trifluoroacetic acid. Examples of salts formed with base include alkali metal salts such as sodium salt and potassium salt, alkaline earth metal salts such as calcium salt and magnesium salt, organic base salts such as trimethylamine, triethylamine, pyridine, picoline, dicyclo-hexylamine, N,N'-dibenzyl ethylenediamine, arginine and lysine and ammonium salt.

Furthermore, according to the present invention, the compound represented by Formula (I) and/or the c-kit inhibitor also comprises, if any, solvates and enantiomers thereof. Examples of solvates include hydrates and nonhydrates, preferably hydrates. Examples of solvents include water, alcohols (for example, methanol, ethanol, n-propanol) and dimethylformamide.

Moreover, according to the present invention, the compound represented by Formula (I) may be crystalline or amorphous. If a crystalline polymorph is present, it may be a single product of any one of the crystal forms or a mixture of such forms.

According to the present invention, the compound of the invention and/or the c-kit inhibitor also comprises compounds that generate the compound represented by Formula (I) and/or the c-kit inhibitor by undergoing metabolism such as oxidation, reduction and hydrolysis in vivo.

According to the present invention, an example of the c-kit inhibitor includes an anti-c-kit kinase antibody.

According to the present invention, an anti-c-kit kinase antibody is an antibody that has affinity with c-kit kinase or a partial fragment thereof. Preferably, an anti-c-kit kinase antibody is a neutralizing antibody that recognizes and binds with c-kit kinase to inhibit the vascular endothelial cell growth activity of c-kit kinase. According to the present invention, an anti-c-kit kinase antibody is, for example, a polyclonal antibody, a monoclonal antibody, a chimeric antibody, a single-chain antibody (scFV) (Huston et al. (1988) Proc. Natl. Acad. Sci. USA 85:5879-83; The Pharmacology of Monoclonal Antibody, vol. 113, Rosenburg and Moore ed., Springer Verlag (1994) pp. 269-315), a humanized antibody, a polyspecific antibody (LeDoussal et al. (1992) Int. J. Cancer Suppl. 7:58-62; Paulus (1985) Behring Inst. Mitt. 78:118-32; Millstein and Cuello (1983) Nature 305:537-9; Zimmermann (1986) Rev. Physiol. Biochem. Pharmacol. 105:176-260; Van Dijk et al. (1989) Int. J. Cancer 43: 344-349), or antibody fragments such as Fab, Fab', F(ab')2, Fc and Fv, preferably a monoclonal antibody. Furthermore, if necessary, an anti-c-kit kinase antibody may be modified with polyethylene glycol (PEG) or the like. Otherwise, an anti-c-kit kinase antibody may be produced as a fusion protein with β-galactosidase, MBP (maltose binding protein), GST (glutathione S-transferase), GFP (green fluorescence protein) or the like, which can be detected in an ELISA method or the like without using a secondary antibody. An anti-c-kit kinase antibody may be modified by being labeled with biotin or the like such that the antibody can be collected using avidin, streptavidin or the like.

An anti-c-kit kinase antibody may be produced according to a conventional method using c-kit kinase or a partial fragment thereof (hereinafter, also referred to as a "polypeptide fragment of c-kit kinase"), or a cell expressing c-kit kinase or a partial fragment thereof as a sensitized antigen ("Current Protocols in Molecular Biology" (John Wiley & Sons (1987) Section 11.4-11.13)). In this case, a polypeptide fragment of c-kit kinase may be a fusion protein with an Fc region, GST, MBP, GFP, AP (alkaline phosphatase) or the like.

A polyclonal antibody and a monoclonal antibody may be prepared according to a method known by those skilled in the art (Antibodies: A Laboratory Manual, E. Harlow and D. Lane, ed., Cold Spring Harbor Laboratory (Cold Spring Harbor, N.Y., 1988)).

A polyclonal antibody may be obtained, for example, by administering an antigen to a mammal such as a mouse, a rabbit or a rat, collecting blood from this mammal, and separating and purifying an antibody from the collected blood. Immune sensitization methods are known by those skilled in the art, and may be carried out, for example, by administering an antigen once or more. Furthermore, an antigen (a polypeptide fragment of c-kit kinase) may be used by dissolving it in an appropriate buffer such as a buffer containing a complete Freund's adjuvant or a generally used adjuvant such as aluminum hydroxide, although no adjuvant may be used depending on the administration route or conditions.

Blood is taken from the mammal 1-2 months after the last immune sensitization, and separated and purified according to a conventional method such as centrifugation, precipitation using ammonium sulfate or polyethyleneglycol and various chromatographies, thereby obtaining a polyclonal antibody as a polyclonal antiserum.

An example of a method for producing a monoclonal antibody includes a hybridoma technique. The hybridoma technique first sensitizes a mammal in the same manner as in the production of the polyclonal antibody. Preferably, partial blood collection is carried out appropriate days after the sensitization to determine the antibody titer by a known method such as ELISA method.

Subsequently, spleen is removed from the sensitized animal to obtain B cells. Then, the B cells are fused with myeloma cells by a common method to produce antibody-producing hybridomas. The myeloma cells used are not particularly limited and known cells may be used. The method for fusing the cells may be any method selected from methods known in the art such as Sendai virus technique, polyethyleneglycol technique and protoplast technique. The obtained hybridomas are cultured for an appropriate period of time in an HAT medium (a medium containing hypoxanthine, aminopterin and thymidine) by a common method for hybridoma selection. Then, the antibody-producing hybridoma of interest may be screened and cloned.

A known antibody detecting method such as ELISA method or radioimmunoassay method may be used as the screening method, and a method known in the art such as limiting dilution technique, FACS method or the like may be used as the cloning method. The obtained hybridoma may be cultured in an appropriate culture solution, or may be intraperitoneally administered, for example, to a mouse that is compatible with the hybridoma. The desired monoclonal antibody can be isolated and purified from the resulting culture solution or ascites by salt-out, ion-exchange chromatography, gel filtration, affinity chromatography or the like.

2. Pharmaceutical Composition, Kit and Method for Treating Cancer

The present invention relates to a pharmaceutical composition, a kit, a method for treating cancer or the like characterized by combining a compound of the invention and a c-kit inhibitor.

According to the present invention, the c-kit inhibitor is not particularly limited as long as it has an activity of inhibiting c-kit kinase. Examples of the c-kit inhibitor include a c-kit kinase inhibitor and an anti-c-kit kinase antibody. Preferable examples of c-kit inhibitors include imatinib, SU5416, SU6668, SU11248, KRN633, PTK787/ZK222584, KRN951, AZD2171, AG013736, BAY 43-9006, AEE-788, PD180970, PD173955, MLN518 and BMS-354825, and more preferable example includes imatinib.

According to the present invention, the phrase "in combination" refers to a combination for combined use of the compound, and includes both a form for concomitantly using separate substances upon administration and a form as a mixture.

The dosage form of the formulation included in the kit of the invention is not particularly limited as long as it contains the compound of the invention and/or the c-kit inhibitor. The pharmaceutical composition and/or the kit of the invention is useful as a pharmaceutical composition and/or a kit for treating cancer.

The pharmaceutical composition and/or the kit of the invention may be used as a drug for treating cancer.

According to the present invention, a drug for treating cancer comprises an anti-tumor drug, a drug for improving prognosis of cancer, a drug for preventing cancer recurrence, a drug for suppressing cancer metastasis and the like.

The effect of cancer treatment may be confirmed by observation of a x-ray picture, CT or the like, by histopathological diagnosis of biopsy, or from a tumor marker value.

The pharmaceutical composition and/or the kit of the invention may be administered to a mammal (e.g., human, rat, rabbit, sheep, pig, bovine, cat, dog, monkey, etc.).

The types of cancer treated by the drug are not particularly limited and may include, for example, brain cancer, head & neck cancer, esophagus cancer, tongue cancer, lung cancer, breast cancer, pancreatic cancer, stomach cancer, small intestine cancer, duodenum cancer, colorectal cancer (colon cancer, rectal cancer), bladder cancer, kidney cancer, liver cancer, prostate cancer, uterus cancer, ovary cancer, thyroid gland cancer, gallbladder cancer, pharynx cancer, sarcoma (e.g., osteosarcoma, chondrosarcoma, Kaposi's sarcoma, myosarcoma, angiosarcoma, fibrosarcoma, etc.), leukemia (e.g., chronic myeloid leukemia (CML), acute myeloid leukemia (AML), chronic lymphatic leukemia (CLL) and acute lymphatic leukemia (ALL), lymphoma, multiple myeloma (MM), etc.) and melanoma.

The pharmaceutical composition and/or the kit of the invention may be used through oral or parental administration. When the pharmaceutical composition and/or the kit of the invention is used, the given dose of the compound of the invention differs depending on the degree of the symptom, age, sex, weight and sensitivity difference of the patient, administration mode, administration period, administration interval, nature, prescription and the type of the pharmaceutical formulation, and the type of the active element. Usually, but without limitation, the dose of the compound is 0.1-1000 mg/day, preferably 0.5-100 mg/day, more preferably 1-30 mg/day for an adult (weight 60 kg), which may be administered once to three times a day.

When the pharmaceutical composition and/or kit of the invention is used, the given dose of the c-kit inhibitor is usually, but without limitation, 10-6000 mg/day, preferably 50-4000 mg/day, more preferably 50-2000 mg/day for an adult, which may be administered once to three times a day.

In addition, when the pharmaceutical composition and/or the kit of the invention is used, the given dose of the c-kit kinase inhibitor is usually, but without limitation, 10-6000 mg/day, preferably 50-4000 mg/day, more preferably 50-2000 mg/day for an adult, which may be administered once to three times a day.

When the pharmaceutical composition and/or the kit of the invention is used, the given dose of an anti-c-kit kinase antibody is usually, but without limitation, 1-6000 mg/day, preferably 10-2000 mg/day, more preferably 10-1000 mg/day for an adult, which may be administered once a day or a week.

The amount of the compound of the invention used is not particularly limited and may differ according to the individual combination with the c-kit inhibitor, for example, it may be about 0.01-100 times (weight ratio) the amount of the c-kit inhibitor. More preferably, it is about 0.1-10 times (weight ratio) the amount of the c-kit inhibitor.

The pharmaceutical composition of the invention may be made into various forms, for example, into solid oral formulations, injectable solution or the like.

Furthermore, each of the compound and the c-kit inhibitor contained in the kit of the invention may individually be made into solid oral formulations, injectable solution or the like.

In order to prepare a solid oral formulation, an excipient, and if necessary, a binder, disintegrant, lubricant, colorant, a flavoring agent and the like are added to the principal agent, and then made into a tablet, a coated tablet, granule, fine granule, dispersant, a capsule or the like according to a conventional method.

For example, lactose, cornstarch, sucrose, glucose, sorbit, crystalline cellulose, silicon dioxide or the like may be used as the excipient; for example, polyvinyl alcohol, ethyl cellulose, methyl cellulose, gum arabic, hydroxypropyl cellulose, hydroxypropylmethyl cellulose or the like may be used as the binder; for example, magnesium stearate, talc, silica or the like may be used as the lubricant; those that are allowed to be added to drugs may be used as the colorant; and for example, cocoa powder, menthol, aromatic acid, peppermint oil, camphor, cinnamon powder or the like may be used as the flavoring agent. Of course, if necessary, these tablets and granule may be coated appropriately with sugar coating, gelatin coating or else.

When an injectable solution is to be prepared, if necessary, the principal agent may be added with a pH adjuster, a buffer, a suspending agent, a solubilizing agent, a stabilizer, a tonicity agent, a preservative or the like, and may be made into an intravenously, subcutaneously or intramuscularly injectable solution according to a conventional method. If necessary, the solution may be made into a lyophilized form by a conventional technique.

Examples of the suspending agent include methyl cellulose, Polysorbate 80, hydroxyethyl cellulose, gum arabic, powdered tragacanth, carboxy methyl cellulose sodium and polyoxyethylene sorbitan monolaurate.

Examples of the solubilizing agent include polyoxyethylene hydrogenated castor oil, Polysorbate 80, nicotine acid amide, polyoxyethylene sorbitan monolaurate, macrogol, and castor oil fatty acid ethyl ester.

Examples of the stabilizer include sodium sulfite and sodium metasulfite; examples of the preservative include methyl parahydroxybenzoate, ethyl parahydroxybenzoate, sorbic acid, phenol, cresol and chlorocresol.

In the kit of the invention, a formulation containing the compound of the invention and a formulation containing the c-kit inhibitor may be mixed together or may be separately accommodated and packed together. The order of the formulations above is not particularly limited and they may be administered simultaneously or one may be administered after the other.

Besides the compound of the invention and the c-kit inhibitor, the pharmaceutical composition and/or the kit of the invention may also contain a package, an instruction, an attached document or the like. The package, the instruction, the attached document or the like may include description of a combination employed for using substances, and description of usage and dosage in the case of administering separate substances in combination or in the case of administering them in a form of a mixture. The usage and dosage may be described referring to the related description above.

The kit of the invention may also comprise: (a) at least one selected from the group consisting of a package, an instruction and an attached document describing combined use of the compound of the invention and the c-kit inhibitor; and (b) a pharmaceutical composition containing the compound of the invention. The kit is useful for treating cancer. The pharmaceutical composition containing the compound of the invention is useful for treating cancer. The package, the instruction, the attached document or the like may include the description of combined use of the compound, and description of usage and dosage in the case of administering separate substances in combination upon administration or in the case of administering them in the form of a mixture. The usage and dosage may be described referring to the description of pharmaceutical composition and kit above.

The present invention also comprises use of a compound of the invention for producing a pharmaceutical composition in combination with a c-kit inhibitor. According to the use of the invention, the pharmaceutical composition is useful for treating cancer.

The present invention also comprises a method for preventing or treating cancer comprising simultaneously or separately administering a compound of the invention and a c-kit inhibitor to a patient. According to the method of the invention for preventing or treating cancer, the route and the method for administering the compound of the invention and the c-kit inhibitor are not particularly limited and reference may be made to the description of the pharmaceutical composition of the invention above.

The present invention also comprises a pharmaceutical composition containing the compound of the invention which is simultaneously or separately administered with a c-kit inhibitor to a patient. For the pharmaceutical composition of the invention, the route and the method for administering the compound of the invention and the c-kit inhibitor are not particularly limited and reference may be made to the description of the pharmaceutical composition of the invention above.

EXAMPLES

Hereinafter, the present invention will be illustrated by way of specific examples, although the invention should not be limited thereto.

Example 1

Combinational Use of Compound of the Invention and c-Kit Inhibitor in Human Cancer Cell Line Subcutaneous Xenograft Model (In Vivo)

Human gastrointestinal stromal tumor cell line GIST882 (supplied by The Brigham and Women's Hospital, Inc.) was cultured in RPMI1640 (containing 10% FBS) in a 5% carbon dioxide incubator to about 80% confluence. Following cultivation, each cell was collected by trypsin-EDTA treatment according to a general method. Using a phosphate buffer containing 50% matrigel, $5 \times 10^7$ cells/mL suspension was prepared, and 0.2 mL each of the resulting cell suspension was subcutaneously transplanted into the flank of a nude mouse. Starting from twenty-one days after the transplantation, 4-(3-chloro-4-(cyclopropylaminocarbonyl)aminophenoxy)-7-methoxy-6-quinolinecarboxamide (10 mg/kg or 30 mg/kg, once a day, for two weeks) and imatinib (160 mg/kg, twice a day, for two weeks) were orally administered alone or in combination. 4-(3-chloro-4-(cyclopropylaminocarbonyl)aminophenoxy)-7-methoxy-6-quinolinecarboxamide(methanesulfonate) was prepared based on the description of International publication No. 02/32872 pamphlet (WO02/32872). Moreover, imatinib was purchased from Novartis Pharma K.K. The major and minor axes of tumors were measured with Digimatic caliper (Mitsutoyo), and tumor volumes and relative tumor volumes were calculated according to the following formulae.

Tumor Volume (TV)=Major axis of tumor (mm)×(Minor axis of tumor)$^2$ (mm$^2$)/2

Figure 2:
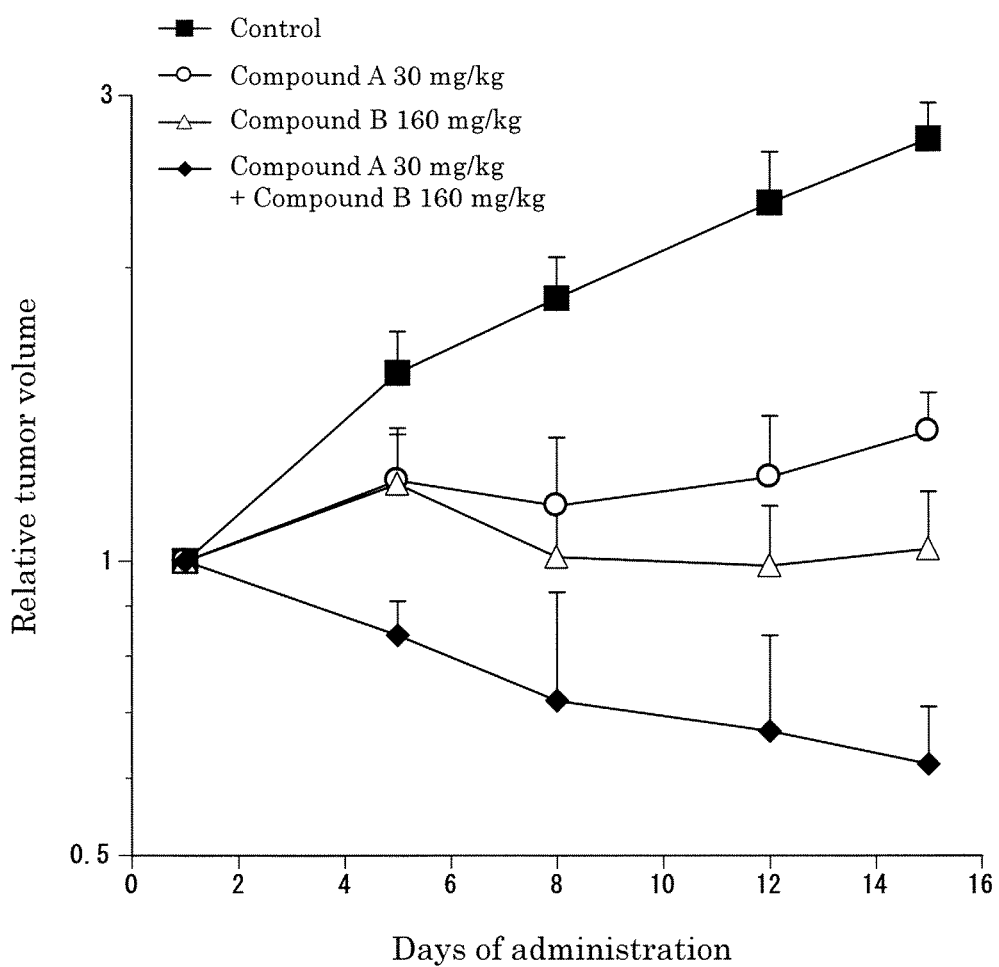
FIG. 2 shows the combined effect of a VEGF receptor kinase inhibitor and a c-kit inhibitor in a human cancer cell line subcutaneous xenograft model.

Relative Tumor Volume (RTV)=Tumor volume on measurement day/Tumor volume on the first administration day As a result, combined use of 4-(3-chloro-4-(cyclopropylaminocarbonyl)aminophenoxy)-7-methoxy-6-quinolinecarboxamide and imatinib showed greater antitumor effect than the case where 4-(3-chloro-4-(cyclopropylaminocarbonyl)aminophenoxy)-7-methoxy-6-quinolinecarboxamide or imatinib was used alone (Tables 1 and 2, FIGS. 1 and 2). Furthermore, combined use of 4-(3-chloro-4-(cyclopropylaminocarbonyl)aminophenoxy)-7-methoxy-6-quinolinecarboxamide and imatinib showed greater antitumor effect than the case where imatinib was used alone (Tables 1 and 2, FIGS. 1 and 2).

TABLE 1

| Administered compound | Relative tumor volume on Day 15 Average ± standard deviation |
|---|---|
| Control (untreated) | 2.71 ± 0.24 |
| Imatinib 160 mg/kg | 1.03 ± 0.15 |
| Compound A 10 mg/kg | 2.06 ± 0.16 |
| Compound A 10 mg/kg + imatinib 160 mg/kg | 0.77 ± 0.12 |

Table 1 shows antitumor effects obtained with 4-(3-chloro-4-(cyclopropylaminocarbonyl)aminophenoxy)-7-methoxy-6-quinolinecarboxamide (indicated as Compound A in Table 1) alone, imatinib alone and combined use of 4-(3-chloro-4-(cyclopropylaminocarbonyl)aminophenoxy)-7-methoxy-6-quinolinecarboxamide and imatinib in human cancer cell line subcutaneous xenograft models. The first day of administration was considered Day 1.

TABLE 2

| Administered compound | Relative tumor volume on Day 15 Average ± standard deviation |
|---|---|
| Control (untreated) | 2.71 ± 0.24 |
| Imatinib 160 mg/kg | 1.03 ± 0.15 |
| Compound A 30 mg/kg | 1.36 ± 0.13 |
| Compound A 30 mg/kg + imatinib 160 mg/kg | 0.62 ± 0.09 |

Table 2 shows antitumor effects obtained with 4-(3-chloro-4-(cyclopropylaminocarbonyl)aminophenoxy)-7-methoxy-6-quinolinecarboxamide (indicated as Compound A in Table 2) alone, imatinib alone and combined use of 4-(3-chloro-4-(cyclopropylaminocarbonyl)aminophenoxy)-7-methoxy-6-quinolinecarboxamide and imatinib in human cancer cell line subcutaneous xenograft models. The first day of administration was considered Day 1.

From the obtained results, the combination of 4-(3-chloro-4-(cyclopropylaminocarbonyl)aminophenoxy)-7-methoxy- 6-quinolinecarboxamide and imatinib was found to provide a pharmaceutical composition and a kit that show a remarkable antitumor activity, which can be used for treating cancer.

Reference Example

Hereinafter, a method for producing a formulation of one of the compounds represented by Formula (I), 4-(3-chloro-4-(cyclopropylaminocarbonyl)aminophenoxy)-7-methoxy-6-quinolinecarboxamide will be described as a reference example.

(Production of Pharmaceutical Composition)

(1) 1 mg Tablet 24 g of crystal (C) of 4-(3-chloro-4-(cyclopropylaminocarbonyl)aminophenoxy)-7-methoxy-6-quinolinecarboxamide methanesulfonate (hereinafter, also referred to as "crystal (C)", which was produced according to the method described in Example 7 of WO2005/063713) and 192 g of light anhydrous silicic acid (antigelling agent sold under the trade name of AEROSIL™ 200, Nippon Aerosil) were mixed with 20 L Super Mixer, and then 1236 g of D-mannitol (excipient, Towa-Kasei), 720 g of crystalline cellulose (excipient sold under the trade name of Avicel PH101, Asahi Kasei) and 72 g of hydroxypropylcellulose (binder sold under the trade name of HPC-L, Nippon Soda) were further added and mixed together. Subsequently, a suitable amount of anhydrous ethanol was added to obtain a granulated body containing crystal (C). This granulated body was dried in a rack dryer (60° C.), and then size-regulated using PowerMILL to obtain granules. Together with the granules, 120 g of croscarmellose sodium (disintegrant sold under the trade name of Ac-Di-Sol, FMC International Inc.) and 36 g of sodium stearyl fumarate (lubricant, JRS Pharma LP) were placed in a 20 L tumbler mixer and mixed together, and molded with a tablet machine to obtain tablets with a total mass of 100 mg per tablet. Moreover, the tablets were coated with a tablet coating machine using aqueous 10% Opadry yellow (OPADRY 03F42069 YELLOW, Colorcon Japan) solution as a coating solution, thereby obtaining coated tablets with a total mass of 105 mg per tablet.

(2) 10 mg Tablet 60 g of crystal (C) and 192 g of light anhydrous silicic acid (antigelling agent sold under the trade name of AEROSIL™ 200, Nippon Aerosil) were mixed with 20 L Super Mixer, and then 1200 g of D-mannitol (excipient, Towa-Kasei), 720 g of crystalline cellulose (excipient sold under the trade name of Avicel PH101. Asahi Kasei) and 72 g of hydroxypropylcellulose (binder sold under the trade name of HPC-L, Nippon Soda) were further added and mixed together. Subsequently, a suitable amount of anhydrous ethanol was added to obtain a granulated body containing crystal (C). This granulated body was dried in a rack dryer (60° C.), and then size-regulated using PowerMILL to obtain granules. Together with the granules, 120 g of croscarmellose sodium (disintegrant sold under the trade name of Ac-Di-Sol, FMC International Inc.) and 36 g of sodium stearyl fumarate (lubricant, JRS Pharma LP) were placed in a 20 L tumbler mixer and mixed together, and molded with a tablet machine to obtain tablets with a total mass of 400 mg per tablet. Moreover, the tablets were coated with a tablet coating machine using aqueous 10% Opadry yellow (OPADRY 03F42069 YELLOW, Colorcon Japan) solution as a coating solution, thereby obtaining coated tablets with a total mass of 411 mg per tablet.

(3) 100 mg Tablet 31.4 g of crystal (C) and 4 g of light anhydrous silicic acid (antigelling agent sold under the trade name of AEROSIL™ 200, Nippon Aerosil) were mixed with 1 L Super Mixer, and then 40.1 g of anhydrous calcium hydrogen phosphate (excipient, Kyowa Chemical Industry), 10 g of low substituted hydroxypropylcellulose (binder sold under the trade name of L-HPC (LH-21), Shin-Etsu Chemical) and 3 g of hydroxypropylcellulose (binder sold under the trade name of HPC-L, Nippon Soda) were further added and mixed together. Subsequently, a suitable amount of anhydrous ethanol was added to obtain a granulated body containing crystal (C). This granulated body was dried in a rack dryer (60° C.), and then granulated using PowerMILL to obtain granules. Together with the granules, 10 g of croscarmellose sodium (disintegrant sold under the trade name of Ac-Di-Sol. FMC International Inc.) and 1.5 g of sodium stearyl fumarate (lubricant, JRS Pharma LP) were mixed and molded with a tablet machine to obtain tablets with a total mass of 400 mg per tablet.

INDUSTRIAL APPLICABILITY

According to the present invention, there is provided a pharmaceutical composition and/or kit comprising a combination of a compound represented by Formula (I), a pharmacologically acceptable salt thereof or a solvate thereof and a c-kit inhibitor, which can be used for treating cancer.

What is claimed is:

1. A method for treating cancer comprising administering to a patient in need thereof an effective amount of 4-(3-chloro-4-(cyclopropylaminocarbonyl)aminophenoxy)-7-methoxy-6-quinolinecarboxamide, or a pharmacologically acceptable salt thereof, and an effective amount of 4-(4-methylipierazine-1-ylmethyl)-N-[4-methyl-3-[4-(3-pyridyl)pyrimidine-2-ylamino]phenyl]benzenamide or a pharmacologically acceptable salt thereof.

2. The method according to claim 1, wherein a methanesulfonate of 4-(3-chloro-4-(cyclopropylaminocarbonyl)aminophenoxy)-7-methoxy-6-quinolinecarboxamide is administered.

* * * * *